US012312361B2

(12) United States Patent
Wang

(10) Patent No.: US 12,312,361 B2
(45) Date of Patent: May 27, 2025

(54) METHODS FOR PRACTICAL SYNTHESIS OF DEUTERATED AMINO ACIDS

(71) Applicant: ARIZONA BOARD OF REGENTS ON BEHALF OF THE UNIVERSITY OF ARIZONA, Tucson, AZ (US)

(72) Inventor: Wei Wang, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 94 days.

(21) Appl. No.: 17/790,831

(22) PCT Filed: Feb. 4, 2021

(86) PCT No.: PCT/US2021/016599
§ 371 (c)(1),
(2) Date: Jul. 5, 2022

(87) PCT Pub. No.: WO2021/158781
PCT Pub. Date: Aug. 12, 2021

(65) Prior Publication Data
US 2023/0023607 A1    Jan. 26, 2023

Related U.S. Application Data

(60) Provisional application No. 62/978,175, filed on Feb. 18, 2020, provisional application No. 62/970,838, filed on Feb. 6, 2020.

(51) Int. Cl.
*C07D 493/04* (2006.01)
*C07D 263/26* (2006.01)
*C07D 413/06* (2006.01)
*C07D 493/14* (2006.01)

(52) U.S. Cl.
CPC ......... *C07D 493/04* (2013.01); *C07D 263/26* (2013.01); *C07D 413/06* (2013.01); *C07D 493/14* (2013.01); *C07B 2200/05* (2013.01)

(58) Field of Classification Search
None
See application file for complete search history.

(56) References Cited

FOREIGN PATENT DOCUMENTS

WO    WO2018099271 A1    6/2018

OTHER PUBLICATIONS

Wang et. al. (Org. Lett. 2020, 22, 1557-1562) (Year: 2020).*
Karady et. al (Tetrahedron Letters vol. 25, Issue 39, 1984, pp. 4337-4340) (Year: 1984).*
Atzrodt et al., "C-H Functionalisation for Hydrogen Isotope Exchange", Angew. Chem., Int. Ed. 2018, 57, pp. 3022-3047.
Atzrodt et al., "Deuterium- and Tritium-Labelled Compounds: Applications in the Life Sciences", Angew. Chem. Int. Ed. 2018, 57, pp. 1758-1784.
Axon et al., "Diastereoselective radical addition to methyleneoxazolidinones: an enantioselective route to α-amino acids", J. Chem. Soc. Chem. Commun. 1995, pp. 549-550.
Aycock et al., "A practical and scalable system for heteroaryl amino acid synthesis", Chem. Sci. 2017, 8, 7998-8003.
Aycock et al., "Aminoalkyl Radicals as Powerful Intermediates for the Synthesis of Unnatural Amino Acids and Peptides", ACS Catal. 2018, 8, pp. 9115-9119.
Baldwin et al., "Evidence for an insertion-homolysis mechanism for carbon-sulphur bond formation in penicillin biosynthesis; 1. Synthesis of tripeptide probes", Tetrahedron, 1996, vol. 52, pp. 2515-2536.
Bhatia et al., "Stereoretentive H/D Exchange via an Electroactivated Heterogeneous Catalyst at sp3C-H Sites Bearing Amines or Alcohols", Eur. J. Org. Chem. 2016, pp. 4230-4235.
Bottecchia et al., "Photocatalytic Modification of Amino Acids, Peptides and Proteins", Chem. Eur. J. 2019, 25, pp. 26-42.
Chatterjee et al., "Selective α-Deuteration of Amines and Amino Acids Using D2O", Org. Lett. 2016, 18, pp. 5892-5895.
Chen et al., "Visible light photoredox-controlled reactions of N-radicals and radical ions", Chem. Soc. Rev. 2016, 45, pp. 2044-2056.
Church et al., "Synthesis of the suicide substrate D-propargylglycine stereospecifically labelled with deuterium and investigation of its oxidation by D-amino acid oxidase", J. Chem. Soc. Perkin Trans. 1. 1998, 52, pp. 1475-1482.
Cowell et al., "Exploring Ramachandran and chi space: conformationally constrained amino acids and peptides in the design of bioactive polypeptide ligands", Curr. Med. Chem. 2004, 11, pp. 2785-2798.
de Bruijn et al., "Chemical Modification of Dehydrated Amino Acids in Natural Antimicrobial Peptides by Photoredox Catalysis", Chem. Eur. J. 2018, 24, pp. 11314-11318.
deGruyter et al., "Residue-Specific Peptide Modification: A Chemist's Guide", Biochemistry 2017, 56, pp. 3863-3873.
Easton, "Free-Radical Reactions in the Synthesis of a-Amino Acids and Derivatives", Chem. Rev. 1997, 97, pp. 53-82.
Elemes et al., "Synthesis of enantiopure α-deuteriated Boc-L-amino acids", J. Chem. Soc. Perkin Trans. 1. 1996. pp. 537-540.
Faleev et al., Preparation of α-deuterated L-amino acids using E.coli B/It7-A cells containing tryptophanase, Tetrahedron Lett. 1990, 31, pp. 7051-7054.
Furuta et al., "Evidence for a carbanion intermediate in the elimination of ammonia from L-histidine catalyzed by histidine ammonia-lyase", J. Am Chem. Soc. 1990, vol. 112, pp. 3633-3636.
Gant, "Using Deuterium in Drug Discovery: Leaving the Label in the Drug", J. Med. Chem., 2014, 57, pp. 3595-3611.

(Continued)

*Primary Examiner* — John S Kenyon
*Assistant Examiner* — Rehana Ismail
(74) *Attorney, Agent, or Firm* — Michael Best & Friedrich LLP

(57) ABSTRACT

Disclosed are a deuterated compound of formula (I), or a salt thereof, and methods for preparation thereof. The present disclosure may provide a mild, versatile organophotoredox method for the preparation of diverse, enantioenriched α-deuterated α-amino acids. In particular, the present disclosure may address the long-standing challenge of installing sterically demanding side chains into α-amino acids, including late-stage modifications on medicinal agents and natural products.

20 Claims, 2 Drawing Sheets

(56) References Cited

OTHER PUBLICATIONS

Gardner et al., "Production and Incorporation of 15N, 13C, 2H (1H-δ1 Methyl) Isoleucine into Proteins for Multidimensional NMR Studies", J. Am. Chem. Soc. 1997, vol. 119, pp. 7599-7600.
Geng et al., "Practical synthesis of C1 deuterated aldehydes enabled by NHC catalysis", Nature Catal. 2019, 2, pp. 1071-1077.
Halab et al., "Design, synthesis, and conformational analysis of azacycloalkane amino acids as conformationally constrained probes for mimicry of peptide secondary structures", Peptide Sci. 2000, 55, pp. 101-122.
Hale et al., "Stereoretentive Deuteration of a-Chiral Amines with D2O", J. Am. Chem. Soc., 2016, 138, pp. 13489-13492.
Hargrave et al., "Rhodium-catalysed conjugate addition of arylboronic acids to enantiopure dehydroamino acid derivatives", Organic and Biomolecular Chemistry, 2010, vol. 8, pp. 5120-5125.
Hopkinson et al., "Dual Catalysis Sees the Light: Combining Photoredox with Organo-, Acid, and Transition-Metal Catalysis", Chem. Eur. J. 2014, 20, pp. 3874-3886.
Huang et al., "Chemo- and Regioselective Organo-Photoredox Catalyzed Hydroformylation of Styrenes via a Radical Pathway", J. Am. Chem. Soc. 2017, 139, pp. 9799-9802.
Huang et al., "Radical Decarboxylative Functionalizations Enabled by Dual Photoredox Catalysis", ACS Catal. 2016, 6, pp. 4983-4988.
Huang et al., "Visible-Light-Promoted Nickel- and Organic-Dye-Cocatalyzed Formylation Reaction of Aryl Halides and Triflates and Vinyl Bromides with Diethoxyacetic Acid as a Formyl Equivalent", Angew. Chem. Int. Ed. 2017, 56, pp. 1500-1505.
International Preliminary Report on Patentability for Application No. PCT/US21/16599 dated Jul. 28, 2022 (5 pages).
International Search Report and Written Opinion for Application No. PCT/US21/16599 dated Apr. 16, 2021 (12 pages).
Jacques et al., "Differentiation of antiinflammatory and antitumorigenic properties of stabilized enantiomers of thalidomide analogs", Proc. Natl. Acad. Sci. U.S.A. 2015, 112, pp. E1471-1479.
Jamison et al., "Fragment Coupling with Tertiary Radicals Generated by Visible-Light Photocatalysis", Acc. Chem. Res. 2016, 49, pp. 1578-1586.
Jere et al., "Stereoretentive C-H Bond Activation in the Aqueous Phase Catalytic Hydrogenation of Amino Acids to Amino Alcohols", Org. Lett., 2003, 5, pp. 527-530.
Ji et al., "Synthesis of Enantioenriched a-Deuterated alfa-Amino Acids Enabled by an Organophotocatalytic Radical Approach", Organic Letters, 2020, vol. 22, pp. 1557-1562.
Ji et al., "Visible-Light-Mediated, Chemo- and Stereoselective Radical Process for the Synthesis of C-Glycoamino Acids", Org. Lett. 2019, 21, pp. 3086-3092.
Jin et al., "Visible-Light Photoredox Decarboxylative Couplings", Asian J. Org. Chem. 2017, 6, 368.
Karady et al., "Enantioretentive alkylation of acyclic amino acids", Tetrahedron Letters, 1984, vol. 25, pp. 4337-4340.
Koike et al., "Trifluoromethylation by Visible-Light-Driven Photoredox Catalysis", Top. Catal. 2014, 57, pp. 967-974.
Koniarczyk et al., "A General Strategy for Site-Selective Incorporation of Deuterium and Tritium into Pyridines, Diazines, and Pharmaceuticals", J. Am. Chem. Soc. 2018, 140, pp. 1990-1993.
Lastra et al., "Synthesis of compounds containing two adjacent carbon-13 labels by photolytic reactions of chromium carbene complexes", J. Am. Chem. Soc., 1993, 115, pp. 87-90.
Lian et al., "Labelling approaches for protein structural studies by solution-state and solid-state NMR", Prog. Nucl. Msgn. Reson. Spectrosc. 2001, 39, pp. 171-190.
Liang et al., "Efficient Brønsted-Acid-Catalyzed Deuteration of Arenes and Their Transformation to Functionalized Deuterated Products", Asian J. Org. Chem. 2017, 6, pp. 1063-1071.
Liu et al., "Recent advances in visible-light-driven organic reactions", Natl. Sci. Rev. 2017, 4, pp. 359-380.
Loh et al., "Photoredox-catalyzed deuteration and tritiation of pharmaceutical compounds", Science 2017, 358, pp. 1182-1187.
Lygo et al., "Enantioselective synthesis of a-carbon deuterium-labelled L-α-amino acids", Tetrahedron Lett. 2002, 43, 6677.
Maltais et al., "In Vitro and In Vivo Isotope Effects with Hepatitis C Protease Inhibitors: Enhanced Plasma Exposure of Deuterated Telaprevir versus Telaprevir in Rats", J. Med. Chem. 2009, 52, pp. 7993-8001.
Meggers, "Asymmetric catalysis activated by visible light", Chem. Commun. 2015, 51, pp. 3290-3301.
Michelotti et al., "40 Years of Hydrogen-Deuterium Exchange Adjacent to Heteroatoms: A Survey", Synthesis. 2019, 51, pp. 1319-1328.
Michelotti et al., "Development and Scale-Up of Stereoretentive α-Deuteration of Amines", Org. Process Res. Dev. 2017, 21, pp. 1741-1744.
Milne et al., "Enzymatic synthesis of a-deuterated amino acids", Biochem. Soc. Trans. 1996, 24, 133S.
Moozeh et al., "Catalytic Stereoinversion of L-Alanine to Deuterated D-Alanine", Angew. Chem., Int. Ed. 2015, 54, pp. 9381-9385.
Nagatomo et al., "Et3B-mediated two- and three-component coupling reactions via radical decarbonylation of a-alkoxyacyl tellurides: single-step construction of densely oxygenated carboskeletons", Chem. Sci. 2015, 6, pp. 2765-2769.
Narayanam et al., "Visible light photoredox catalysis: applications in organic synthesis", Chem. Soc. Rev. 2011, 40, pp. 102-113.
Oh et al., "Enantioselective synthesis of a-deuterium labelled chiral α-amino acids via dynamic kinetic resolution of racemic azlactones", Org. Biomol. Chem. 2011, 9, pp. 7983-7985.
Pirali et al., "Applications of Deuterium in Medicinal Chemistry", J. Med. Chem. 2019, 62, pp. 5276-5297.
Prier et al., "Visible Light Photoredox Catalysis with Transition Metal Complexes: Applications in Organic Synthesis", Chem. Rev. 2013, 113, pp. 5322-5363.
Puleo et al., "Catalytic a-Selective Deuteration of Styrene Derivatives", J. Am. Chem. Soc. 2019, 141, pp. 1467-1472.
Raap et al., "Synthesis of Isotopically Labelled L-Phenylalanine and L-Tyrosine", Eur. J. Org. Chem. 1999, 10, pp. 2609-2621.
Romero et al., "Organic Photoredox Catalysis", Chem. Rev., 2016, vol. 116, pp. 10075-10166.
Rose et al., "Mechanisms and stereochemistry of the activation of (2S)- and (2R)-serine O-sulfate as suicide inhibitors for *Escherichia coli* glutamic acid decarboxylase", J. Chem. Soc. Chem. Commun. 1992, pp. 1784-1786.
Rose et al., "Stereospecific synthesis of a-deuteriated α-amino acids: regiospecific deuteriation of chiral 3-isopropyl-2,5-dimethoxy-3,6-dihydropyrazines", J. Chem. Soc. Perkin Trans. 1995, pp. 157-165.
Rossolini et al., "Photocatalytic Three-Component Umpolung Synthesis of 1,3-Diaminese", Org. Lett. 2018, 20, pp. 6794-6798.
Sack et al., "Solid-State NMR Determination of Peptide Torsion Angles: Applications of 2H-Dephased Redor", J. Am. Chem. Soc. 2000, 122, pp. 12263-12269.
Sajiki et al., "Palladium-Catalyzed Base-Selective H-D Exchange Reaction of Nucleosides in Deuterium Oxide", Synlett. 2005, No. 9, pp. 1385-1388.
Sattler et al., "Hydrogen/Deuterium (H/D) Exchange Catalysis in Alkanes", ACS Catal. 2018, 8, pp. 2296-2312.
Shen et al., "Trideuteromethylation Enabled by a Sulfoxonium Metathesis Reaction", Org. Lett. 2019, 21, p. 448-452.
Sibi et al., "Enantioselective Hydrogen Atom Transfer Reactions: Synthesis of N-Acyl-alpha-Amino Acid Esters", Supported by the National Institutes of Health (NIH-GM-54656), Angew. Chem., Int. Ed. 2001, 40, pp. 1293-1296.
Sim et al., "Synthesis of a-Fluoro-α-amino Acid Derivatives via Photoredox-Catalyzed Carbofluorination", ACS. Catal. 2019, 9, pp. 1558-1563.
Simmons et al., "On the interpretation of deuterium kinetic isotope effects in C-H bond functionalizations by transition-metal complexes", Angew. Chem., Int. Ed. 2012, 51, pp. 3066-3072.
Skubi et al., "Dual Catalysis Strategies in Photochemical Synthesis", Chem. Rev. 2016, 116, pp. 10035-10074.
Stevenson et al., "Structural and stereochemical studies of methiomine decarboxylase from dryopteris felix-mas", Tetrahedron Lett., 1986, 27, pp. 5661-5664.

(56) References Cited

OTHER PUBLICATIONS

Taglang et al., "Enantiospecific C-H Activation Using Ruthenium Nanocatalysts", Angew. Chem., Int. Ed. 2015, 54, pp. 10474-10477.
Taglang et al., "Late-stage deuteration of 13C-enriched substrates for T1 prolongation in hyperpolarized 13C Mri", Chem. Commun. 2018, 54, 5233.
Takeda et al., "Asymmetric synthesis of α-deuterated α-amino acids", Org. Biomol. Chem. 2017, 15, pp. 6978-6983.
Taylor et al., "An improved synthesis of deuterated Schöllkopf's bis-lactim ether and its use for the asymmetric synthesis of (R)-[α-2H]-phenylalanine methyl esters", Tetrahedron: Asymmetry. 2006, 17, pp. 1170-1178.
Tellis et al., "Single-Electron Transmetalation via Photoredox/Nickel Dual Catalysis: Unlocking a New Paradigm for sp3-sp2 Cross-Coupling", Acc. Chem. Res. 2016, 49, pp. 1429-1439.
Valero et al., "Highly Selective Directed Iridium-Catalyzed Hydrogen Isotope Exchange Reactions of Aliphatic Amides", Angew. Chem., Int. Ed. 2018, 57, pp. 8159-8163.
Wang et al., "General and Practical Potassium Methoxide/Disilane-Mediated Dehalogenative Deuteration of (Hetero)Arylhalides", J. Am. Chem. Soc. 2018, 140, pp. 10970-10974.
Wang et al., "Photoredox Catalysis for Building C-C Bonds from C(sp2)-H Bonds", Chem. Rev. 2018, 118, pp. 7532-7585.
Wong et al., "Enzyme-catalyzed organic synthesis: regeneration of deuterated nicotinamide cofactors for use in large-scale enzymatic synthesis of deuterated substances", J. Am. Chem. Soc. 1983, 105, pp. 5012-5014.
Xuan et al., "Visible-Light-Induced Decarboxylative Functionalization of Carboxylic Acids and Their Derivatives", Angew. Chem., Int. Ed. 2015, 54, pp. 15632-15641.
Yamamoto et al., "Synthesis and configurational stability of (S)- and (R)-deuteriothalidomides", Chem. Pharm. Bull. 2010, 58, pp. 110-112.
Yan et al. "Radicals: Reactive Intermediates with Translational Potential", J. Am. Chem. Soc. 2016, 138, pp. 12692-12714.
Yang, "Deuterium: Discovery and Applications in Organic Chemistry", Elsevier, Amsterdam, 2016, Table of Contents, 2 pages.
Yu et al., "Iron-catalysed tritiation of pharmaceuticals", Nature, 2016, 529, pp. 195-199.
Zhou et al., "Visible-light-mediated deuteration of silanes with deuterium oxide", Chem. Sci. 2019, 10, pp. 7340-7344.

\* cited by examiner

Synthesis of α-deuterated amino acids by photoredox catalysis (This Work)

- distinct radical bond connection approach
- metal free photoredox catalysis
- ubiquitous radical precursor - carboxylic acids
- broad substrate scope
- highly stereoselective deuteration
- late-stage functionalization

METHODS FOR PRACTICAL SYNTHESIS OF DEUTERATED AMINO ACIDS

CROSS-REFERENCE TO RELATED APPLICATION(S)

This application is a U.S. national stage entry of International Patent Application No. PCT/US2021/016599, filed on Feb. 4, 2021, which claims the benefit of and priority to U.S. Provisional Patent Application No. 62/970,838, filed on Feb. 6, 2020, and U.S. Provisional Patent Application No. 62/978,175, filed on Feb. 18, 2020, the entire contents of all of which are hereby incorporated by reference.

STATEMENT OF GOVERNMENT INTEREST

This invention was made with government support under Grant No. GM125920, awarded by National Institutes of Health. The government has certain rights in the invention.

BACKGROUND

Isotopically labelled amino acids, particularly, the α-deuterated version, are broadly used in almost every sub-discipline in the life sciences for studying biosynthetic pathways, enzymatic mechanisms, and probing the secondary and tertiary structures of peptides and proteins by NMR and MS techniques. Furthermore, the incorporation of deuterium into α-position of amino acids can enhance metabolic stability and reduce the rate of epimerization of peptido and peptidomimetic therapeutics and thus enhance the efficacy and/or decrease the potential toxicity (e.g., $d_1$-telaprevir (suppressing epimerization), d-pomalidomide (slowing down racemization), and L-d-dopa (enhancing stability toward monoamine oxidases). Thus, there is a long-standing interest in the synthesis and application of enantioenriched α-deuterated amino acids.

In the routes available for the synthesis of chiral α-deuterated amino acids, enzyme-catalyzed approaches including enzyme mediated deuteration of α-amino acids and enzymatic reductive amination of pyruvates, are largely limited by narrow substrate scope. The commonly used methods with the capacity of access to unnatural α-amino acids rely on asymmetric alkylation of deuterated glycine derived imines or H/D exchange of amino acids derived imines using chiral auxiliary (e.g., Schöllkopf's bis-lactam ether) or chiral promoter catalyzed enolization (FIG. 1A). Transitional metal-catalyzed C—H activation followed by H/D exchange or 1,3-deuteride transfer provides an alternative to incorporate the isotope into α-position of amino acids (FIG. 1A). Although these techniques represent the state-of-the-art strategies for the synthesis of α-deuterated amino acids, they all rely on a polar bond connection, and therefore carrying inherent limitations such as poor chemo-, regio- and/or enantio-selectivity, and in many cases, moderate level of deuteration. Furthermore, an intrinsic limitation of these ionic strategies is difficult to synthesize highly sterically demanding amino acids, a class of structures widely used in the field of peptides and peptidomimetics to constrain their conformations, and thus improve their potency and/or selectivity, lipophilicity, and metabolic stability. Thus, there remains a need for improved synthesis methods for preparing deuterated amino acids, particularly those with high yield, high deuteration level, and high chemo-, regio- and/or enantio-selectivity.

SUMMARY OF THE INVENTION

In one aspect, the present disclosure provides a method for preparing deuterated compound of formula (I), or a salt thereof,

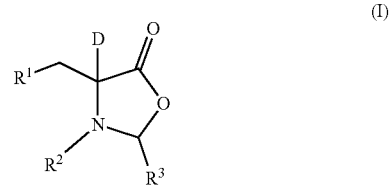

(I)

wherein
$R^1$ is alkyl, —C(O)alkyl, alkenyl, —C(O)alkyenyl, cycloalkyl, —C(O)cycloalkyl, cycloalkenyl, —C(O)cycloalkenyl, aryl, —C(O)aryl, heteroaryl, —C(O)heteroaryl, heterocyclyl, or —C(O)heterocyclyl, wherein $R^1$ is optionally substituted with one or more $R^a$;
$R^2$ is H or an amino protecting group;
$R^3$ is —$CR^b R^c R^d$;
$R^a$ at each occurrence is independently halogen, —CN, —OH, nitro, a protected hydroxyl, a protected amino, or —X—$R^X$, wherein X is bond, O, NH, C(O), OC(O), or C(O)NH; and $R^X$ is alkyl, alkenyl, alkynyl, alkoxy, cycloalkyl, aryl, heteroaryl, or heterocyclyl, wherein the $R^X$ is optionally substituted;
$R^b$, $R^c$, and $R^d$ are independently H, alkyl, or $R^b$ and $R^c$ together with the carbon they are attached to form a ring;
the method comprising:
(i) mixing $R^1$—COOD with a compound of formula (II), a base, and a photocatalyst in an essentially $H_2O$ free solvent comprising $D_2O$ and an organic solvent to form a mixture; and

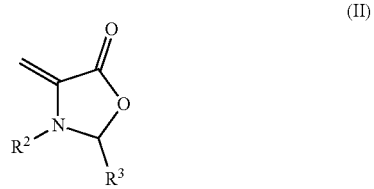

(II)

(ii) exposing the mixture of (i) to light, thereby producing the deuterated compound of formula (I), or a salt thereof.

In another aspect, the present disclosure provides a deuterated compound of formula (I), or a salt thereof,

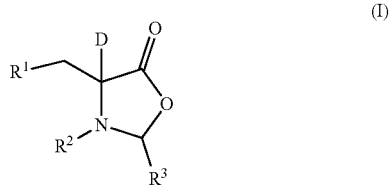

(I)

wherein
$R^1$ is alkyl, —C(O)alkyl, alkenyl, —C(O)alkyenyl, cycloalkyl, —C(O)cycloalkyl, cycloalkenyl, —C(O)

cycloalkenyl, aryl, —C(O)aryl, heteroaryl, —C(O)heteroaryl, heterocyclyl, or —C(O)heterocyclyl, wherein $R^1$ is optionally substituted with one or more $R^a$;

$R^2$ is H or an amino protecting group;

$R^3$ is —$CR^bR^cR^d$;

$R^a$ at each occurrence is independently halogen, —CN, —OH, nitro, a protected hydroxyl, a protected amino, or —X—$R^X$, wherein X is bond, O, NH, C(O), OC(O), or C(O)NH; and $R^X$ is alkyl, alkenyl, alkynyl, alkoxy, cycloalkyl, aryl, heteroaryl, or heterocyclyl, wherein the $R^X$ is optionally substituted;

$R^b$, $R^c$, and $R^d$ are independently H, alkyl, or $R^b$ and $R^c$ together with the carbon they are attached to form a ring.

In another aspect, the present disclosure provides method of preparing a deuterated amino acid, comprising
preparing a deuterated compound of formula (I), or a salt thereof, according to method as disclosed herein; and
converting the deuterated compound of formula (I), or a salt thereof, to an amino acid having a structure of formula (III), or a salt thereof,

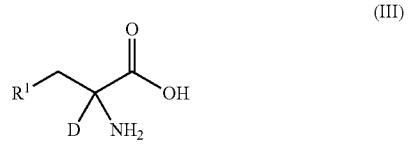

(III)

wherein $R^1$ is as defined in formula (I).

BRIEF DESCRIPTION OF THE DRAWINGS

FIG. 1A shows known methods for enolate engaged alkylation and deuteration. FIG. 1B shows a representative synthesis of α-deuterated amino acids by photoredox catalysis as disclosed herein.

DETAILED DESCRIPTION

Figure 1A:
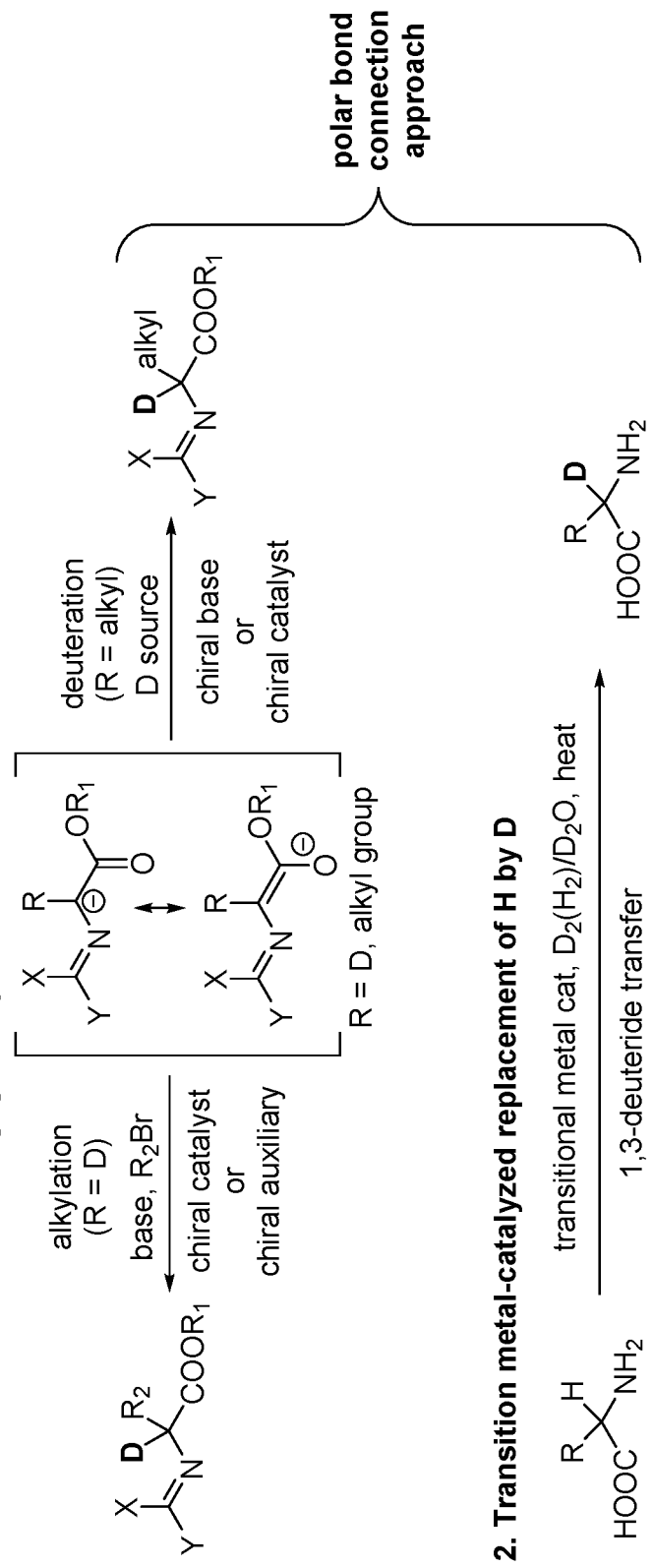
FIGS. 1A-1B show different methods for the synthesis of enantioenriched α-deuterated amino acids.

The present relates to organocatalytic strategy that enables directly converting readily accessible aldehydes to their 1-deutero counterparts using $D_2O$ as the deuterium pool. The approach, distinct from the reported transition metal catalyzed ionic hydrogen-deuterium exchange (HDE) processes, employs a photoredox radical activation mode. The methods described herein may be useful for not only aromatic aldehydes, but also aliphatic substrates, which have been difficult for HDE. The present methods also may be useful for selective late-stage deuterium incorporation into complex structures with uniformly high deuterium level (>90%).

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 20 carbon atoms. The term "lower alkyl" or "$C_{1-6}$alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH₂CH₂—, —CH₂CH₂CH₂—, —CH₂CH₂CH₂CH₂—, and —CH₂CH₂CH₂CH₂CH₂—.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "haloalkyl" as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "cycloalkyl" as used herein, means a monovalent group derived from an all-carbon ring system containing zero heteroatoms as ring atoms, and zero double bonds. The all-carbon ring system can be a monocyclic, bicylic, or tricyclic ring system, and can be a fused ring system, a bridged ring system, or a spiro ring system, or combinations thereof. Examples of cycloalkyls include, but are not limited to, cyclopropyl, cyclobutyl, cyclopentyl, cyclohexyl, cycloheptyl, cyclooctyl, and

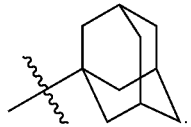 [SMILES: *C12CC3CC(CC(C3)C1)C2]

The cycloalkyl groups described herein can be appended to the parent molecular moiety through any substitutable carbon atom.

The term "cycloalkenyl" as used herein, means anonaromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "halogen" as used herein, means Cl, Br, I, or F.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O, and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

The hydroxyl, amino, or carboxyl group as disclosed herein may be protected by a protecting group. The term "protecting group" refers to a moiety that prevents chemical reactions from occurring on a heteroatom (such as, N, O, or S) to which that protecting group is attached. The protected groups may be de-protected to provide, for example, a —OH, —NH$_2$, or —C(O)OH group. The term "protected amino," "protected hydroxyl," or "protected carboxyl" means a group resulting from the attachment of a suitable protecting group to an amino, a hydroxyl, or acarboxyl group, respectively. The term "amino protecting group," "hydroxyl protecting group," or "carboxyl protecting group" refers to a group suitable for protecting an amino, a hydroxyl, or a carboxyl, respectively. Various protecting groups are well known in the art and include those described in detail in Greene's Protective Groups in Organic Synthesis, T. W. Greene and P. G. M. Wuts, 5$^{th}$ edition, John Wiley & Sons, 2014, the entirety of which is incorporated herein by reference. For example, suitable amino protecting groups include, but are not limited to, carbobenzyloxy (Cbz); t-butyloxycarbonyl (Boc); 9-fluorenylmethyloxycarbonyl (Fmoc), 2,2,2-trichloroethyloxycarbonyl (Troc), and allyloxycarbonyl (Alloc). In each of the foregoing, the —NH— represents the nitrogen from the amino group that is being protected. Suitable hydroxyl protecting groups include, but are not limited to, methoxymethyl ether (MOM), tetrahydropyranyl ether (THP), t-butyl ether, allyl ether, benzyl ether, trimethylsilyl (TMS), t-butyldimethylsilyl (TBDMS), acetyl, benzoyl, and pivalic acid ester. Suitable carboxyl protecting groups include, but are not limited to, methyl ester, t-butyl ester, and benzyl ester In some instances, the number of carbon atoms in a hydrocarbyl substituent (e.g., alkyl or cycloalkyl) is indicated by the prefix "C$_{x-y}$" or "C$_x$-C$_y$-", wherein x is the minimum and y is the maximum number of carbon atoms in the substituent. Thus, for example, "C$_{1-4}$alkyl" or "C$_1$-C$_4$-alkyl" refers to an alkyl substituent containing from 1 to 4 carbon atoms.

The molecules and substituent groups as described herein are not deuterated, unless explicitly indicated otherwise. The term "deuterated" as used herein refers to a molecule or substituent group in which 1, 2, 3, 4, 5, 6, 7, or 8 hydrogen atoms are replaced by deuterium.

The term "level of deuterium incorporation" as used herein refers to the extent of deuterium labeling as determined by $^1$H NMR spectroscopy, and is measured by percentage deuteration as shown in Equation 1.

$$\% \text{ Deuteration} = 100 - \left| \left( \frac{\text{residual integral}}{\text{number of labelling sites}} \right) \times 100 \right| \quad \text{Equation 1}$$

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUND

The present disclosure provides a deuterated compound of formula (I), or a salt thereof,

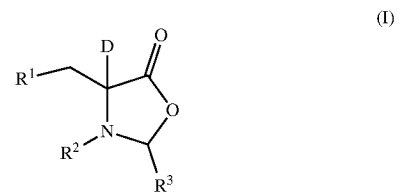

wherein
R$^1$ is alkyl, —C(O)alkyl, alkenyl, —C(O)alkyenyl, cycloalkyl, —C(O)cycloalkyl, cycloalkenyl, —C(O)cycloalkenyl, aryl, —C(O)aryl, heteroaryl, —C(O)heteroaryl, heterocyclyl, or —C(O)heterocyclyl, wherein R$^1$ is optionally substituted with one or more R$^a$;
R$^2$ is H or an amino protecting group;
R$^3$ is —CR$^b$R$^c$R$^d$;
R$^a$ at each occurrence is independently halogen, —CN, —OH, nitro, a protected hydroxyl, a protected amino, or —X—R$^X$, wherein X is bond, O, NH, C(O), OC(O), or C(O)NH; and R$^X$ is alkyl, alkenyl, alkynyl, alkoxy, cycloalkyl, aryl, heteroaryl, or heterocyclyl, wherein the R$^X$ is optionally substituted;
R$^b$, R$^c$, and R$^d$ are independently H, alkyl, or R$^b$ and R$^c$ together with the carbon they are attached to form a ring.

In some embodiments, R$^1$ is an optionally substituted alkyl, an optionally substituted cycloalkyl, an optionally substituted heteroaryl, or an optionally substituted heterocyclyl.

In some embodiments, the R$^2$ is an amino protecting group, such as carbobenzyloxy (Cbz), butyloxycarbonyl (Boc); 9-fluorenylmethyloxycarbonyl (Fmoc), 2,2,2-trichloroethyloxycarbonyl (Troc), or allyloxycarbonyl (Alloc). In some embodiments, R$^2$ is carbobenzyloxy (Cbz).

In some embodiments, R$^3$ is a group providing steric hindrance. In some embodiments, R$^b$, R$^c$, and R$^d$ are each independently C$_{1-4}$alkyl. In some embodiments, R$^d$ is H or C$_{1-4}$alkyl and R$^b$ and R$^c$ together with the carbon they are attached to form a ring. The ring may be a 5- to 12-membered cycloalkyl, 5- to 12-membered cycloalkenyl, 5- to 12-membered heteroaryl, or 5- to 12-membered heterocyclyl, which may be optionally substituted. In some embodiments, R$^3$ is t-butyl The compounds of formula (I) may include stereoisomers. In some embodiments, a compound of formula (I) is an enantioenriched compound or an enantiomer compound. In some embodiments, the deuterated compound of formula (I) has a structure of formula (I-a), or a salt thereof (I-a)
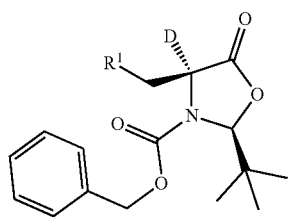
in which R¹ is as defined in formula (I).
In some embodiments, the deuterated compound of formula (I) is selected from the group consisting of
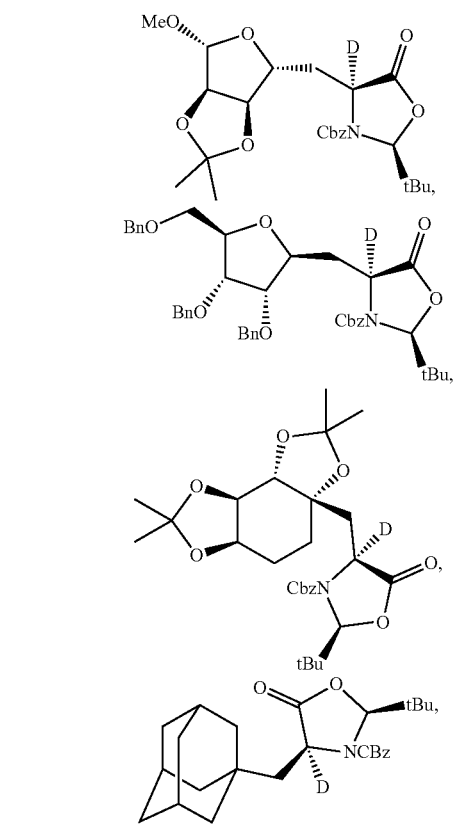
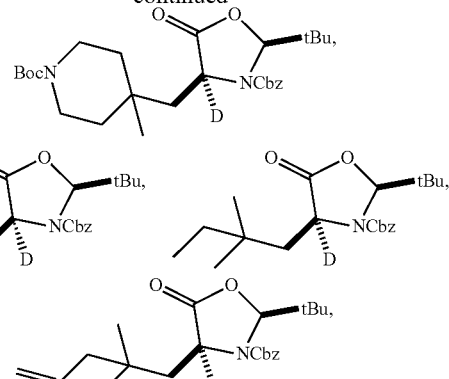
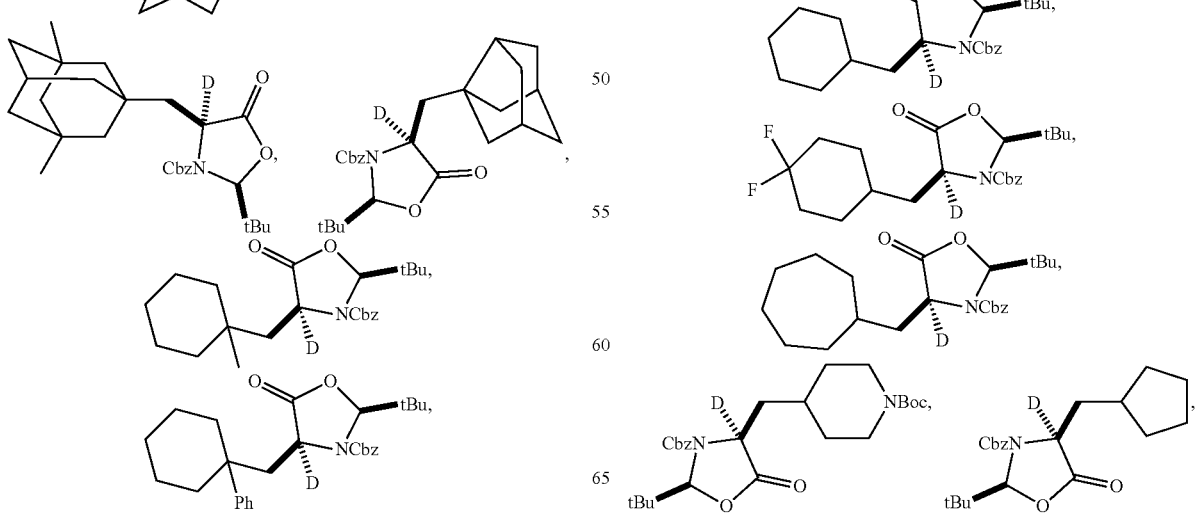

-continued

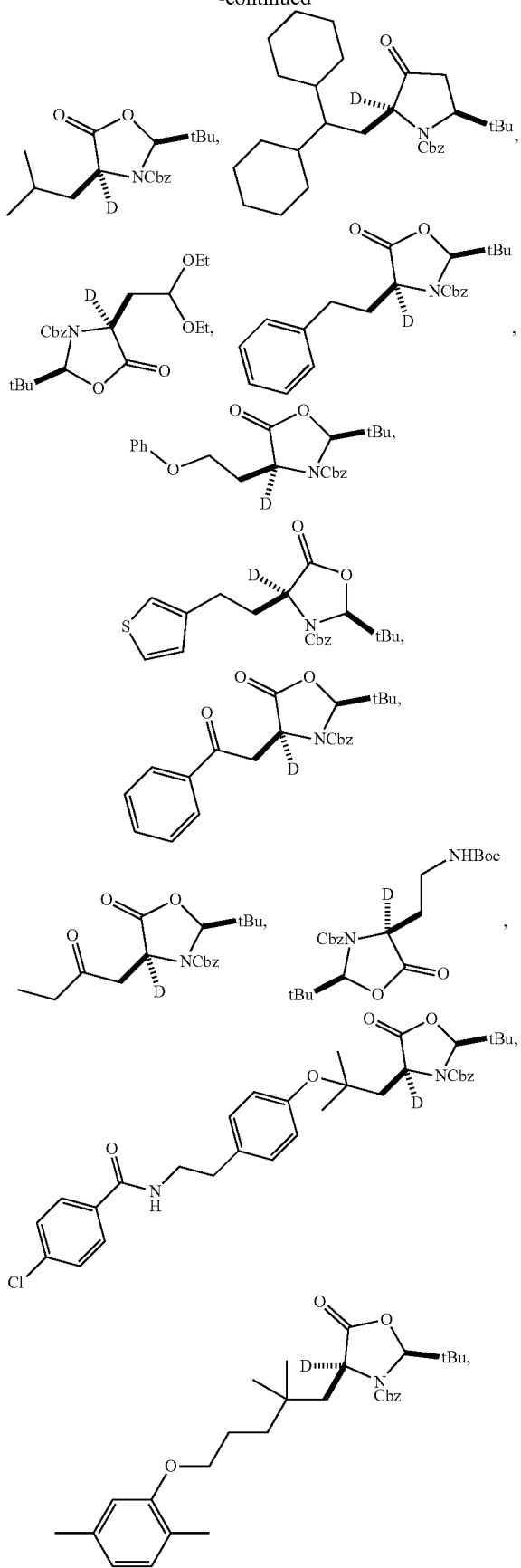

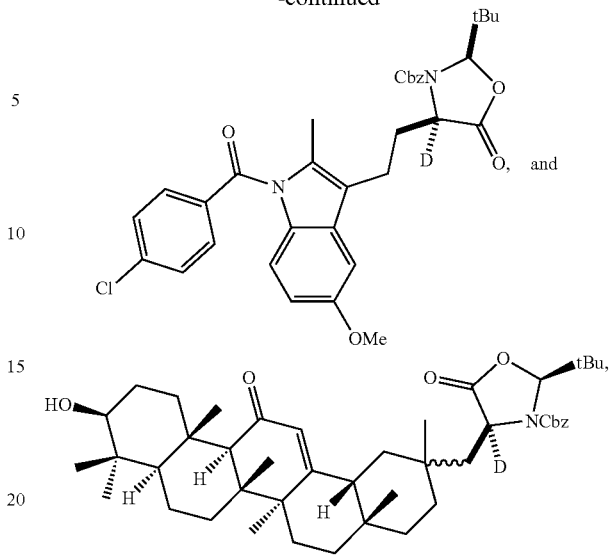

or a salt thereof.

3. METHOD

The present disclosure relates to a mild, versatile organophotoredox method for the preparation of diverse, enantioenriched α-deuterated α-amino acids. Distinct from the well-established two-electron transformations, a radical-based strategy as disclosed herein may offer the unrivaled capacity of the convergent unification of readily accessible feedstock carboxylic acids and a chiral methyleneoxazolidinone fragment and highly diastereo-, chemo- and regioselective incorporation of deuterium simultaneously. Furthermore, the present approach may address the long-standing challenge of the installation of sterically demanding side chains into α-amino acids.

Figure 1B:
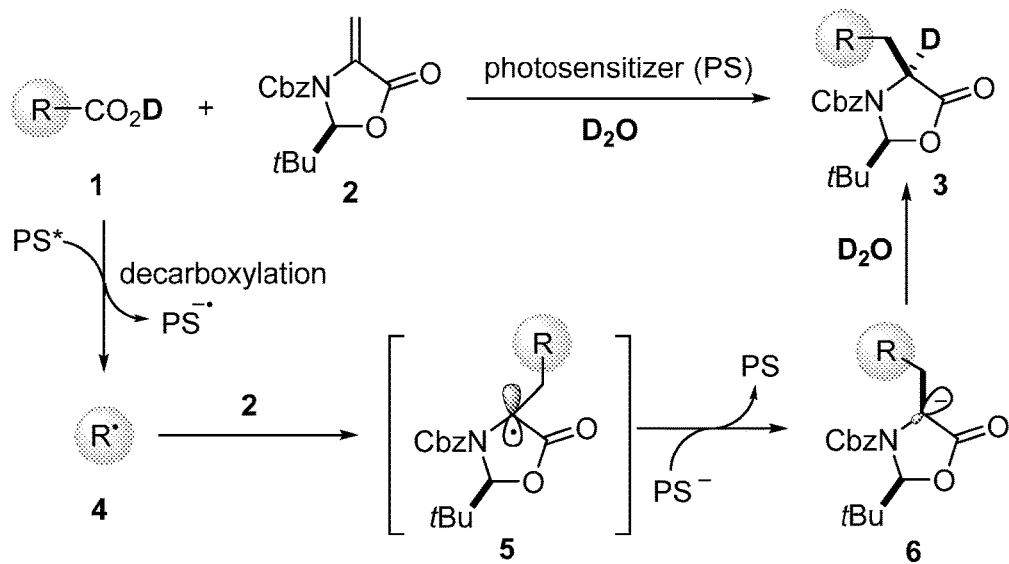

An open shell radical process may offer a distinct and pragmatic approach for introducing the bulky groups into amino acids by virtue of favorable formation of 3° radicals. The radical addition to dehydroalanine (Dha) derivatives has been demonstrated as a viable approach for the synthesis of α-amino acids. In recent efforts, notably, an efficient Giese-type reaction of tertiary amines or halogenated pyridine with Dha derivatives is realized with photoredox catalysis. Previously, fluorine was introduced at the α-position of amino acids by regioselective carbofluorination of Dha compounds using alkyl trifluoroborate reagents as radical precursors. Thus, the present disclosure may provide a direct addition of a decarboxylative radical 4 to Dha derivatives such as (S)-methyleneoxazolidinone 2 as a chiral inducer, which may lead to enantioenriched amino acids 3, by the employment of ubiquitous, readily accessible carboxylic acids 1 as radical progenitors (FIG. 1B). The ready accessibility of feedstock carboxylic acids 1 may enable the synthesis of more structurally diverse amino acids. Furthermore, Re-face selective deuteration of the chiral anion intermediate 6 of the present disclosure may provide a novel approach to enantioenriched α-deuterated amino acids 3. In particular embodiments, the present method may provide chemo-, regio- and diastereo-selective incorporation of bulky side chains and deuterium into α-amino acids simultaneously.

In one aspect, the present disclosure provides a method for preparing a deuterated compound of formula (I), or a salt thereof,

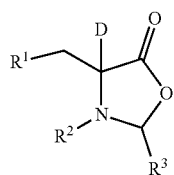

wherein
R¹ is alkyl, —C(O)alkyl, alkenyl, —C(O)alkyenyl, cycloalkyl, —C(O)cycloalkyl, cycloalkenyl, —C(O)cycloalkenyl, aryl, —C(O)aryl, heteroaryl, —C(O)heteroaryl, heterocyclyl, or —C(O)heterocyclyl, wherein R¹ is optionally substituted with one or more R$^a$;
R² is H or an amino protecting group;
R³ is —CR$^b$R$^c$R$^d$;
R$^a$ at each occurrence is independently halogen, —CN, —OH, nitro, a protected hydroxyl, a protected amino, or —X—R$^X$, wherein X is bond, O, NH, C(O), OC(O), or C(O)NH; and R$^X$ is alkyl, alkenyl, alkynyl, alkoxy, cycloalkyl, aryl, heteroaryl, or heterocyclyl, wherein the R$^X$ is optionally substituted;
R$^b$, R$^c$, and R$^d$ are independently H, alkyl, or R$^b$ and R$^c$ together with the carbon they are attached to form a ring;

the method comprising:
(i) mixing R¹—COOD with a compound of formula (II), a base, and a photocatalyst in an essentially H₂O free solvent comprising D₂O and an organic solvent to form a mixture; and

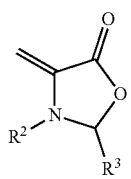

(ii) exposing the mixture of (i) to light, thereby producing the deuterated compound of formula (I), or a salt thereof.

In some embodiments, R¹ is an optionally substituted alkyl, an optionally substituted cycloalkyl, an optionally substituted heteroaryl, or an optionally substituted heterocyclyl.

In some embodiments, R¹ is

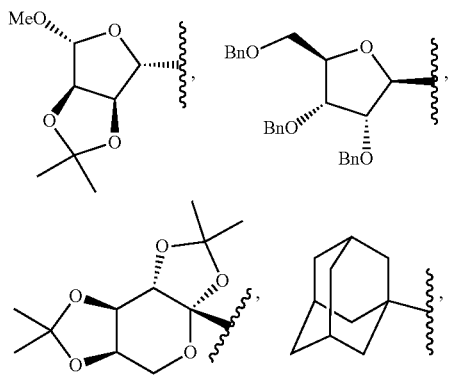

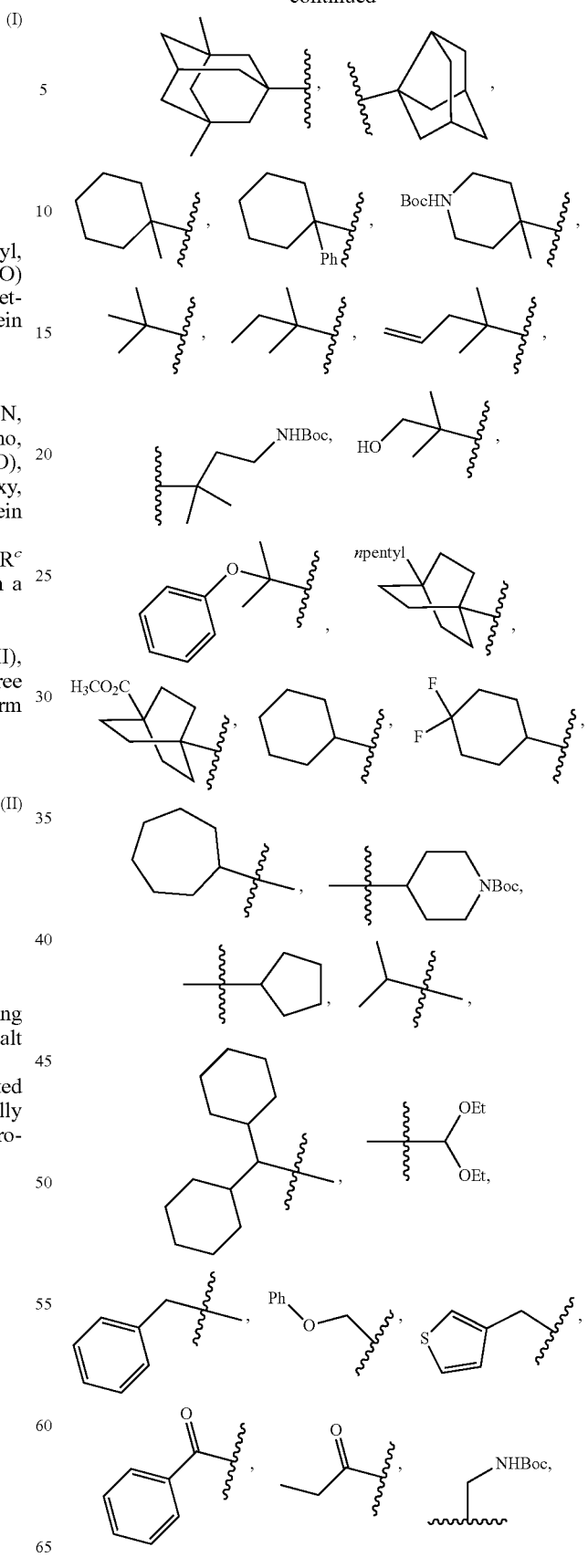

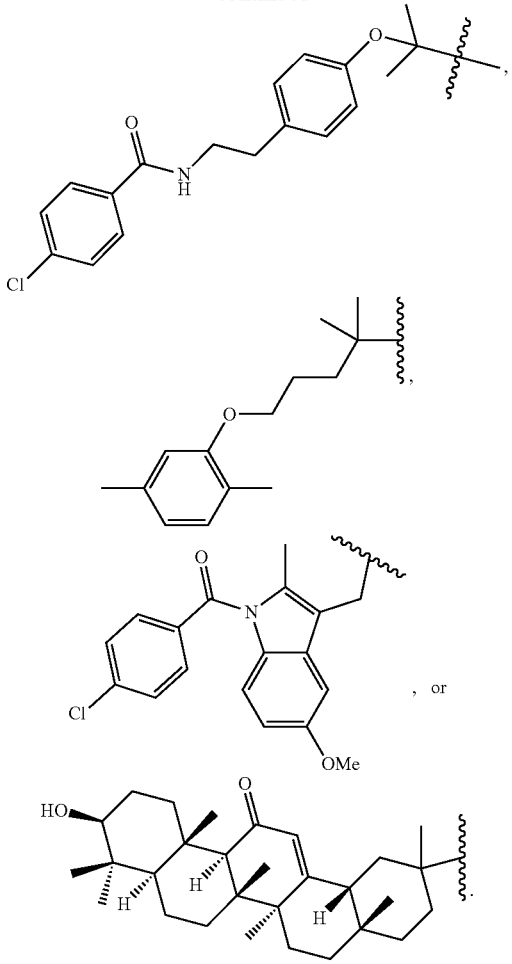

In some embodiments, the R² is an amino protecting group, such as carbobenzyloxy (Cbz), butyloxycarbonyl (Boc), 9-fluorenylmethyloxycarbonyl (Fmoc), 2,2,2-trichloroethyloxycarbonyl (Troc), or allyloxycarbonyl (Alloc). In some embodiments, R² is carbobenzyloxy (Cbz).

In some embodiments, R³ is a group providing steric hindrance. In some embodiments, $R^b$, $R^c$, and $R^d$ are each independently $C_{1-4}$alkyl. In some embodiments, $R^d$ is H or $C_{1-4}$alkyl and $R^b$ and $R^c$ together with the carbon they are attached to form a ring. The ring may be a 5- to 12-membered cycloalkyl, 5- to 12-membered cycloalkenyl, 5- to 12-membered heteroaryl, or 5- to 12-membered heterocyclyl, which may be optionally substituted. In some embodiments, R³ is t-butyl.

In some embodiments, the compound of formula (II) has a structure of formula (II-a).

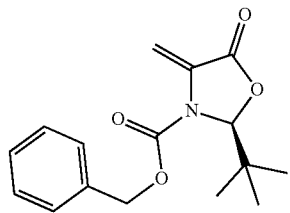

(II-a)

The photocatalyst may be any suitable agent that produces an excited state upon irradiate (e.g. by visible light), which in turn catalyzes the formation of a radical from another molecule. Suitable photocatalysts include organic photoredox catalysts and photosensitizers known in the art. For example, the photocatalyst may include mesityl acridinium salt (Mes-Acr-Me⁺·ClO₄⁻) or carbazole compounds, such as 2,4,5,6-tetra(9H-carbazol-9-yl)isophthalonitrile (4CzIPN), or derivatives thereof. In some embodiments, the photocatalyst is Mes-Acr-Me⁺·ClO₄⁻, or 4CzIPN, or a combination thereof.

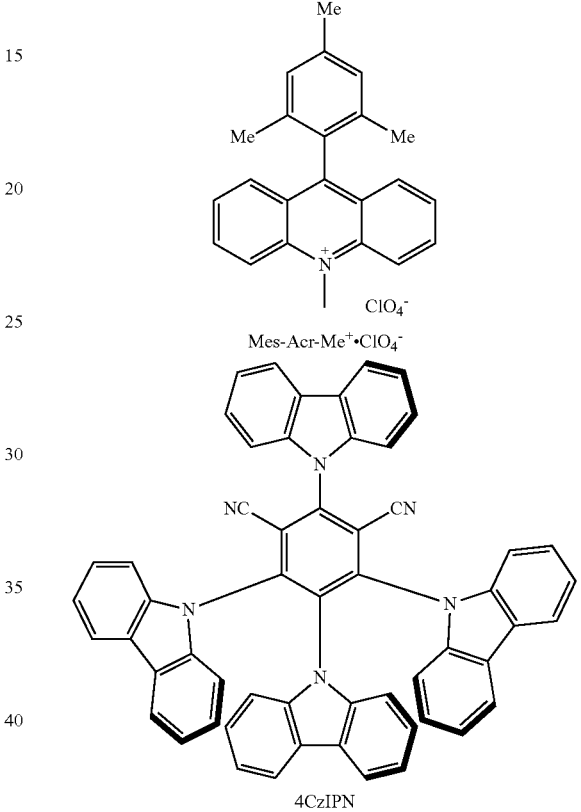

The essentially H₂O free solvent as described herein refers to a solvent that is virtually free of water in the form of H₂O. The essentially H₂O free solvent may include less than 0.10% by weight H₂O, such as less than 0.01%, less than 0.001%, less than 0.0001%, or less than 0.00001% by weight H₂O. In some embodiments, the solvent is free of H₂O. In some embodiments, the essentially H₂O free solvent is a combination of D₂O and an anhydrous organic solvent. In some embodiments, the organic solvent is acetonitrile, dimethylformamide, dichloroethane, or a combination thereof. The anhydrous organic solvent may be prepared by known techniques.

In some embodiments, the base is 1,8-diazabicyclo[5.4.0]undec-7-ene (DBU), Cs₂CO₃, or a combination thereof.

In some embodiments, the method further comprises carrying out the mixing step (i) and/or the exposing to light step (ii) under an inert gas. In some embodiments the inert gas comprises nitrogen (N2).

In some embodiments, the photocatalyst is Mes-Acr-Me⁺·ClO₄⁻, the base is DBU, and the organic solvent is acetonitrile. In some embodiments, the photocatalyst is 4CzIPN, the base is Cs₂CO₃, and the organic solvent is dimethylformamide.

In some embodiments, the present method may produce an enantioenriched compound or an enantiomer compound, such as a compound of formula (I-a), or its enantiomers, or a salt thereof,

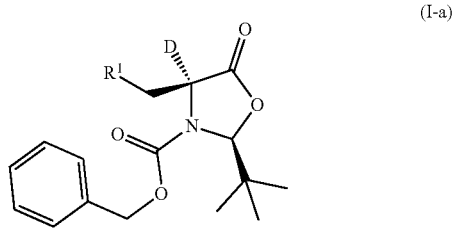

(I-a)

in which $R^1$ is as defined in formula (I).

In some embodiments, the method disclosed herein further includes isolating the produced deuterated compound of formula (I), or a salt thereof. Suitable method for isolating the deuterated product may include those known in the art, such as chromatographic procedures.

In some embodiments, the method disclosed herein produces a compound of formula (I), or a salt thereof, having a level of deuterium incorporation of at least 80% or at least 90%. The level of deuterium incorporation of the compound of formula (I), or a salt thereof, may be at least 91%, at least 92%, at least 93%, at least 94%, at least 95%, at least 96%, at least 97%, at least 98%, at least 99%, or even at least 99.5%. The level of deuterium incorporation of the compound of formula (I), or a salt thereof, may be about 90% to 99.9%, about 92% to 99.9%, about 95% to 99.9%, about 97% to 99.9%, or even about 99% to 99.9%. In particular embodiments, the level of deuterium incorporation of the compound of formula (I), or a salt thereof, is at least 95%.

In another aspect, the present disclosure provides a deuterated compound of formula (I), or a salt thereof, produced by the method disclosed herein.

In another aspect, the present disclosure provides an isolated deuterated compound of formula (I), or a salt thereof, produced by the method disclosed herein.

The deuterated compounds of formula (I), or a salt thereof, as disclosed herein may be used as a starting materials for the preparation of other compounds, including, for example, deuterated amino acids.

In another aspect, the present disclosure provides a method of preparing a deuterated amino acid, comprising
preparing a deuterated compound of formula (I), or a salt thereof, according to method as disclosed herein; and
converting the deuterated compound of formula (I), or a salt thereof, to an amino acid having a structure of formula (III), or a salt thereof,

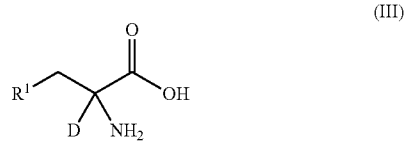

(III)

wherein $R^1$ is as defined in formula (I).

In some embodiments, the converting step comprises contact the compound of formula (I), or a salt therefor, with an acid. The acid may be, for example, hydrochloric acid, sulfuric acid, phosphoric acid, acetic acid, trifluoroacetic acid, or combinations thereof. In some embodiments, the acid comprises concentrated hydrochloric acid (conc. HCl).

In some embodiments, a deuterated compound of formula (I-a), or a salt thereof, as disclosed herein is used to produce a deuterated amino acid product. In some embodiments, the deuterated amino acid produced by the method disclosed herein has a structure of formula (III-a), or a salt thereof

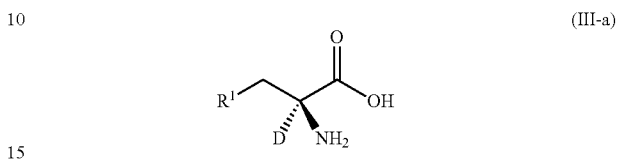

(III-a)

wherein $R^1$ is as defined in formula (I).

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

3. EXAMPLES

General Information. Commercially available reagents were purchased from Sigma Aldrich, Matrix Chemical, AKSci, Alfa Aesar, TCI, and Adamas-beta, and used as received unless otherwise noted. Except Ir(ppy)$_3$ purchased form Adamas-beta, photosensitizers including 4CzIPN, Ir[dF(CF$_3$)]$_2$(dtbpy)PF$_6$, are prepared according to corresponding literatures. Merck 60 silica gel was used for chromatography, and Whatman silica gel plates with a fluorescence F254 indicator were used for thin-layer chromatography (TLC) analysis. $^1$H and $^{13}$C NMR spectra were recorded on Bruker Advance 400 Hz. Chemical shifts in $^1$H NMR spectra are reported in parts per million (ppm) relative to residual chloroform (7.26 ppm) or dimethyl sulfoxide (2.50 ppm) as internal standards. $^1$H NMR data are reported as follows: chemical shift, multiplicity (s=singlet, d=doublet, m=multiplet), coupling constant in Hertz (Hz) and hydrogen numbers based on integration intensities. $^{13}$C NMR chemical shifts are reported in ppm relative to the central peak of CDCl$_3$ (77.16 ppm) or (CD$_3$)$_2$SO (39.52 ppm) as internal standards. Cyclic voltammetry was performed at 25° C. on a CH Instrument CHI604xD electrochemical analyzer using a glassy carbon working electrode, a platinum wire counter electrode, and the Ag/AgCl reference electrode calibrated using ferrocene redox couple (4.8 eV below vacuum). Acetonitrile was degassed by the freeze-pump-thaw method and used within one week.

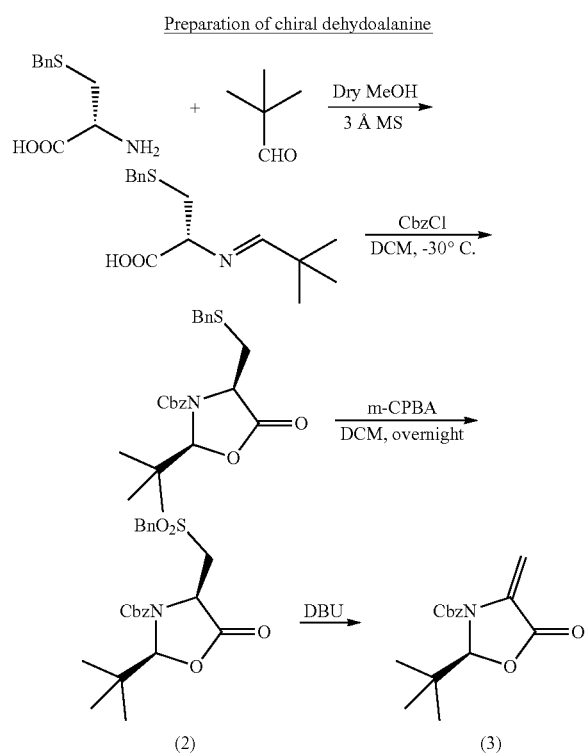

(2)  (3)

Chiral Dehydroalanine Synthesis

Benzyl (2S,4R)-4-((benzylthio)methyl)-2-(tert-butyl)-5-oxooxazolidine-3-carboxylate (1). To a round bottom flask equipped with a stir bar was added S-benzyl-L-cysteine (5 g, 23.5 mmol, 1 equiv.), NaOH (0.9 g, 23.5 mmol, 0.95 equiv), and anhydrous MeOH (250 mL). The reaction was stirred at room temperature for 30 minutes. Trimethylacetaldehyde (3.09 ml, 28.5 mmol, 1.2 equiv) and activated 3 Å molecular sieves (25 g) were added to the reaction flask, each in one portion. The reaction was placed under nitrogen atmosphere and stirred at room temperature until the starting material had been consumed (determined by $^1$H NMR of a filtered and concentrated aliquot of the reaction solution dissolved in CD$_3$OD). The reaction was quickly filtered through celite and concentrated by rotary evaporation. The residue was dried under high vacuum for 24 hours to afford the imine as a white solid. The imine was dissolved in anhydrous DCM (250 mL) and cooled to −30° C. Benzyl chloroformate (5.05 mL, 35.5 mmol, 1.5 equiv) was added to the reaction dropwise via syringe. The reaction was allowed to reach 0° C. The reaction was stirred for a full 18 hours then warmed to room temperature and stirred for an additional 6 hours. The mixture was washed with 1 M aqueous NaOH (1×125 mL). The organic layer was dried over sodium sulfate, filtered, and concentrated by rotary evaporation. The residue was purified by flash chromatography (0%-10% ethyl acetate/hexanes) to afford the product (4.0 g, 40% yield) as a colorless oil. The physical properties and spectral data were consistent with the reported values.

Benzyl (2S,4R)-4-((benzylsulfonyl)methyl)-2-(tert-butyl)-5-oxooxazolidine-3-carboxy-late (2). To a round bottom flask equipped with a stir bar was added benzyl (2S,4R)-4-((benzylthio)methyl)-2-(tert-butyl)-5-oxooxazolidine-3-carboxylate (3.15 g, 7.625 mmol, 1 equiv), meta-chloroperoxybenzoic acid (3.3 g, 19.06 mmol, 2.5 equiv), and DCM (100 mL). The reaction was stirred at room temperature for 18 hours. The reaction mixture was washed with 1 M aqueous sodium hydroxide (3×50 mL). The organic layer was dried over sodium sulfate, filtered, and concentrated by rotary evaporation. The residue was purified by flash chromatography (10%-30% ethyl acetate/hexanes) to afford the product (5.0 g, 74% yield) as a white foam. The physical properties and spectral data were consistent with the reported values.

Benzyl (S)-2-(tert-butyl)-4-methylene-5-oxooxazolidine-3-carboxylate (3). To a round bottom flask equipped with a stir bar was added (benzyl (2S,4R)-4-((benzylsulfonyl)methyl)-2-(tert-butyl)-5-oxooxazolidine-3-carboxylate) (2.75 g, 6.2 mmol, 1 equiv), and DCM (76 mL). The flask was chilled to 0° C. in an ice bath, and DBU (1.05 mL, 6.8 mmol, 1.1 equiv) was added dropwise via syringe. The reaction was stirred at 0° C. until the starting material had been consumed (determined by TLC, about 10 minutes). While still at 0° C., the reaction mixture was quenched with saturated aqueous ammonium chloride (25 mL), the layers were separated, and the organic phase was washed with saturated aqueous ammonium chloride (3×50 mL). The organic layer was dried over sodium sulfate, filtered, and concentrated by rotary evaporation. The residue was purified by flash chromatography (5%-10% ethyl acetate/hexanes) to afford the product (1.45 g, 83% yield) as a white solid. The physical properties and spectral data are consistent with the reported values.

Preparation of deuterated carboxylic acid

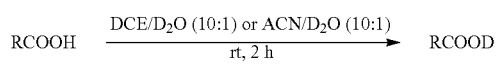

To the 20 mL-Schlenk tube, the carboxylic acid (0.4 mmol) was dissolved in 2 mL DCE, and then 0.2 mL D$_2$O was added and stirred at rt for 2 h. And the deuterated acids were directly used via syringe about 1 mL (0.2 mmol) to the reaction Schlenk tube and removed the solvent by vacuum. For compound with poor solubility in DCE, the acids were dissolved in 2 mL ACN/D$_2$O and stirred at rt for 2 h. The deuterated acid was used directly for the photocatalytic reaction via syringe.

Synthesis of deuterated compound, Procedure A: Mes-Acr-Me$^+$ClO$_4^-$

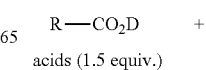    + acids (1.5 equiv.)

-continued

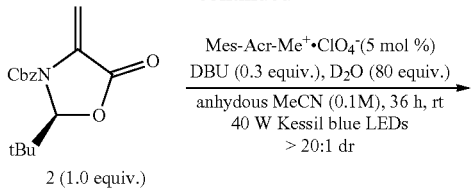

2 (1.0 equiv.)

Mes-Acr-Me⁺·ClO₄⁻ (5 mol %)
DBU (0.3 equiv.), D₂O (80 equiv.)
───────────────────────────
anhydous MeCN (0.1M), 36 h, rt
40 W Kessil blue LEDs
> 20:1 dr

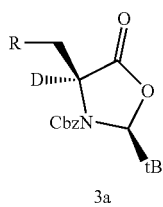

3a

To an oven-dried 20 mL-Schlenk tube equipped with a stir bar, was added deuterated carboxylic acids (0.3 mmol), chiral dehydroalanine 2 (0.2 mmol), Mes-Acr-Me⁺ClO₄⁻ (0.01 mmol). The tube was evacuated and back-filled with N2, then 2 mL anhydrous acetonitrile and 80 equiv. D₂O was added. The technique "freeze-pump-thaw" (three times) was applied to the reaction system to remove the oxygen. Finally, the 0.06 mmol DBU was added though the syringe. The solution was then stirred at room temperature under the irradiation of two 40 W Kessil Blue LEDs for specific time using electronic fan to cool the tube. After completion of the reaction, 2 mL water was added and extracted by ethyl acetate. The combined organic layer was washed with brine and then dried over anhydrous Na₂SO₄ and evaporated in vacuum. The desired products were obtained in the corresponding yields after purification by flash chromatography on silica gel eluting with hexane/ethyl acetate.

Synthesis of deuterated compound, Procedure B: 4CzIPN as photosensitizer

R—CO₂D + acids (1.2 equiv.)

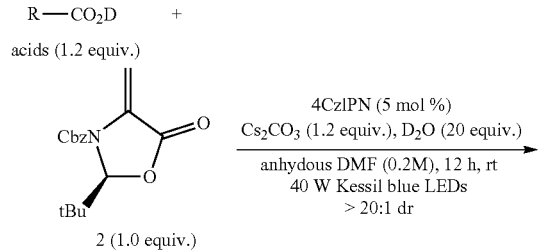

2 (1.0 equiv.)

4CzIPN (5 mol %)
Cs₂CO₃ (1.2 equiv.), D₂O (20 equiv.)
───────────────────────────
anhydous DMF (0.2M), 12 h, rt
40 W Kessil blue LEDs
> 20:1 dr

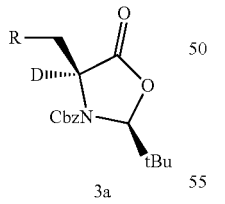

3a

To an oven-dried 20 mL-Schlenk tube equipped with a stir bar, was added deuterated carboxylic acids (0.24 mmol), chiral dehydroalanine (0.2 mmol), Cs₂CO₃ (0.24 mmol), 4CzIPN (0.01 mmol). The tube was evacuated and back-filled with N2 (three times), then sealed with parafilm. Then, deoxidized DMF (1 mL) was added using a syringe. The solution was then stirred at room temperature under the irradiation of two 40 W Kessil Blue LEDs for 6-18 h using electronic fan to cool the tube. After completion of the reaction, 2 mL water was added and extracted by ethyl acetate. The combined organic layer was washed with brine and then dried over anhydrous Na₂SO₄ and evaporated in vacuum. The desired products were obtained in the corresponding yields after purification by flash chromatography on silica gel eluting with hexane/ethyl acetate or hexane/dichloromethane.

For compound 3s, the procedure is similar to the general procedure A. To an oven-dried 20 mL-Schlenk tube equipped with a stir bar, was added deuterated carboxylic acids (0.3 mmol, prepared according to the procedure shown below), chiral dehydroalanine (0.2 mmol), CsF (0.3 mmol), Mes-Acr-Me⁺ClO₄⁻ (0.01 mmol). The tube was evacuated and back-filled with N2 (three times), then sealed with parafilm. Then, DCE (2 mL) and 80 equiv. D₂O was added using a syringe. The technique "freeze-pump-thaw" (three times) was applied to the reaction system to remove the oxygen. The solution was then stirred at room temperature under the irradiation of two 40 W Kessil Blue LEDs for specific time using electronic fan to cool the tube. After completion of the reaction, 2 mL water was added and extracted by DCM. The combined organic layer was washed with brine and then dried over anhydrous Na₂SO₄ and evaporated in vacuum. The desired products were obtained in the corresponding yields after purification by flash chromatography on silica gel eluting with hexane/ethyl acetate.

Example 1. Preparation of Various Deuterated Compounds

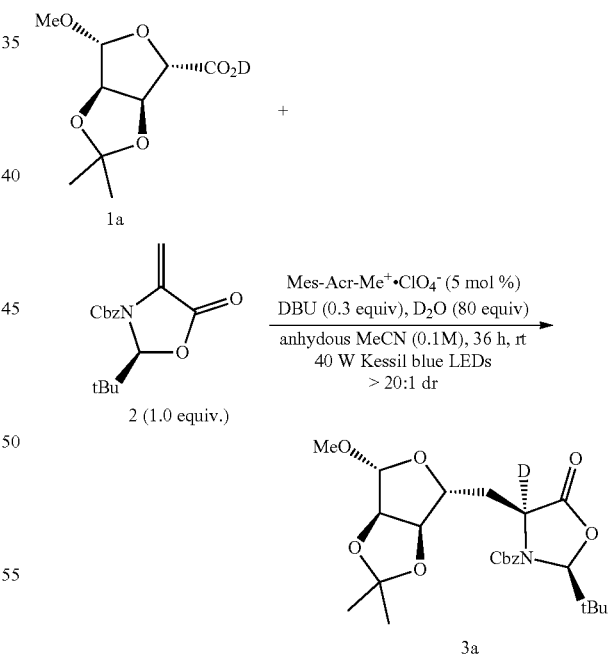

A reaction was carried out using deuterated methyl 2,3-O-(1-methylethylidene)-β-D-ribofuranosiduronic acid (1a, 1.5 equiv) as the glycosyl radical precursor, (S)-methyleneoxazolidinone 2 (1.0 equiv) as the amino acid surrogate, and D₂O (80 equiv) as the deuterium source in the presence of a photosensitizer (PS) irradiated by a 40 W Kessil blue LED (Table 1).

TABLE 1

| entry | Derivation from standard conditions | Yield (%)[b], D-content (%)[c] |
|---|---|---|
| 1 | Cs$_2$CO$_3$ (1.5 equiv) as base, anhydrous DCE as solvent for 24 h | 59, 92 |
| 2 | Ir[dF(CF$_3$)ppy]$_2$(dtbpy)PF$_6$ as PS, Cs$_2$CO$_3$ (1.5 equiv) as base, and D$_2$O (40 equiv) used in anhydrous DCE for 24 h | <5, nd[e] |
| 3 | 4CzIPN as PS, Cs$_2$CO$_3$ (1.5 equiv) as base, and D$_2$O (40 equiv) used in anhydrous DCE for 24 h | <5, nd[e] |
| 4 | Cs$_2$CO$_3$ (1.5 equiv.) as base, D$_2$O (40 equiv) used, anhydrous DCE as solvent for 24 h | 52, 85 |
| 5 | 0.6 equiv of DBU used. | 69, 96 |
| 6 | 1.2 equiv of 1a used. | 63, 96 |
| 7 | None | 70 (68),[d] 95 |
| 8 | No base | <5, nd[e] |
| 9 | No PS | <5, nd[e] |
| 10 | No light | <5, nd[e] |

[a]Reaction conditions: unless specified, a mixture of 1a (0.3 mmol), 2 (0.2 mmol) and catalyst (0.01 mmol) in anhydrous MeCN (2.0 mL) was irradiated with 40W Kessil blue LEDs in N$_2$ atmosphere at rt for 36 h.
[b]Yield based on $^1$H NMR.
[c]Determined by $^1$H NMR.
[d]Yield of isolated products.
[e]not determined.

Commonly used Cs$_2$CO$_3$ (1.5 equiv) as base in photoredox decarboxylation was tested in anhydrous dichloroethane (DCE) as solvent for 24 h. It should be noted that the use of deuterated acid and anhydrous solvent (eliminating H$_2$O) was necessary for achieving higher deuteration level. It was found that the reaction efficiency was PS dependent (Table 1, entries 1-3). Among the PS probed, mesityl acridinium salt (Mes-Acr-Me$^+$·ClO$_4$$^-$) delivered the desired product 3a in encouraging 59% yield (entry 1), while PS with low reduction potential Ir[dF(CF$_3$)ppy]$_2$(dtbpy)PF$_6$ (entry 2) and (4CzIPN (entry 3) failed to produce the product. In addition, 85% D-incorporation with excellent diastereometric ratio (dr)>20:1 was achieved. Further tested reaction conditions included solvent (entry 4), the amount of D$_2$O (entry 4), amount of base (entry 5), and amount of 1a (entry 6). The standard reaction conditions (entry 7) included: 0.3 equiv of DBU, 80 equiv of D$_2$O, and anhydrous MeCN. The control experiments confirmed that base, light, and photocatalyst were prerequisites for this transformation (entries 8-10).

Additional coupling reactions utilizing glycosyl carboxylic acids 1 with 2 (Scheme 1) were evaluated by providing an alternative for the synthesis of β-glycosyl α-deuterated amino acids. The protocol worked well for the tested pentose and hexose to give the desired products 3a-c in moderate yield and with high level of deuterium incorporation at the desired α-position. The anomeric effect of the glycosyl radicals delivers highly stereoselective anomeric products. Furthermore, the chiral (S)-oxazolidinone controlled the deuteration very well with >20:1 dr by only forming one diastereomer.

Synthesis of highly valued, structurally diverse and unique unnatural α-deuterated amino acids were conducted, which are difficult to be accessed by the established polar bond connection methods. These results show that the present method may serves as a general approach to various unnatural α-deuterated amino acids. Amino acids with bulky side chains (e.g., those having biological importance in peptido- and peptidomimetic relevant drug discovery and studies) are difficult to prepare using prior methods. In the present method, sterically demanding tertiary alkyl carboxylic acids, such as adamantyl group and analogue (3d-f), cyclohexyl derivatives (3g-l), and tert-butyl group bearing various functional groups (3k-o), gave good to excellent yield with uniformly high diastereoselectivity (dr>20:1) and high deuteration level (91-99%) despite their high steric hindrance. Moreover, the bridged structures (3p-q) were also incorporated with high efficiency. Next, cyclic secondary alkyl radicals (3r-v) bearing five-, six-, and seven-membered rings were probed. The less hindered structures gave rise to higher yield (80-91%) without sacrificing deuteration level (93-98%) and diastereoselectivity (>20:1 dr). The same trend was observed for acyclic secondary carboxylic acid (3w-y), including the natural amino acid d-leucine and aldehyde precursor-acetal. This study was further expanded to primary carboxylic acids (3z-ae) as alkyl radical precursors, which are generally difficult to generate. The results show that the present protocol worked smoothly for 3z-3ae in terms of reaction yield, dr and deuteration. Under mild reaction conditions, the radical-based method exhibits broad functional group tolerance, as demonstrated for protected amines (3m, 3u and 3ae), free hydroxyl (3n), alkene (3l), ester (3q), ether (3a-c, 3o and 3aa), acetal (3y), carbonyl (3ac, ad), and heteroaromatic (3ab).

Notably, no desired products were obtained under the standard reaction conditions for 3f, 3u, 3v, 3y, and 3ae. However, the reaction could proceed smoothly with a mixture of 1 (0.24 mmol), 2 (0.2 mmol) and 4CzIPN (0.01 mmol) in anhydrous DMF (2.0 mL) irradiated with 40 W Kessil blue LEDs in N2 atmosphere at rt (Scheme 1). Additional experiments using 4CzIPN as the photosensitizer to produce compound 3ae under various reaction conditions were conducted, and the results are shown in Table 2.

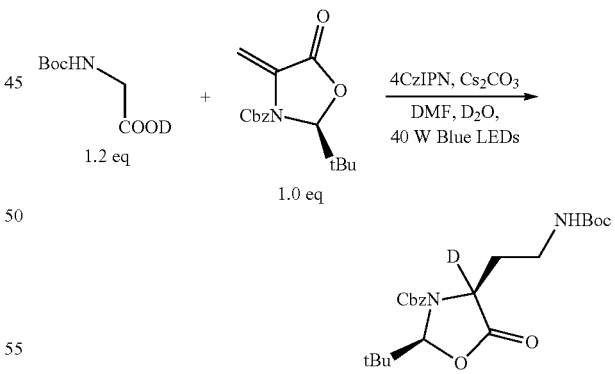

TABLE 2

| Base | PS (5 mol %) | Solvent | D$_2$O equiv. | D-content (%) | Yield [a] (%) | Time |
|---|---|---|---|---|---|---|
| Cs$_2$CO$_3$ (1.2 eq) | 4CzIPN | anhydrous DMF | 10 | 70 | 91 | 12 h |
| Cs$_2$CO$_3$ (1.2 eq) | 4CzIPN | anhydrous DMF | 20 | 86 | 89 | 12 h |
| Cs$_2$CO$_3$ (1.2 eq) | 4CzIPN | anhydrous DMF | 25 | 91 | 83 | 24 h |
| Cs$_2$CO$_3$ (1.2 eq) | 4CzIPN | anhydrous DMF | 30 | — | <5 | 24 h |

TABLE 2-continued

| Base | PS (5 mol %) | Solvent | D₂O equiv. | D-content (%) | Yield [a] (%) | Time |
|---|---|---|---|---|---|---|
| Cs₂CO₃ (1.2 eq) | 4CzIPN | anhydrous DMF | 30 | — | <5 | 24 h |
| DBU (0.3 eq) | Mes-Acr-Me⁺ClO4⁻ | anhydrous ACN | 80 | — | <5 | 36 h |

[a] The yields were calculated after purification

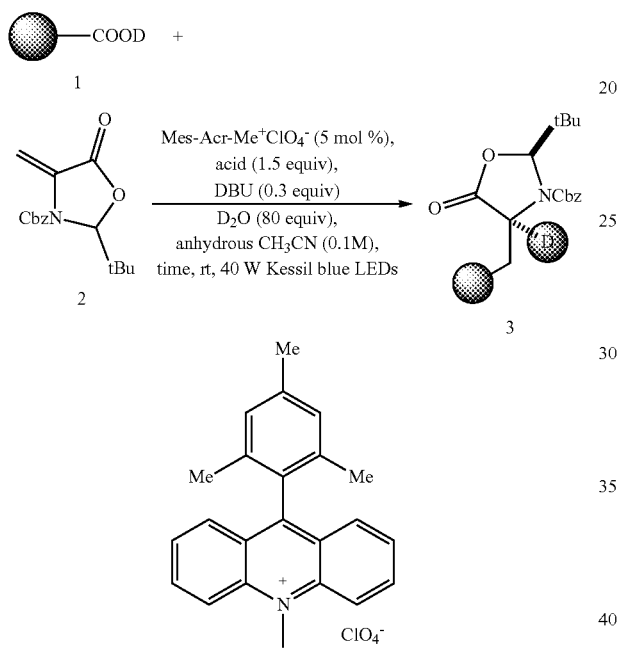

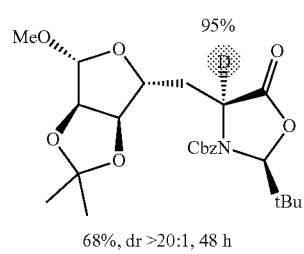

3a

68%, dr >20:1, 48 h

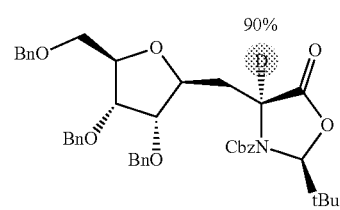

3b

46%, dr >20:1, 3 d

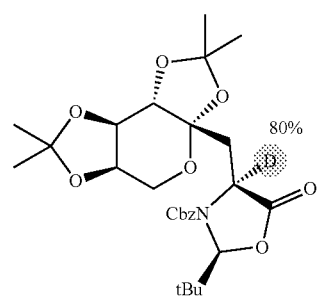

3c

48%, dr >20:1, 3 d

B. Tertiary carboxylic acids

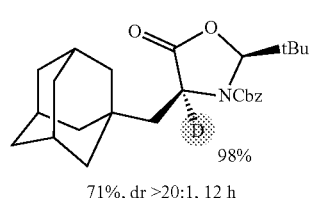

3d

71%, dr >20:1, 12 h

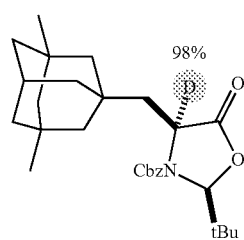

3e

84%, dr >20:1, 36 h

[a] Reaction conditions: unless specified, a mixture of 1 (0.3 mmol), 2 (0.2 mmol) and Mes-Acr-Me⁺·ClO₄⁻ (0.01 mmol) in anhydrous MeCN (2.0 mL) was irradiated with 40 W Kessil blue LEDs in N2 atmosphere at rt for specified time.

[b] Yield of isolated products were obtained.

[c] % Deuteration and dr were determined by ¹H NMR.

[d] For certain products (below), no desired product was obtained under the standard reaction conditions. The reaction was carried out, as follows: a mixture of 1 (0.24 mmol), 2 (0.2 mmol) Cs₂CO₃ (0.24 mmol) and 4CzIPN (0.01 mmol) in anhydrous DMF (2.0 mL) was irradiated with 40 W Kessil blue LEDs in N2 atmosphere at rt for specified time.

Representative results of the reaction under Scheme 1 are as follows.

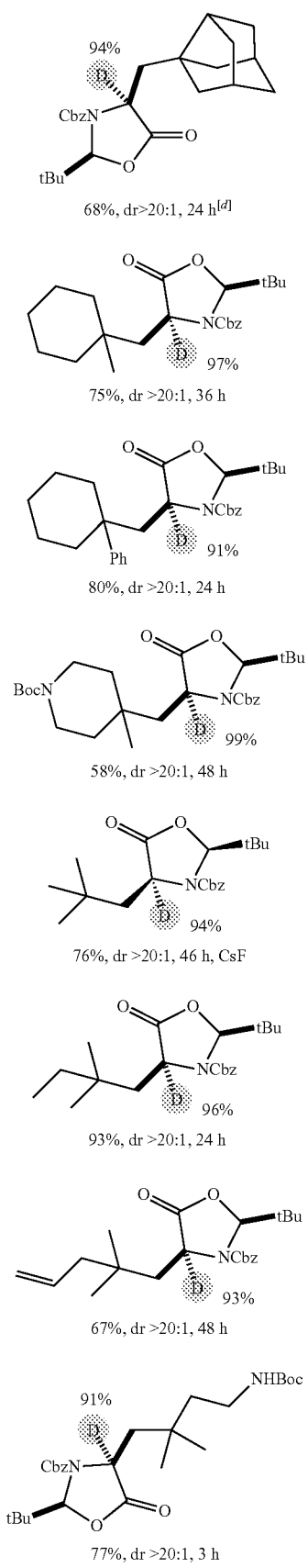
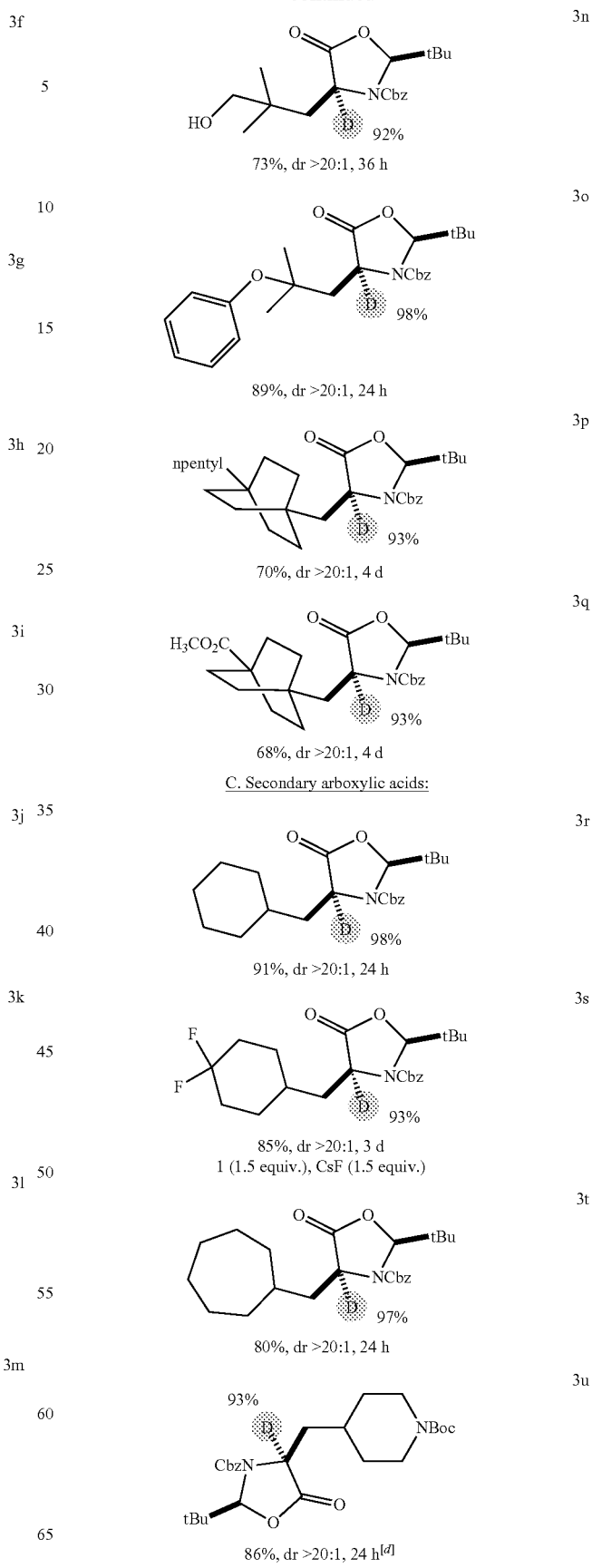

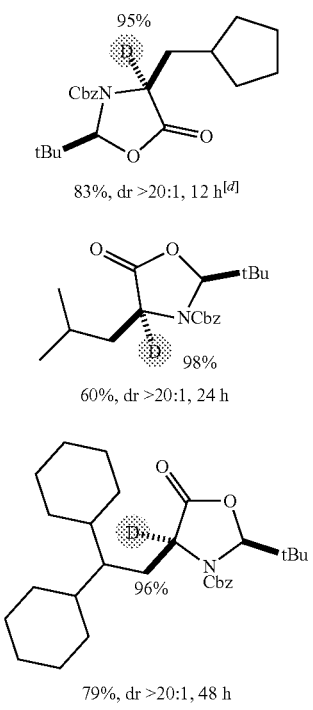
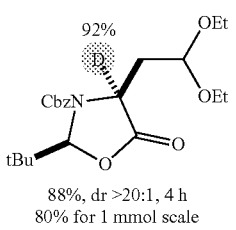

D. Primary carboxylic acids or α-keto acids:

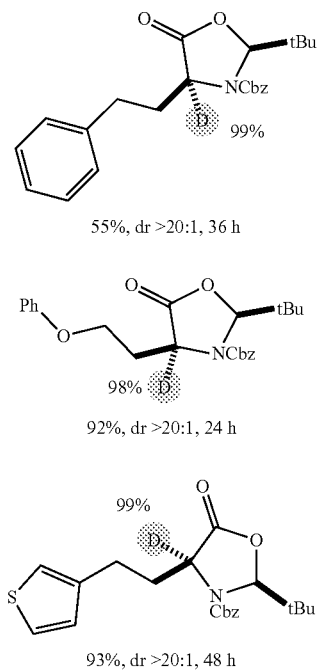
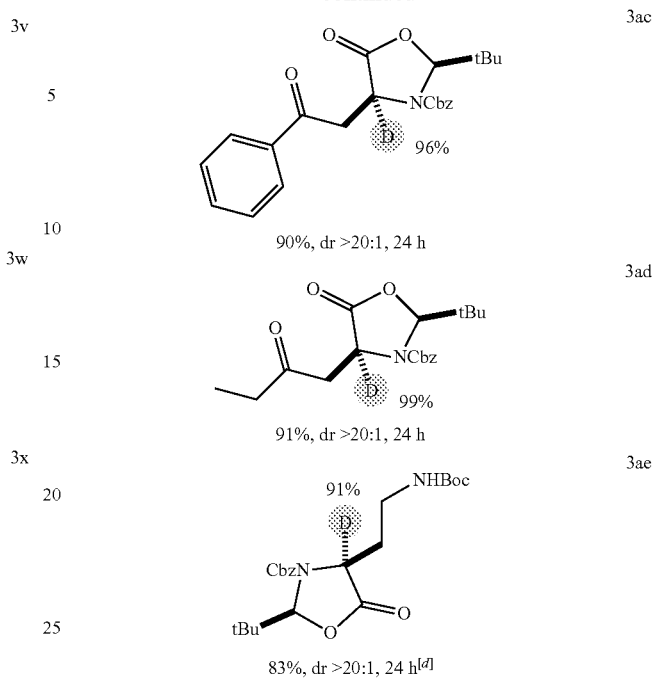

Benzyl (2S,4R)-2-(tert-butyl)-4-(((3aR,4R,6R,6aR)-6-methoxy-2,2-dimethyltetrahydrofuro[3,4-d][1,3]dioxol-4-yl)methyl)-5-oxooxazolidine-3-carboxylate (3a). The title product was prepared according to the general procedure A as colorless yellow oil 63 mg (68%). $^1$H NMR (400 MHz, CDCl$_3$) δ 7.36 (s, 5H), 5.57 (s, 1H), 5.28 (d, J=12.1 Hz, 1H), 5.15 (d, J=12.1 Hz, 1H), 4.97 (s, 1H), 4.75-4.57 (m, 1H), 3.33 (s, 3H), 2.15 (d, J=7.6 Hz, 2H), 1.48 (s, 3H), 1.32 (s, 3H), 0.96 (s, 9H). $^{13}$C NMR (101 MHz, CDCl$_3$) δ 172.1, 156.0, 135.6, 128.8, 128.7, 128.7, 112.6, 110.1, 96.7, 85.6, 83.8, 83.5, 68.5, 55.5, 54.4 (t), 38.2, 37.0, 26.7, 25.2, 25.1. HRMS (ESI) m/z [M+Na]$^+$ calculated for C$_{24}$H$_{32}$DNO$_8$: 487.2161, found 487.2158.

Benzyl (2S,4S)-4-(((2S,3S,4R,5R)-3,4-bis(benzyloxy)-5-((benzyloxy)methyl)tetrahydrofuran-2-yl)methyl)-2-(tert-butyl)-5-oxooxazolidine-3-carboxylate-4-d (3b). The title product was prepared according to the general procedure A as colorless oil about 64 mg (46%). $^1$H NMR (400 MHz, CDCl$_3$) δ=7.73-6.82 (m, 20H), 5.58 (s, 1H), 5.13 (q, J=12.0, 2H), 4.66-4.43 (m, 5H), 4.36 (d, J=11.8, 1H), 4.24 (q, J=6.8, 1H), 3.95 (s, 1H), 3.89 (dd, J=5.5, 3.3, 1H), 3.63-3.53 (m, 1H), 3.41 (qd, J=10.3, 4.4, 2H), 2.11-2.00 (m, 2H), 0.96 (s, 9H). $^{13}$C NMR (101 MHz, CDCl$_3$) δ 172.9, 156.3, 138.3, 138.0, 137.9, 135.4, 128.8, 128.7, 128.6, 128.5, 128.5, 128.4, 128.3, 128.0, 127.9, 127.9, 127.8, 127.7, 96.8, 82.0, 81.4, 77.2, 77.2, 76.5, 73.6, 72.2, 71.7, 70.6, 68.6, 54.2 (t), 37.9, 37.0, 25.1. HRMS (ESI) m/z [M+H]$^+$ calculated for C$_{42}$H$_{46}$DNO$_8$: 695.3437, found 695.3438.

Benzyl (2R,4S)-2-(tert-butyl)-5-oxo-4-(((3aS,5aR,8aR,8bS)-2,2,7,7-tetramethyltetrahydro-3aH-bis([1,3]dioxolo)[4,5-b:4',5'-d]pyran-3α-yl)methyl)oxazolidine-3-carboxylate (3c). The title product was prepared according to the general procedure A as colorless oil about 50 mg (48%). $^1$H NMR (400 MHz, CDCl$_3$) δ 7.46-7.22 (m, 5H), 5.54 (s, 1H), 5.27 (d, J=12.1 Hz, 1H), 5.07 (d, J=12.1 Hz, 1H), 4.51 (dd, J=7.8, 2.7 Hz, 1H), 4.47 (d, J=2.7 Hz, 1H), 4.16 (dd, J=7.8, 1.9 Hz, 1H), 3.83 (dd, J=13.0, 2.0 Hz, 1H), 3.64 (d, J=13.0 Hz, 1H), 2.45 (d, J=14.6 Hz, 1H), 2.31 (d, J=14.5 Hz, 1H), 1.48 (s, 3H), 1.40 (s, 3H), 1.31 (s, 3H), 1.29 (s, 3H), 0.94 (s, 9H). $^{13}$C NMR (101 MHz, CDCl$_3$) δ 172.4, 155.8, 135.6, 128.7, 128.7, 128.6, 109.1, 108.3, 102.5, 96.2, 77.2, 72.8, 70.8, 70.5, 68.2, 61.6, 52.5 (t), 44.0, 37.1, 26.5, 25.9, 25.3, 25.0, 24.3. HRMS (ESI) m/z [M+H]$^+$ calculated for C$_{27}$H$_{36}$DNO$_9$: 521.2604, found 521.2598.

Benzyl (2R,4S)-4-(((3S,5S,7S)-adamantan-1-yl)methyl)-2-(tert-butyl)-5-oxooxazolidine-3-carboxylate-4-d (3d). The title product was prepared according to the general procedure A as colorless oil about 61 mg (71%). $^1$H NMR (400 MHz, CDCl$_3$) δ 7.41-7.33 (m, 5H), 5.54 (s, 1H), 5.16 (q, J=11.8 Hz, 2H), 1.90 (s, 2H), 1.74 (d, J=14.3 Hz, 2H), 1.69-1.63 (m, 3H), 1.56 (t, J=10.9 Hz, 6H), 1.53-1.41 (m, 5H), 0.95 (s, 9H). $^{13}$C NMR (101 MHz, CDCl$_3$) δ 173.6, 155.8, 135.3, 129.1, 128.9, 128.8, 96.1, 77.2, 68.5, 52.5 (t), 49.3, 42.5, 37.1, 36.9, 32.9, 28.7, 25.1. HRMS (ESI) m/z [M+H]$^+$ calculated for C$_{26}$H$_{34}$DNO$_4$: 427.2702, found 427.2694.

Benzyl (2R,4S)-2-(tert-butyl)-4-(((1r,3R,5S,7S)-3,5-dimethyladamantan-1-yl)methyl)-5-oxooxazolidine-3-carboxylate-4-d (3e). The title product was prepared according to general procedure A as colorless oil about 76 mg (84%). $^1$H NMR (400 MHz, CDCl$_3$) δ 7.45-7.30 (m, 5H), 5.54 (s, 1H), 5.17 (q, 2H), 2.05-1.92 (m, 1H), 1.79 (d, J=14.3 Hz, 1H), 1.55 (d, J=14.3 Hz, 1H), 1.42 (d, J=10.3, 2.9 Hz, 1H), 1.38-1.31 (m, 1H), 1.25 (d, J=2.9 Hz, 5H), 1.19 (s, 2H), 1.15-1.08 (m, 2H), 1.03 (d, J=12.3 Hz, 1H), 0.95 (s, 9H), 0.77 (d, J=2.9 Hz, 6H). $^{13}$C NMR (101 MHz, CDCl$_3$) δ 173.5, 155.8, 135.5, 129.0, 128.8, 96.1, 77.2, 68.3, 52.6 (t), 51.1, 48.9, 48.8, 48.6, 43.2, 43.2, 43.0, 41.0, 37.1, 34.5, 31.3, 30.8, 30.7, 29.7, 25.10 HRMS (ESI) m/z [M+Na]$^+$ calculated for C$_{25}$H$_{38}$DNO$_4$: 477.2834, found 477.2831.

Benzyl (2R,4S)-2-(tert-butyl)-4-(((2R,3ar,5S,6aR)-hexahydro-2,5-methanopentalen-3a(1H)-yl)methyl)-5-oxooxazolidine-3-carboxylate-4-d (3f). The title product was prepared according to general procedure B as colorless oil about 56 mg (68%). $^1$H NMR (400 MHz, CDCl$_3$) δ 7.36 (s, 5H), 5.55 (s, 1H), 5.16 (d, J=1.5 Hz, 2H), 2.37-2.07 (m, 4H), 1.99 (d, J=14.2 Hz, 1H), 1.81-1.42 (m, 10H), 0.97 (s, 9H). $^{13}$C NMR (101 MHz, CDCl$_3$) δ 173.2, 155.7, 135.1, 128.9, 128.7, 128.6, 96.0, 68.4, 55.2-54.7 (m), 49.0, 48.3, 47.9, 44.2, 43.9, 43.8, 37.7, 37.5, 36.9, 35.0, 29.7, 25.0. HRMS (ESI) m/z [M+H]$^+$ calculated for C$_{25}$H$_{32}$DNO$_4$: 413.2545, found 413.2543.

Benzyl (2R,4S)-2-(tert-butyl)-4-((1-methylcyclohexyl)methyl)-5-oxooxazolidine-3-carboxylate-4-d (3g). The title product was prepared according to the general procedure A as colorless oil about 58 mg (75%). $^1$H NMR (400 MHz, CDCl$_3$) δ 7.72-7.30 (m, 5H), 5.55 (s, 1H), 5.16 (q, J=11.8 Hz, 2H), 1.90 (d, J=14.3 Hz, 1H), 1.67 (d, J=14.4 Hz, 1H), 1.52-1.16 (m, 10H), 0.97 (s, 9H). $^{13}$C NMR (101 MHz, CDCl$_3$) δ 173.5, 155.9, 135.3, 129.1, 128.9, 128.8, 96.2, 77.2, 68.5, 53.5 (t), 47.7, 38.1, 37.8, 37.0, 33.4, 26.4, 25.2, 24.3, 22.1, 22.1. HRMS (ESI) m/z [M+Na]$^+$ calculated for C$_{23}$H$_{32}$DNO$_4$: 411.2365, found 411.2360.

Benzyl (2R,4S)-2-(tert-butyl)-5-oxo-4-((1-phenylcyclohexyl)methyl)oxazolidine-3-carboxylate-4-d (3h). The title product was prepared according to the general procedure A as colorless oil about 72 mg (80%). $^1$H NMR (400 MHz, CDCl$_3$) δ 7.43-7.34 (m, 5H), 7.31 (t, J=7.7 Hz, 2H), 7.28-7.23 (m, 2H), 7.22-7.16 (m, 1H), 5.43 (s, 1H), 5.26-4.60 (m, 2H), 2.41 (d, J=13.7 Hz, 1H), 2.21 (d, J=14.2 Hz, 2H), 1.97 (d, J=14.3 Hz, 1H), 1.85-1.59 (m, 3H), 1.57-1.45 (m, 3H), 1.40-1.21 (m, 2H), 0.92 (s, 9H). $^{13}$C NMR (101 MHz, CDCl$_3$) δ 172.8, 155.7, 144.7, 135.5, 128.5, 128.4, 128.2, 127.5, 125.8, 95.9, 67.91, 53.8-53.4 (m), 41.3, 38.8, 37.6, 36.8, 34.9, 26.2, 24.9, 22.4, 22.2. HRMS (ESI) m/z [M+Na]$^+$ calculated for C$_{28}$H$_{34}$DNO$_4$: 473.2521, found 473.2518.

Benzyl (2R,4S)-4-((1-(tert-butoxycarbonyl)-4-methylpiperidin-4-yl)methyl)-2-(tert-butyl)-5-oxooxazolidine-3-carboxylate-4-d (3i). The title product was prepared according to the general procedure A as light yellow solid about 57 mg (58%). $^1$H NMR (400 MHz, CDCl$_3$) δ 7.54-7.29 (m, 5H), 5.53 (s, 1H), 5.24-5.02 (m, 2H), 3.53 (s, 2H), 3.11 (dd, J=17.6, 7.8 Hz, 2H), 1.92 (d, J=14.4 Hz, 1H), 1.68 (d, J=14.5 Hz, 1H), 1.56-1.47 (m, 1H), 1.43 (s, 9H), 1.39-1.18 (m, 3H), 1.02 (s, 3H), 0.94 (s, 9H). $^{13}$C NMR (101 MHz, CDCl$_3$) δ 173.2, 155.8, 155.0, 135.1, 129.1, 129.0, 128.9, 96.3, 79.4, 77.2, 68.7, 53.3 (t), 46.8, 37.0 (2C), 36.8, 32.0, 28.6, 25.1, 23.0. HRMS (ESI) m/z [M+Na]$^+$ calculated for C$_{27}$H$_{39}$DNO$_6$: 512.2841, found 512.2835.

Benzyl (2R,4S)-2-(tert-butyl)-4-neopentyl-5-oxooxazolidine-3-carboxylate-4-d (3j). The title product was prepared according to the general procedure A as colorless oil about 53 mg (76%). $^1$H NMR (400 MHz, CDCl$_3$) δ 7.43-7.32 (m, 5H), 5.55 (s, 1H), 5.18 (q, 2H), 1.90 (d, J=14.3 Hz, 1H), 1.66 (d, J=14.2 Hz, 1H), 0.99 (s, 9H), 0.96 (s, 9H). $^{13}$C NMR (101 MHz, CDCl$_3$) δ 173.4, 155.9, 135.3, 129.0, 128.8, 128.8, 96.1, 77.1, 68.4, 54.4-53.9 (m), 48.2, 37.0, 31.0, 29.8, 25.1. HRMS (ESI) m/z [M+Na]$^+$ calculated for C$_{20}$H$_{28}$DNO$_4$: 371.2052, found 371.2051.

Benzyl (2R,4S)-2-(tert-butyl)-4-(2,2-dimethylbutyl)-5-oxooxazolidine-3-carboxylate-4-d (3k). The title product was prepared according to the general procedure A as colorless oil about 67 mg (93%). $^1$H NMR (400 MHz, CDCl$_3$) δ 7.43-7.31 (m, 5H), 5.55 (s, 1H), 5.18 (q, 2H), 1.88 (d, J=14.3 Hz, 1H), 1.65 (d, J=14.3 Hz, 1H), 1.44-1.16 (m, 2H), 0.96 (s, 9H), 0.94 (s, 3H), 0.92 (s, 3H), 0.79 (t, J=7.5 Hz, 3H). $^{13}$C NMR (101 MHz, CDCl$_3$) δ 173.5, 155.9, 135.4, 129.0, 128.8, 128.8, 96.2, 77.2, 68.5, 54.2-53.7 (m), 46.5, 37.0, 34.9, 33.4, 26.6, 26.3, 25.2, 8.5. HRMS (ESI) m/z [M+Na]$^+$ calculated for C$_{21}$H$_{30}$DNO$_4$: 385.2208, found 385.2205.

Benzyl (2R,4S)-2-(tert-butyl)-4-(2,2-dimethylpent-4-en-1-yl)-5-oxooxazolidine-3-carboxylate-4-d (3l). The title product was prepared according to the general procedure A as colorless oil about 50 mg (67%). $^1$H NMR (400 MHz, CDCl$_3$) δ 7.44-7.32 (m, 5H), 5.87-5.71 (m, 1H), 5.55 (s, 1H), 5.27-5.11 (m, 2H), 5.07-4.93 (m, 2H), 2.05 (qd, J=13.6, 7.4 Hz, 2H), 1.90 (d, J=14.4 Hz, 2H), 1.67 (d, J=14.4 Hz, 1H), 0.97 (d, J=9.0 Hz, 15H). $^{13}$C NMR (101 MHz, CDCl$_3$) δ 173.4, 155.9, 135.3, 135.1, 129.0, 128.9, 128.8, 117.6, 96.3, 77.2, 68.5, 54.0 (t), 47.2, 46.5, 37.0, 33.6, 27.0, 26.7, 25.1. HRMS (ESI) m/z [M+Na]$^+$ calculated for C$_{22}$H$_{30}$DNO$_4$: 397.2208, found 397.2204.

Benzyl (2R,4S)-4-(4-((tert-butoxycarbonyl)-12-azaneyl)-2,2-dimethylbutyl)-2-(tert-butyl)-5-oxooxazolidine-3-carboxylate-4-d (3m). The title product was prepared according to the general procedure A as colorless oil about 74 mg (77%). $^1$H NMR (400 MHz, CDCl$_3$) δ 7.43-7.29 (m, 5H), 5.54 (s, 1H), 5.17 (q, 2H), 4.47 (s, 1H), 3.08 (dd, J=18.5, 8.5 Hz, 2H), 1.92 (d, J=14.4 Hz, 1H), 1.65 (d, J=14.4 Hz, 1H), 1.49 (t, J=8.3 Hz, 2H), 1.43 (s, 9H), 0.96 (d, J=12.9 Hz, 15H). $^{13}$C NMR (101 MHz, CDCl$_3$) δ 173.3, 156.1, 155.8, 135.2, 129.0, 128.9, 128.8, 96.2, 79.1, 77.2, 68.6, 53.9 (t), 46.4, 41.3, 37.0, 36.8, 32.9, 28.6, 27.4, 27.3, 25.1. HRMS (ESI) m/z [M+H]$^+$ calculated for C$_{26}$H$_{39}$DN$_2$O$_6$: 478.3022, found 478.3015.

Benzyl (2R,4S)-2-(tert-butyl)-4-(3-hydroxy-2,2-dimethylpropyl)-5-oxooxazolidine-3-carboxylate-4-d (3n). The title product was prepared according to the general procedure A as colorless oil about 53 mg (73%). $^1$H NMR (400

MHz, CDCl₃) δ 7.49-7.30 (m, 5H), 5.55 (s, 1H), 5.17 (s, 2H), 3.43 (s, 1H), 3.39-3.28 (m, 2H), 1.98 (d, J=14.6 Hz, 1H), 1.72 (d, J=14.8 Hz, 1H), 0.95 (d, J=3.4 Hz, 15H). $^{13}$C NMR (101 MHz, CDCl₃) δ 174.7, 155.8, 135.0, 129.1, 129.0, 128.8, 96.3, 77.2, 69.7, 68.8, 53.9-53.4 (m), 43.3, 37.2, 36.1, 29.8, 24.9. HRMS (ESI) m/z [M+H]⁺ calculated for $C_{26}H_{39}DN_2O_6$: 365.2181, found 365.2178.

Benzyl (2R,4S)-2-(tert-butyl)-4-(2-methyl-2-phenoxypropyl)-5-oxooxazolidine-3-carboxylate-4-d (3o). The title product was prepared according to the general procedure A as colorless oil about 76 mg (89%). $^1$H NMR (400 MHz, CDCl₃) δ 7.37-7.27 (m, 5H), 7.24 (t, J=7.8 Hz, 2H), 7.06 (t, J=7.4 Hz, 1H), 6.95 (d, J=7.9 Hz, 2H), 5.58 (s, 1H), 5.14 (q, 2H), 2.42-2.14 (m, 2H), 1.36 (s, 6H), 0.97 (s, 9H). $^{13}$C NMR (101 MHz, CDCl₃) δ 173.1, 156.1, 154.9, 135.4, 129.0, 128.8, 128.7, 128.7, 124.3, 123.6, 96.5, 79.2, 77.2, 68.5, 53.7 (t), 47.3, 37.0, 27.3, 26.2, 25.1. HRMS (ESI) m/z [M+H]⁺ calculated for $C_{25}H_{30}DNO_5$: 427.2338, found 427.2332.

Benzyl (2R,4S)-2-(tert-butyl)-5-oxo-4-((4-pentylbicyclo[2.2.2]octan-1-yl)methyl)oxazolidine-3-carboxylate-4-d (3p). The title product was prepared according to the general procedure A as white solid about 66 mg (70%). $^1$H NMR (400 MHz, CDCl₃) δ 7.36 (p, J=3.7, 2.9 Hz, 5H), 5.53 (s, 1H), 5.15 (d, J=2.2 Hz, 2H), 1.77 (d, J=14.4 Hz, 1H), 1.54 (d, J=14.4 Hz, 1H), 1.47-1.35 (m, 6H), 1.28 (p, J=7.4 Hz, 8H), 1.22-1.07 (m, 4H), 1.00 (dd, J=9.9, 5.8 Hz, 2H), 0.94 (s, 9H), 0.87 (t, J=7.2 Hz, 3H). $^{13}$C NMR (101 MHz, CDCl₃) δ 173.59, 155.85, 135.26, 129.11, 128.86, 128.79, 96.14, 77.16, 68.53, 53.40 (t), 46.54, 41.82, 37.02, 33.02, 31.53, 31.32, 31.26, 30.60, 25.10, 23.46, 22.85, 14.26. HRMS (ESI) m/z [M+Na]⁺ calculated for $C_{29}H_{42}DNO_4$: 493.3147, found 493.3146.

Benzyl (2R,4S)-2-(tert-butyl)-4-((4-(methoxycarbonyl)bicyclo[2.2.2]octan-1-yl)methyl)-5-oxooxazolidine-3-carboxylate-4-d (3q). The title product was prepared according to the general procedure A as white solid about 62 mg (68%). $^1$H NMR (400 MHz, CDCl₃) δ 7.67-7.31 (m, 5H), 5.54 (s, 1H), 5.15 (d, J=2.5 Hz, 2H), 3.63 (s, 3H), 1.80 (d, J=14.4 Hz, 1H), 1.70 (t, J=8.0 Hz, 6H), 1.62-1.54 (m, 2H), 1.52-1.37 (m, 5H), 0.94 (s, 9H). $^{13}$C NMR (101 MHz, CDCl₃) δ 178.5, 173.4, 155.8, 135.1, 129.2, 129.0, 128.8, 96.2, 77.2, 68.7, 53.3 (t), 51.8, 46.1, 38.9, 37.1, 31.1, 30.6, 28.5, 25.1. HRMS (ESI) m/z [M+Na]⁺ calculated for $C_{26}H_{34}DNO_6$: 481.2419, found 481.2414.

Benzyl (2R,4S)-2-(tert-butyl)-4-(cyclohexylmethyl)-5-oxooxazolidine-3-carboxylate-4-d (3r). The title product was prepared according to the general procedure A as colorless oil about 68 mg (91%). $^1$H NMR (400 MHz, CDCl₃) δ 7.36 (d, J=1.9 Hz, 5H), 5.55 (s, 1H), 5.16 (q, J=11.9 Hz, 2H), 1.88-1.71 (m, 3H), 1.63 (dq, J=9.5, 6.7, 6.1 Hz, 5H), 1.33-1.06 (m, 3H), 0.96 (s, 9H), 0.92-0.59 (m, 2H). $^{13}$C NMR (101 MHz, CDCl₃) δ 173.24, 156.14, 135.35, 128.79, 128.78, 96.40, 77.16, 68.49, 55.10-54.58 (m), 41.19, 37.05, 34.36, 33.55, 32.95, 26.54, 26.09, 26.07, 25.10. HRMS (ESI) m/z [M+Na]⁺ calculated for $C_{22}H_{30}DNO_4$: 397.2208, found 397.2204.

Benzyl (2R,4S)-2-(tert-butyl)-4-((4,4-difluorocyclohexyl)methyl)-5-oxooxazolidine-3-carboxylate-4-d (3s). The title product was prepared according to the general procedure A as colorless oil about 70 mg (85%). $^1$H NMR (400 MHz, CDCl₃) δ 7.37 (pd, J=6.6, 5.6, 2.5 Hz, 5H), 5.56 (s, 1H), 5.15 (s, 2H), 2.21-1.54 (m, 9H), 1.32-1.15 (m, 2H), 0.96 (s, 9H). $^{13}$C NMR (101 MHz, CDCl₃) δ 172.9, 156.1, 135.05, 129.0, 128.9, 128.8, 125.9, 123.5, 121.1, 96.5, 77.1, 68.8, 55.3-54.8 (m), 39.4, 37.1, 33.2, 32.6, 29.8, 29.1, 28.5, 25.5, 25.0. HRMS (ESI) m/z [M+Na]⁺ calculated for $C_{22}H_{28}DF_2NO_4$: 433.2020, found 433.2014.

Benzyl (2R,4S)-2-(tert-butyl)-4-(cycloheptylmethyl)-5-oxooxazolidine-3-carboxylate-4-d (3t). The title product was prepared according to the general procedure A as colorless oil about 62 mg (80%). $^1$H NMR (400 MHz, CDCl₃) δ 7.43-7.30 (m, 5H), 5.55 (s, 1H), 5.16 (q, J=11.9 Hz, 2H), 2.05-1.82 (m, 1H), 1.83-1.62 (m, 4H), 1.61-1.29 (m, 8H), 1.24-1.03 (m, 2H), 0.96 (s, 9H). $^{13}$C NMR (101 MHz, CDCl₃) δ 173.2, 156.2, 135.4, 128.8, 96.4, 77.2, 68.5, 55.6-55.1 (m), 41.6, 37.1, 35.7, 34.7, 34.0, 29.8, 28.6, 28.6, 26.1, 25.1. HRMS (ESI) m/z [M+Na]⁺ calculated for $C_{23}H_{32}DNO_4$: 411.2365, found 411.2363.

Benzyl (2R,4S)-4-((1-(tert-butoxycarbonyl)piperidin-4-yl)methyl)-2-(tert-butyl)-5-oxooxazolidine-3-carboxylate-4-d (3u). The title product was prepared according to the general procedure B as colorless oil about 82 mg (86%). $^1$H NMR (400 MHz, CDCl₃) δ 7.52-7.30 (m, 5H), 5.65-5.49 (m, 1H), 5.22-5.09 (m, 2H), 3.97 (s, 2H), 2.59 (d, J=13.3 Hz, 2H), 1.80 (q, J=6.7, 6.2 Hz, 2H), 1.74-1.55 (m, 3H), 1.45 (d, J=0.9 Hz, 9H), 1.17-0.98 (m, 2H), 0.95 (s, 9H). $^{13}$C NMR (101 MHz, CDCl₃) δ 172.9, 156.1, 154.9, 135.1, 129.0, 128.9, 128.8, 96.5, 79.4, 77.2, 68.7, 54.9-54.4 (m), 40.2, 37.1, 32.9, 32.3, 31.8, 28.6, 25.1. HRMS (ESI) m/z [M+Na]⁺ calculated for $C_{26}H_{37}DN_2O_6$: 498.2685, found 498.2681.

Benzyl (2R,4S)-2-(tert-butyl)-4-(cyclopentylmethyl)-5-oxooxazolidine-3-carboxylate-4-d (3v). The title product was prepared according to the general procedure B as colorless oil about 60 mg (83%). $^1$H NMR (400 MHz, CDCl₃) δ 7.45-7.30 (m, 5H), 5.54 (s, 1H), 5.16 (s, 2H), 2.30-2.12 (m, 1H), 1.95 (dd, J=13.6, 6.2 Hz, 1H), 1.82-1.67 (m, 3H), 1.60-1.40 (m, 4H), 1.19-1.02 (m, 2H), 0.96 (s, 9H). $^{13}$C NMR (101 MHz, CDCl₃) δ 173.1, 156.1, 135.3, 128.8, 128.8, 96.4, 77.2, 68.5, 56.7, 56.4 (t), 39.7, 37.1, 36.6, 33.0, 32.0, 25.2, 25.1, 25.0. HRMS (ESI) m/z [M+Na]⁺ calculated for $C_{21}H_{28}DNO_4$: 383.2052, found 383.2051.

Benzyl (2R,4S)-2-(tert-butyl)-4-isobutyl-5-oxooxazolidine-3-carboxylate-4-d (3w). The title product was prepared according to the general procedure A as colorless oil about 40 mg (60%). $^1$H NMR (400 MHz, CDCl₃) δ 7.71-7.32 (m, 5H), 5.55 (s, 1H), 5.16 (d, J=2.5 Hz, 2H), 1.99 (dq, J=7.9, 6.6 Hz, 1H), 1.78 (dd, J=13.7, 6.3 Hz, 1H), 1.64 (dd, J=13.7, 7.9 Hz, 1H), 0.96 (s, 9H), 0.92 (dd, J=6.7, 2.7 Hz, 6H). $^{13}$C NMR (101 MHz, CDCl₃) δ 173.1, 156.2, 135.4, 128.8, 128.8, 96.4, 77.2, 68.5, 55.4 (t), 42.5, 37.1, 25.1, 25.1, 22.9, 22.1. HRMS (ESI) m/z [M+Na]⁺ calculated for $C_{19}H_{26}DNO_4$: 357.1895, found 357.1895.

Benzyl (2R,4S)-2-(tert-butyl)-4-(2,2-dicyclohexylethyl)-5-oxooxazolidine-3-carboxylate-4-d (3x). The title product was prepared according to the general procedure A as white solid about 74 mg (79%). $^1$H NMR (400 MHz, CDCl₃) δ 7.34 (s, 5H), 5.51 (s, 1H), 5.17 (q, 2H), 1.93-1.74 (m, 2H), 1.73-1.47 (m, 12H), 1.45-1.30 (m, 2H), 1.27-1.01 (m, 6H), 1.03-0.80 (m, 11H). $^{13}$C NMR (101 MHz, CDCl₃) δ 172.8, 156.2, 135.5, 128.8, 128.8, 96.2, 77.2, 68.4, 56.6 (t), 44.0, 39.6, 39.5, 37.1, 32.6, 31.6, 31.5, 30.2, 29.8, 27.2, 27.1, 27.0, 26.9, 26.8, 25.2. HRMS (ESI) m/z [M+H]⁺ calculated for $C_{29}H_{42}DNO_4$: 471.3328, found 471.3327.

Benzyl (2R,4S)-2-(tert-butyl)-4-(2,2-diethoxyethyl)-5-oxooxazolidine-3-carboxylate-4-d (3y). The title product was prepared according to the general procedure B as colorless oil about 69 mg (88%). $^1$H NMR (400 MHz, CDCl₃) δ 7.59-7.30 (m, 5H), 5.56 (s, 1H), 5.30-5.08 (m, 2H), 4.96 (dd, J=7.3, 4.9 Hz, 1H), 3.77-3.56 (m, 2H), 3.54-3.36 (m, 2H), 2.34-2.01 (m, 2H), 1.16 (dt, J=20.0, 7.0 Hz, 6H), 0.96 (s, 9H). $^{13}$C NMR (101 MHz, CDCl₃) δ 172.7, 155.9, 135.4, 128.8, 128.7, 128.6, 99.4, 96.6, 77.2, 68.4, 61.6, 61.3, 54.2-53.7 (m), 37.3, 37.2, 25.0, 15.5, 15.4. HRMS (ESI) m/z [M+H]$^+$ calculated for C$_{21}$H$_{30}$DNO$_6$: 417.2106, found 417.2100.

Benzyl (2R,4S)-2-(tert-butyl)-5-oxo-4-phenethyloxazolidine-3-carboxylate-4-d (3z). The title product was prepared according to the general procedure A as colorless oil about 42 mg (55%). $^1$H NMR (400 MHz, CDCl$_3$) δ 7.44-7.34 (m, 3H), 7.34-7.28 (m, 2H), 7.28-7.23 (m, 2H), 7.23-7.14 (m, 3H), 5.55 (s, 1H), 5.13 (s, 2H), 3.11-2.92 (m, 1H), 2.91-2.77 (m, 1H), 2.35-2.08 (m, 2H), 0.97 (s, 9H). $^{13}$C NMR (101 MHz, CDCl$_3$) δ 172.6, 156.1, 140.7, 135.4, 128.8, 128.7, 128.6, 126.3, 96.4, 77.2, 68.4, 56.3 (t), 37.2, 34.9, 32.4, 25.1. HRMS (ESI) m/z [M+H]$^+$ calculated for C$_{23}$H$_{26}$DNO$_4$: 405.1895, found 405.1893.

Benzyl (2R,4S)-2-(tert-butyl)-5-oxo-4-(2-phenoxyethyl)oxazolidine-3-carboxylate-4-d (3aa). The title product was prepared according to the general procedure A as colorless oil about 73 mg (92%). $^1$H NMR (400 MHz, CDCl$_3$) δ 7.47-7.29 (m, 5H), 7.26 (t, J=7.8 Hz, 2H), 6.95 (t, J=7.4 Hz, 1H), 6.80 (d, J=8.1 Hz, 2H), 5.62 (s, 1H), 5.16 (d, J=12.0 Hz, 1H), 5.02 (d, J=12.0 Hz, 1H), 4.29-4.09 (m, 2H), 2.50-2.20 (m, 2H), 1.00 (s, 9H). $^{13}$C NMR (101 MHz, CDCl$_3$) δ 172.5, 158.7, 156.2, 135.4, 129.6, 128.8, 128.7, 128.6, 121.0, 114.5, 96.8, 77.2, 68.5, 64.1, 54.3 (t), 37.1, 33.1, 25.0. HRMS (ESI) m/z [M+H]$^+$ calculated for C$_{23}$H$_{26}$DNO$_5$: 399.2025, found 399.2021.

Benzyl (2R,4S)-2-(tert-butyl)-5-oxo-4-(2-(thiophen-3-yl)ethyl)oxazolidine-3-carboxylate-4-d (3ab). The title product was prepared according to the general procedure A as colorless oil about 72 mg (93%). $^1$H NMR (400 MHz, CDCl$_3$) δ 7.51-7.27 (m, 5H), 7.21 (dd, J=5.0, 2.9 Hz, 1H), 7.00-6.69 (m, 2H), 5.54 (s, 1H), 5.13 (s, 2H), 3.13-2.78 (m, 2H), 2.38-2.07 (m, 2H), 0.96 (s, 9H). $^{13}$C NMR (101 MHz, CDCl$_3$) δ 172.4, 155.9, 140.7, 135.2, 128.7, 128.6, 128.5, 128.1, 125.5, 120.7, 96.3, 68.3, 55.9 (t), 37.0, 33.6, 26.6, 24.9. HRMS (ESI) m/z [M+Na]$^+$ calculated for C$_{23}$H$_{26}$DNO$_5$: 411.1459, found 411.1456.

Benzyl (2R,4S)-2-(tert-butyl)-5-oxo-4-(2-oxo-2-phenylethyl)oxazolidine-3-carboxylate-4-d (3ac). The title product was prepared according to the general procedure A as colorless oil about 71 mg (90%). $^1$H NMR (400 MHz, CDCl$_3$) δ 7.89 (d, J=7.7 Hz, 2H), 7.57 (t, J=7.4 Hz, 1H), 7.44 (t, J=7.6 Hz, 2H), 7.34-7.08 (m, 5H), 5.59 (s, 1H), 5.04 (q, 2H), 3.75-3.12 (m, 2H), 1.00 (s, 9H). $^{13}$C NMR (101 MHz, CDCl$_3$) δ 194.8, 172.1, 155.6, 136.3, 135.2, 133.6, 128.9, 128.7, 128.6, 128.5, 128.3, 96.3, 77.2, 68.3, 53.7-53.2 (m), 41.9, 37.5, 24.9. HRMS (ESI) m/z [M+H]$^+$ calculated for C$_{23}$H$_{24}$DNO$_5$: 397.1868, found 397.1863.

Benzyl (2R,4S)-2-(tert-butyl)-5-oxo-4-(2-oxobutyl)oxazolidine-3-carboxylate-4-d (3ad). The title product was prepared according to the general procedure A as colorless oil about 63 mg (91%). $^1$H NMR (400 MHz, CDCl$_3$) δ 7.35 (qd, J=6.1, 5.2, 2.8 Hz, 5H), 5.57 (s, 1H), 5.14 (s, 2H), 3.10-2.73 (m, 2H), 2.60-2.20 (m, 2H), 1.03 (t, J=7.3 Hz, 3H), 0.96 (s, 9H). $^{13}$C NMR (101 MHz, CDCl$_3$) δ 205.6, 172.3, 155.6, 135.3, 128.8, 128.7, 128.5, 96.3, 77.2, 68.4, 53.1 (t), 45.0, 37.5, 36.6, 24.8, 7.6. HRMS (ESI) m/z [M+H]$^+$ calculated for C$_{19}$H$_{24}$DNO$_5$: 349.1868, found 349.1868.

Benzyl (2R,4S)-4-(2-((tert-butoxycarbonyl)amino)ethyl)-2-(tert-butyl)-5-oxooxazolidine-3-carboxylate-4-d (3ae). The title product was prepared according to the general procedure B as colorless oil about 70 mg (83%). $^1$H NMR (400 MHz, CDCl$_3$) δ 7.84-7.30 (m, 5H), 5.57 (s, 1H), 5.18 (d, J=2.1 Hz, 2H), 3.50 (m, 1H), 3.25-3.00 (m, 1H), 2.26-2.03 (m, 1H), 1.97 (s, 1H), 1.43 (s, 9H), 0.94 (s, 9H). $^{13}$C NMR (101 MHz, CDCl$_3$) δ 172.7, 156.5, 155.9, 135.1, 129.0, 128.9, 128.8, 96.7, 79.3, 77.2, 68.8, 55.4 (t), 37.4, 37.0, 33.3, 28.6, 25.1. HRMS (ESI) m/z [M+Na]$^+$ calculated for C$_{22}$H$_{31}$DN$_2$O$_6$: 444.2215, found 444.2213.

Example 2. Late-Stage Modifications on Medicinal Agents and Natural Products

As shown in Scheme 2, the present method was successfully applied to natively and selectively modify bezafibrate and drug gemfibrozil, clinically used lipid lowering agents, to give amino acid derivatives 7 and 8 in 79 and 68% yield, and 96 and 97% D-incorporation, respectively and with >20:1 dr. Moreover, an anti-inflammatory agent 3-indolacetic acid, indomethacin was efficiently transformed into corresponding isotopically labelled amino acid (9) in good yield (85%), high deuteration (97%) and excellent dr (>20:1). Further, enoxolone (10) containing a secondary alcohol and an α,β-unsaturated ketone, was tolerated. Of note, a modified protocol using 0.6 equiv. of DBU with a 0.05M concentration was used to improve the reaction efficiency.

Scheme 2.
Late-stage functionalization of pharmaceutics and natural products

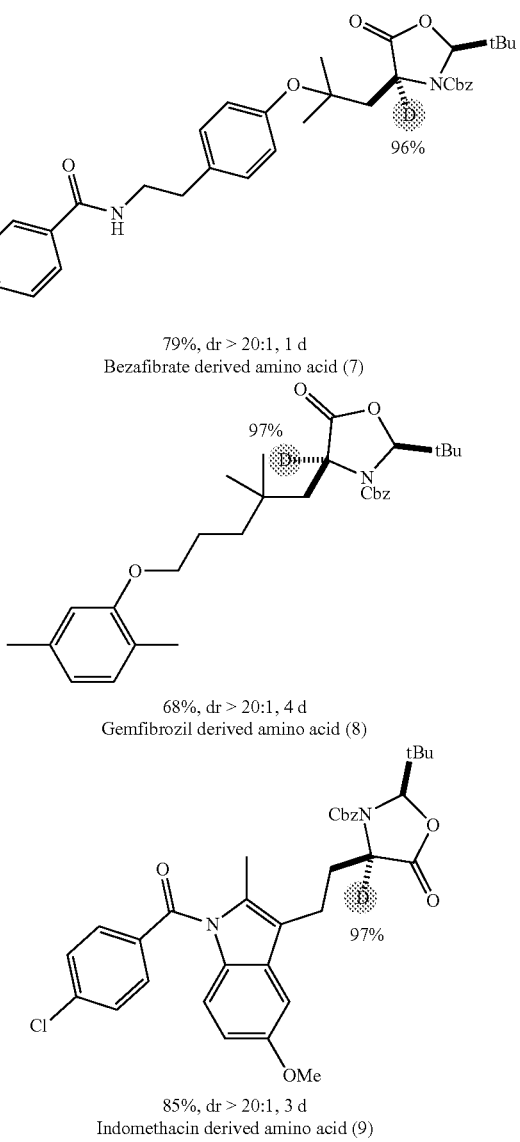

79%, dr > 20:1, 1 d
Bezafibrate derived amino acid (7)

68%, dr > 20:1, 4 d
Gemfibrozil derived amino acid (8)

85%, dr > 20:1, 3 d
Indomethacin derived amino acid (9)

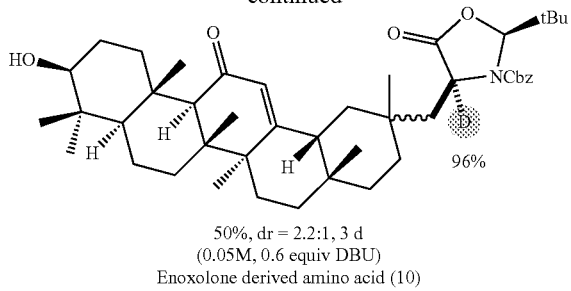

50%, dr = 2.2:1, 3 d
(0.05M, 0.6 equiv DBU)
Enoxolone derived amino acid (10)

Yield of isolated products. Deuteration and dr determined by $^1$H NMR

Benzyl (2R,4S)-2-(tert-butyl)-4-(2-(4-(2-(4-chlorobenzamido)ethyl)phenoxy)-2-methylpropyl)-5-oxooxazolidine-3-carboxylate-4-d (7). The title product was prepared according to the general procedure A as oil about 96 mg (790). $^1$H NMR (400 MHz, CDCl$_3$) δ 7.61 (d, J=8.5 Hz, 2H), 7.35 (d, J=8.5 Hz, 2H), 7.34-7.26 (m, 5H), 7.09 (d, J=8.4 Hz, 2H), 6.91 (d, J=8.4 Hz, 2H), 5.58 (s, 1H), 5.24-5.00 (i, 2H), 3.67 (q, J=6.7 Hz, 2H), 2.88 (t, J=6.9 Hz, 2H), 2.54-2.13 (m, 2H), 1.36 (s, 6H), 0.97 (s, 9H). $^{13}$C NMR (101 MHz, CDCl$_3$) δ 173.1, 166.5, 156.0, 153.6, 137.7, 135.3, 133.8, 133.1, 129.3, 128.9, 128.7, 128.7, 128.7, 128.4, 124.5, 96.5, 79.2, 77.2, 68.5, 53.7 (t), 47.2, 41.4, 37.0, 35.0, 27.1, 26.3, 25.1. HRMS (ESI) m/z [M+H]$^+$ calculated for $C_{34}H_{38}DClN_2O_6$: 608.2632, found 608.2633.

Benzyl (2R,4S)-2-(tert-butyl)-4-(5-(2,5-dimethylphenoxy)-2,2-dimethylpentyl)-5-oxooxazolidine-3-carboxylate-4-d (8). The title product was prepared according to the general procedure A as colorless oil about 67 mg (680%). $^1$H NMR (400 MHz, CDCl$_3$) δ 7.45-7.30 (m, 5H), 7.11-6.95 (m, 1H), 6.66 (dd, J=7.8, 1.6 Hz, 1H), 6.63 (d, J=1.6 Hz, 1H), 5.57 (s, 1H), 5.28-5.08 (m, 2H), 4.08-3.73 (m, 2H), 2.32 (s, 3H), 2.18 (s, 3H), 1.96 (d, J=14.4 Hz, 1H), 1.82-1.67 (m, 3H), 1.56-1.39 (m, 2H), 1.03 (s, 3H), 1.00 (s, 3H), 0.98 (s, 9H). $^{13}$C NMR (101 MHz, CDCl$_3$) δ 173.3, 157.2, 155.9, 136.5, 135.3, 130.4, 129.0, 128.8, 128.8, 123.7, 120.7, 112.2, 96.2, 77.2, 68.5, 68.5, 54.2-53.7 (m), 46.5, 38.8, 37.0, 33.2, 27.2, 26.9, 25.1, 24.4, 21.5, 15.9. HRMS (ESI) m/z [M+Na]$^+$ calculated for $C_{30}H_{40}DNO_5$: 519.2940, found 519.2935.

Benzyl (2R,4S)-2-(tert-butyl)-4-(2-(1-(4-chlorobenzoyl)-5-methoxy-3-methyl-1H-indol-2-yl)ethyl)-5-oxooxazolidine-3-carboxylate-4-d (9). The title product was prepared according to the general procedure A as colorless oil about 103 mg (85%). $^1$H NMR (400 MHz, CDCl$_3$) δ 7.62 (d, J=8.5 Hz, 2H), 7.45 (d, J=8.5 Hz, 2H), 7.33 (dd, J=5.1, 1.7 Hz, 3H), 7.24-7.15 (m, 2H), 7.00 (d, J=2.5 Hz, 1H), 6.89 (d, J=9.0 Hz, 1H), 6.67 (dd, J=9.0, 2.5 Hz, 1H), 5.56 (s, 1H), 5.26-4.97 (m, 2H), 3.81 (s, 3H), 3.16-2.87 (m, 2H), 2.29 (s, 3H), 2.17 (ddd, J=13.7, 8.9, 5.1 Hz, 2H), 0.97 (s, 9H). $^{13}$C NMR (101 MHz, CDCl$_3$) δ 172.9, 168.4, 156.1, 155.8, 139.2, 135.4, 134.7, 134.2, 131.2, 131.1, 131.0, 129.2, 128.8, 128.7, 128.4, 118.2, 115.1, 111.5, 101.2, 96.3, 77.2, 68.3, 56.4-55.9 (m), 55.8, 37.2, 33.2, 25.0, 20.9, 13.3. HRMS (ESI) m/z [M+Na]$^+$ calculated for $C_{34}H_{34}DClN_2O_6$: 626.2139, found 626.2133.

Benzyl (2R,4S)-2-(tert-butyl)-4-(((4aR,6aS,6bR,8aR,10S,12aS,14bR)-10-hydroxy-2,4a,6a,6b,9,9,12a-heptamethyl-13-oxo-1,2,3,4,4a,5,6,6a,6b,7,8,8a,9,10,11,12,12a,12b,13,14b-icosahydropicen-2-yl)methyl)-5-oxooxazolidine-3-carboxylate-4-d (10). The title product was prepared according to the general procedure A as white solid about 70 mg (50%). $^1$H NMR (400 MHz, CDCl$_3$) δ 7.34 (qq, J=5.0, 2.1 Hz, 5H), 5.63 (d, J=44.5 Hz, 1H), 5.54 (d, J=2.8 Hz, 1H), 5.24-4.99 (m, 2H), 3.21 (dt, J=10.6, 4.7 Hz, 1H), 2.92-2.66 (m, 1H), 2.32 (d, J=3.1 Hz, 1H), 2.14 (tt, J=12.4, 6.3 Hz, 1H), 2.01 (dt, J=21.3, 7.9 Hz, 1H), 1.78 (ddd, J=27.1, 14.0, 6.3 Hz, 2H), 1.69-1.51 (m, 5H), 1.48-1.30 (m, 8H), 1.31-1.20 (m, 2H), 1.22-1.07 (m, 9H), 1.04-0.90 (m, 16H), 0.82 (d, J=20.5 Hz, 6H), 0.74-0.60 (m, 1H). $^{13}$C NMR (101 MHz, CDCl$_3$) δ 200.3, 200.2, 173.3, 173.0, 170.2, 169.5, 155.9, 155.8, 135.3, 135.2, 129.0, 128.9, 128.9, 128.8, 128.5, 128.4, 96.3, 96.2, 78.9, 78.9, 77.2, 68.5 (2C), 61.9, 61.8, 55.1, 55.0, 53.6-53.3 (m), 49.9, 47.1, 46.7, 45.6, 45.5, 43.8, 43.6, 43.5, 43.5, 39.3, 39.2, 37.2, 37.2, 37.0, 37.0, 36.0 (2C), 34.4, 33.8, 33.0, 32.9, 32.9, 32.5, 32.2, 31.8, 29.8 (2C), 28.8 (2C), 28.2, 27.4, 26.5 (2C), 25.1, 23.6, 23.5, 21.3, 18.8 (2C), 17.6, 16.5, 15.7, 15.7. HRMS (ESI) m/z [M+Na]$^+$ calculated for $C_{45}H_{64}DNO_6$: 739.4767, found 739.4762.

Example 3. Preparation of Deuterated Amino Acids

The synthesized compounds 3 may be conveniently transformed into α-deuterated α-amino acids, as showcased in the synthesis of α-deuterated leucine (Leu, 11) by reacting with concentrated HCl for 30 minutes without the erosion of deuteration level (Scheme 3).

Scheme 3. Synthesis of α-deuterated Leu

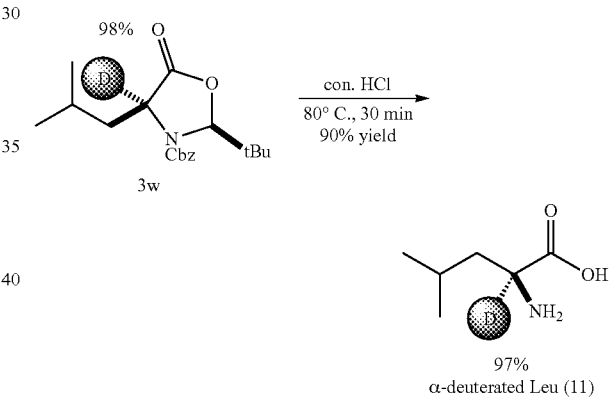

To a round bottom flask equipped with a stir bar was added benzyl (2S,4S)-2-(tert-butyl)-4-isobutyl-5-oxooxazolidine-3-carboxylate (12 mg), and concentrated aqueous HCl (2 mL). The reaction was stirred at 80° C. for 30 minutes then concentrated by rotary evaporation to afford the product (4.3 mg, 90%) as a white solid. The physical properties and spectral data are consistent with the values of commercially available Leu.

Deuterated aspartic acid (Asp) was also produced (Scheme 4).

Scheme 4. Synthesis of α-deuterated Asp

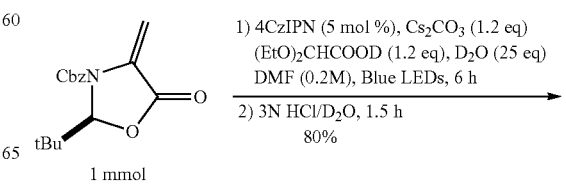

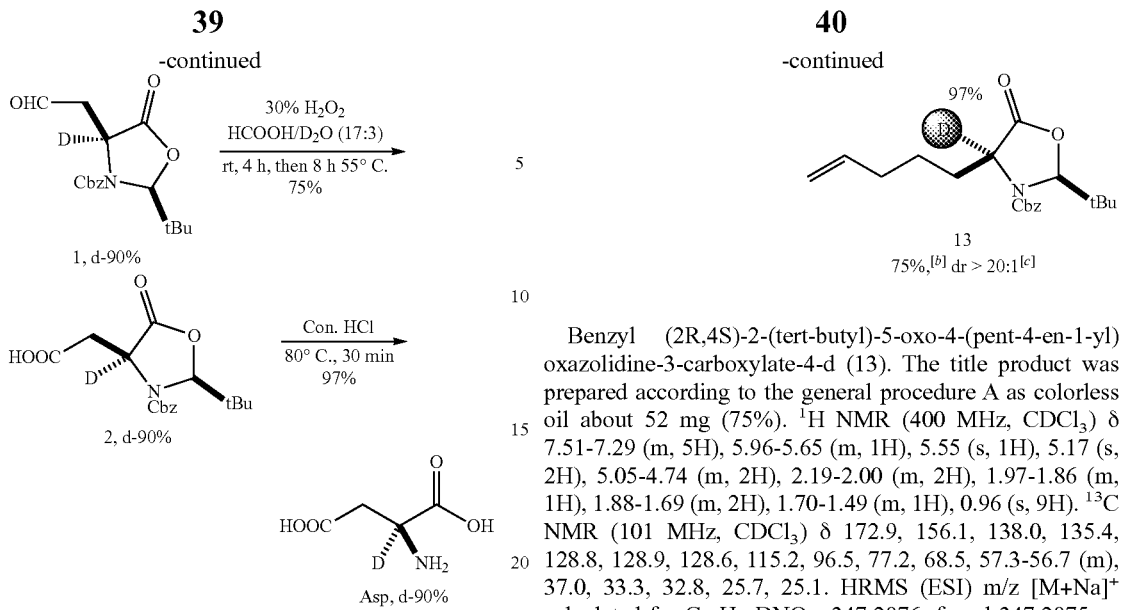

Step 1. Compound 1 was prepared according to the general procedure A, and the amount of chiral dehydroalanine was up to the scale of 1 mmol (300 mg). After already obtained benzyl (2S,4S)-2-(tert-butyl)-4-(2,2-diethoxyethyl)-5-oxooxazolidine-3-carboxylate via purification, the compound was dissolved in 5 mL DMF, and 5 mL 3 N HCl in deuterium oxide was applied similar to the previous literature, stirred at rt for 1.5 h to provide the desired compound 1 about 265 mg (80%).

Step 2. To 5 mL round bottom flask, 0.01 mmol compound 1 was dissolved in 1 mL formic acid/deuterium oxide (17:3), and then 30% $H_2O_2$ was added at rt for 4 h and solid formed during the reaction; and then put the reactions system in oil bath at 50-55° C. for about 8 h. After the completion of the reaction, removed the solvent purified by column chromatograph to obtain the desired product 240 mg (75%) as colorless oil.

Step 3. 2-((2S,4S)-3-((benzyloxy)carbonyl)-2-(tert-butyl)-5-oxooxazolidin-4-yl)acetic acid 2 (0.1 mmol) was suspended in concentrated HCl and heated to 80° C. for 30 min, and then the HCl was removed to provide the pure solid product 151 mg (97%).

Radical clock experiments-cyclopropyl ring-opening (12) by forming alkenyl derived amino acid 13 suggest the presence of alkyl radicals (Scheme 5), which is consistent with previously reported decarboxylative coupling studies.

Scheme 5. Radical clock reaction

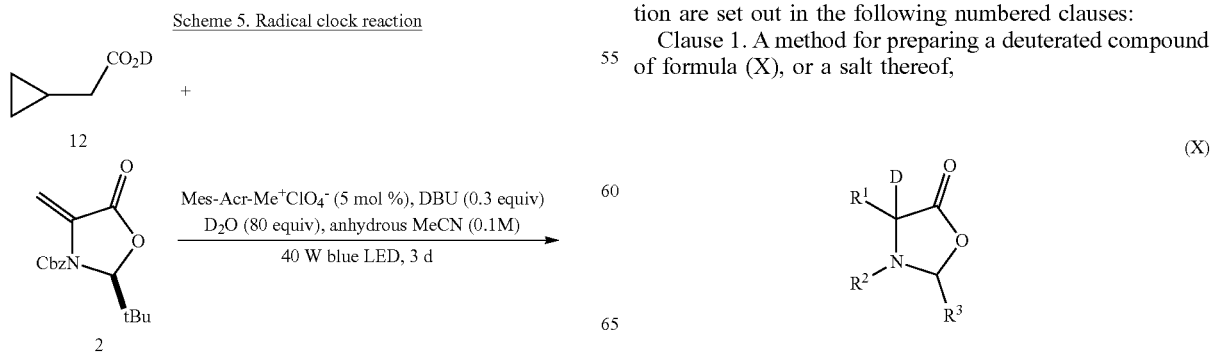

Benzyl (2R,4S)-2-(tert-butyl)-5-oxo-4-(pent-4-en-1-yl)oxazolidine-3-carboxylate-4-d (13). The title product was prepared according to the general procedure A as colorless oil about 52 mg (75%). $^1$H NMR (400 MHz, CDCl$_3$) δ 7.51-7.29 (m, 5H), 5.96-5.65 (m, 1H), 5.55 (s, 1H), 5.17 (s, 2H), 5.05-4.74 (m, 2H), 2.19-2.00 (m, 2H), 1.97-1.86 (m, 1H), 1.88-1.69 (m, 2H), 1.70-1.49 (m, 1H), 0.96 (s, 9H). $^{13}$C NMR (101 MHz, CDCl$_3$) δ 172.9, 156.1, 138.0, 135.4, 128.8, 128.9, 128.6, 115.2, 96.5, 77.2, 68.5, 57.3-56.7 (m), 37.0, 33.3, 32.8, 25.7, 25.1. HRMS (ESI) m/z [M+Na]$^+$ calculated for $C_{20}H_{26}DNO_4$: 347.2076, found 347.2075.

In summary, a mild, versatile organophotoredox protocol was developed for the preparation of diverse, enantioenriched, α-deuterated α-amino acids. The distinct radical approach represents a significant departure from the two-electron transformations so often prescribed in the literature. This radical-based strategy offers the unrivaled capacity of the convergent unification of readily accessible feedstock carboxylic acids and a chiral methyleneoxazolidinone fragment and highly diastereo-, chemo- and regio-selective incorporation of deuterium simultaneously, which could vastly expand the domain of highly biologically and medicinally valued α-deuterated amino acids. Furthermore, the present method has addressed the long-standing challenge of the installation of sterically bulky side chains into α-amino acids. Due to its simplicity and efficiency, the present method may rapid access to highly sought amino acid building blocks in medicinal chemistry.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method for preparing a deuterated compound of formula (X), or a salt thereof, wherein
R¹ is alkyl, —C(O)alkyl, alkenyl, —C(O)alkyenyl, cycloalkyl, —C(O)cycloalkyl, cycloalkenyl, —C(O)cycloalkenyl, aryl, —C(O)aryl, heteroaryl, —C(O)heteroaryl, heterocyclyl, or —C(O)heterocyclyl, wherein R¹ is optionally substituted with one or more $R^a$;

R² is H or an amino protecting group;

R³ is —$CR^bR^cR^d$;

$R^a$ at each occurrence is independently halogen, —CN, —OH, nitro, a protected hydroxyl, a protected amino, or —X—$R^X$, wherein X is bond, O, NH, C(O), OC(O), or C(O)NH; and $R^X$ is alkyl, alkenyl, alkynyl, alkoxy, cycloalkyl, aryl, heteroaryl, or heterocyclyl, wherein the $R^X$ is optionally substituted;

$R^b$, $R^c$, and $R^d$ are independently H, alkyl, or $R^b$ and $R^c$ together with the carbon they are attached to form a ring;

the method comprising:

(i) mixing R¹—COOD with a compound of formula (II), a base, and a photocatalyst in an essentially H₂O free solvent comprising D₂O and an organic solvent to form a mixture; and

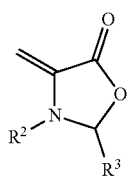

(II)

(ii) exposing the mixture of (i) to light, thereby producing the deuterated compound of formula (I), or a salt thereof.

Clause 2. The method of clause 1, wherein R² is carbobenzyloxy (Cbz), butyloxycarbonyl (Boc), 9-fluorenylmethyloxycarbonyl (Fmoc), 2,2,2-trichloroethyloxycarbonyl (Troc), or allyloxycarbonyl (Alloc).

Clause 3. The method of any one of clauses 1-2, wherein $R^b$, $R^c$, and $R^d$ are each independently $C_{1-4}$alkyl.

Clause 4. The method of any one of clauses 1-3, wherein formula (II) is formula (II-a)

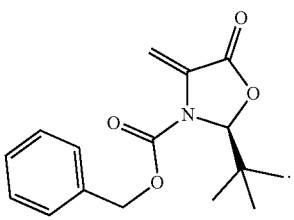

(II-a)

Clause 5. The method of any one of clauses 1-4, wherein the photocatalyst is

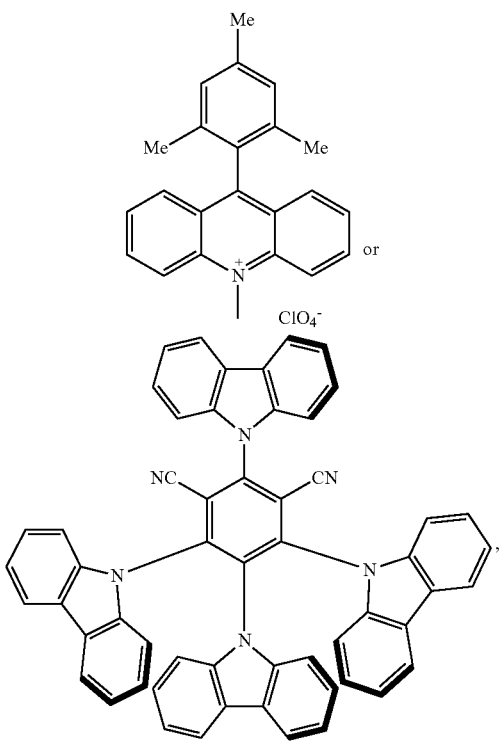

or a salt thereof.

Clause 6. The method of any one of clauses 1-5, wherein the essentially H₂O free solvent is a combination of D₂O and an anhydrous organic solvent.

Clause 7. The method of any one of clauses 1-6, wherein the organic solvent is acetonitrile, dimethylformamide, dichloroethane, or a combination thereof.

Clause 8. The method of any one of clauses 1-7, wherein the base is 1,8-diazabicyclo[5.4.0]undec-7-ene, Cs₂CO₃, or a combination thereof.

Clause 9. The method of any one of clauses 1-8, wherein R¹ is

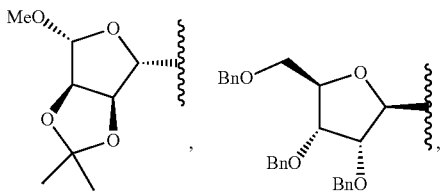

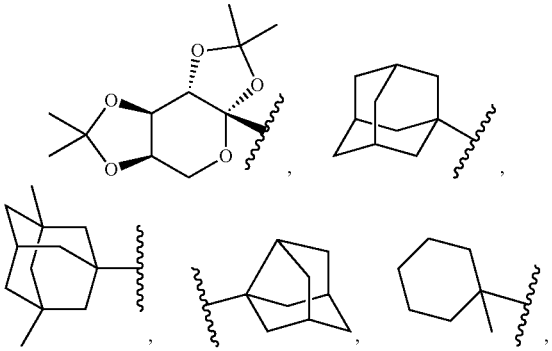

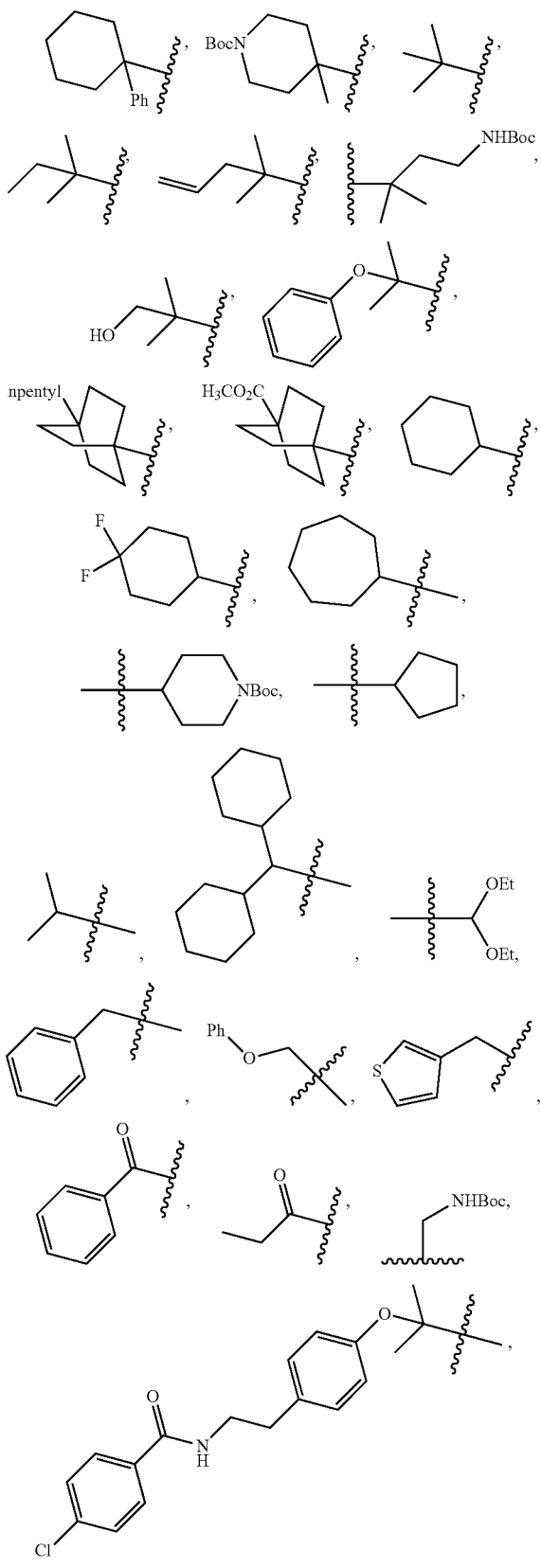

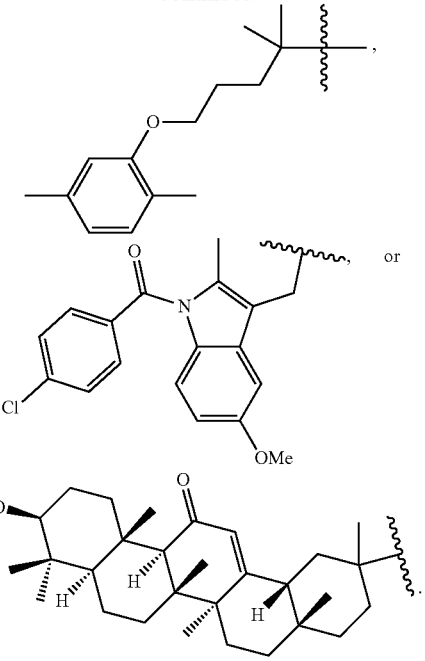

Clause 10. The method of any one of clauses 1-9, wherein in the level of deuterium incorporation of the deuterated compound of formula (X), or a salt thereof, is at least 90%.

Clause 11. The method of clause 10, wherein in the level of deuterium incorporation of the deuterated compound of formula (X), or a salt thereof, is at least 95%.

Clause 12. The method of any one of clauses 1-11, further comprising isolating the deuterated compound of formula (X), or a salt thereof.

Clause 13. A deuterated compound of formula (X), or a salt thereof,

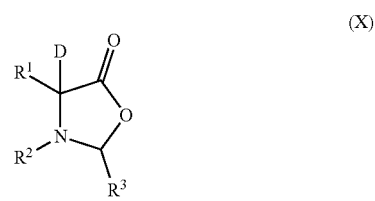

wherein
R¹ is alkyl, —C(O)alkyl, alkenyl, —C(O)alkyenyl, cycloalkyl, —C(O)cycloalkyl, cycloalkenyl, —C(O)cycloalkenyl, aryl, —C(O)aryl, heteroaryl, —C(O)heteroaryl, heterocyclyl, or —C(O)heterocyclyl, wherein R¹ is optionally substituted with one or more $R^a$;

R² is H or an amino protecting group;

R³ is —$CR^bR^cR^d$;

$R^a$ at each occurrence is independently halogen, —CN, —OH, nitro, a protected hydroxyl, a protected amino, or —X—$R^X$, wherein X is bond, O, NH, C(O), OC(O), or C(O)NH; and $R^X$ is alkyl, alkenyl, alkynyl, alkoxy, cycloalkyl, aryl, heteroaryl, or heterocyclyl, wherein the $R^X$ is optionally substituted;

$R^b$, $R^c$, and $R^d$ are independently H, alkyl, or $R^b$ and $R^c$ together with the carbon they are attached to form a ring.

Clause 14. The compound of clause 13, or a salt thereof, wherein $R^2$ is carbobenzyloxy (Cbz), butyloxycarbonyl (Boc), 9-fluorenylmethyloxycarbonyl (Fmoc), 2,2,2-trichloroethyloxycarbonyl (Troc), or allyloxycarbonyl (Alloc).

Clause 15. The compound of any one of clauses 13-14, or a salt thereof, wherein $R^b$, $R^c$, and $R^d$ are each independently $C_{1-4}$alkyl.

Clause 16. The compound of any one of clauses 13-15, having a structure of formula (X-a), or a salt thereof

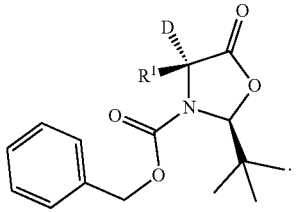

(X-a)

Clause 17. The compound of any one of clauses 13-16, selected from the group consisting of

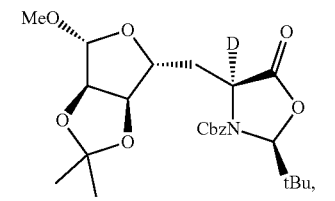

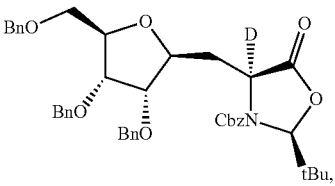

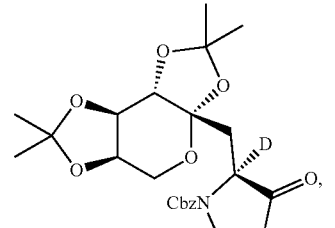

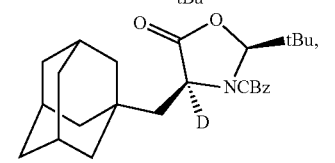

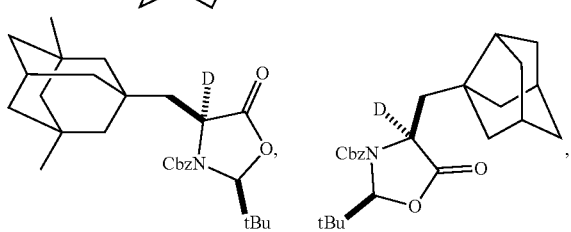

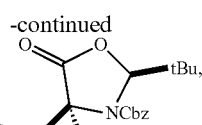

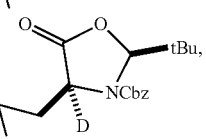

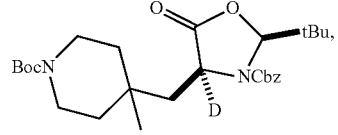

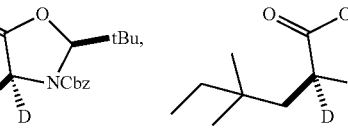

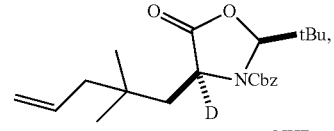

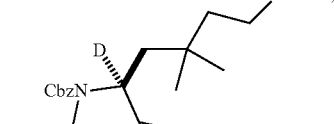

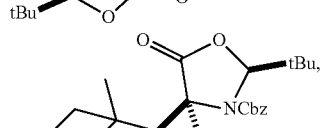

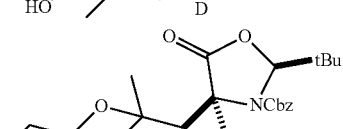

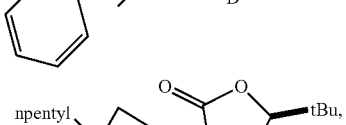

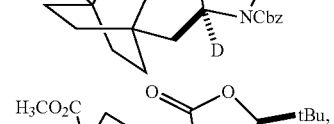

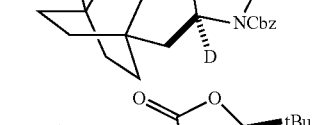

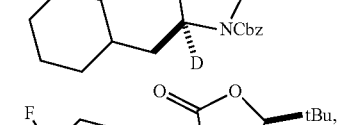

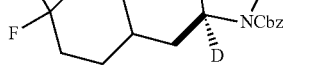

-continued

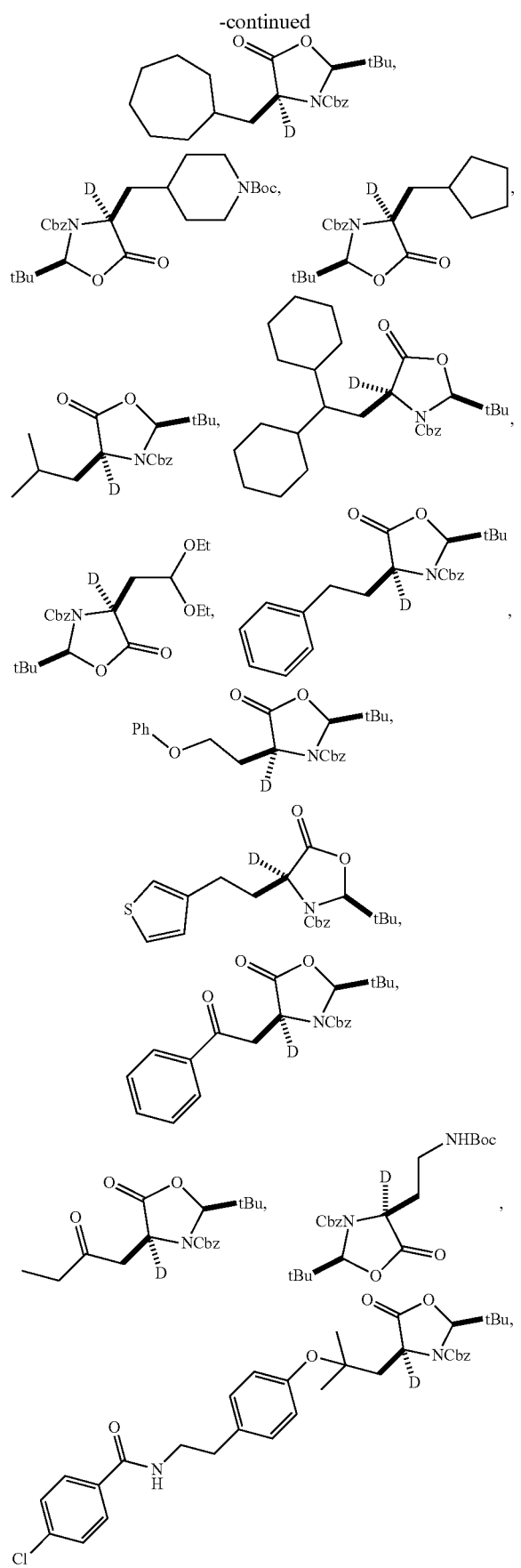

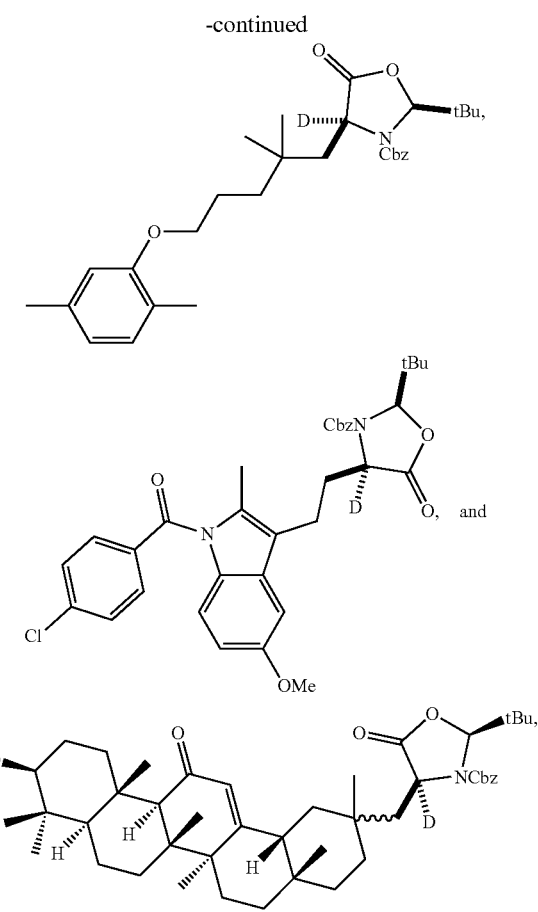

or a salt thereof.

Clause 18. A method of preparing a deuterated amino acid, comprising preparing a deuterated compound of formula (X), or a salt thereof, according to the method of clause 1; and converting the deuterated compound of formula (X), or a salt thereof, to an amino acid having a structure of formula (III), or a salt thereof,

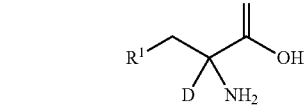
(III)

wherein $R^1$ is as defined in clause 1.

Clause 19. The method of clause 18, wherein $R^1$ is

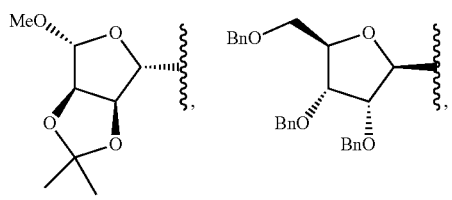

-continued

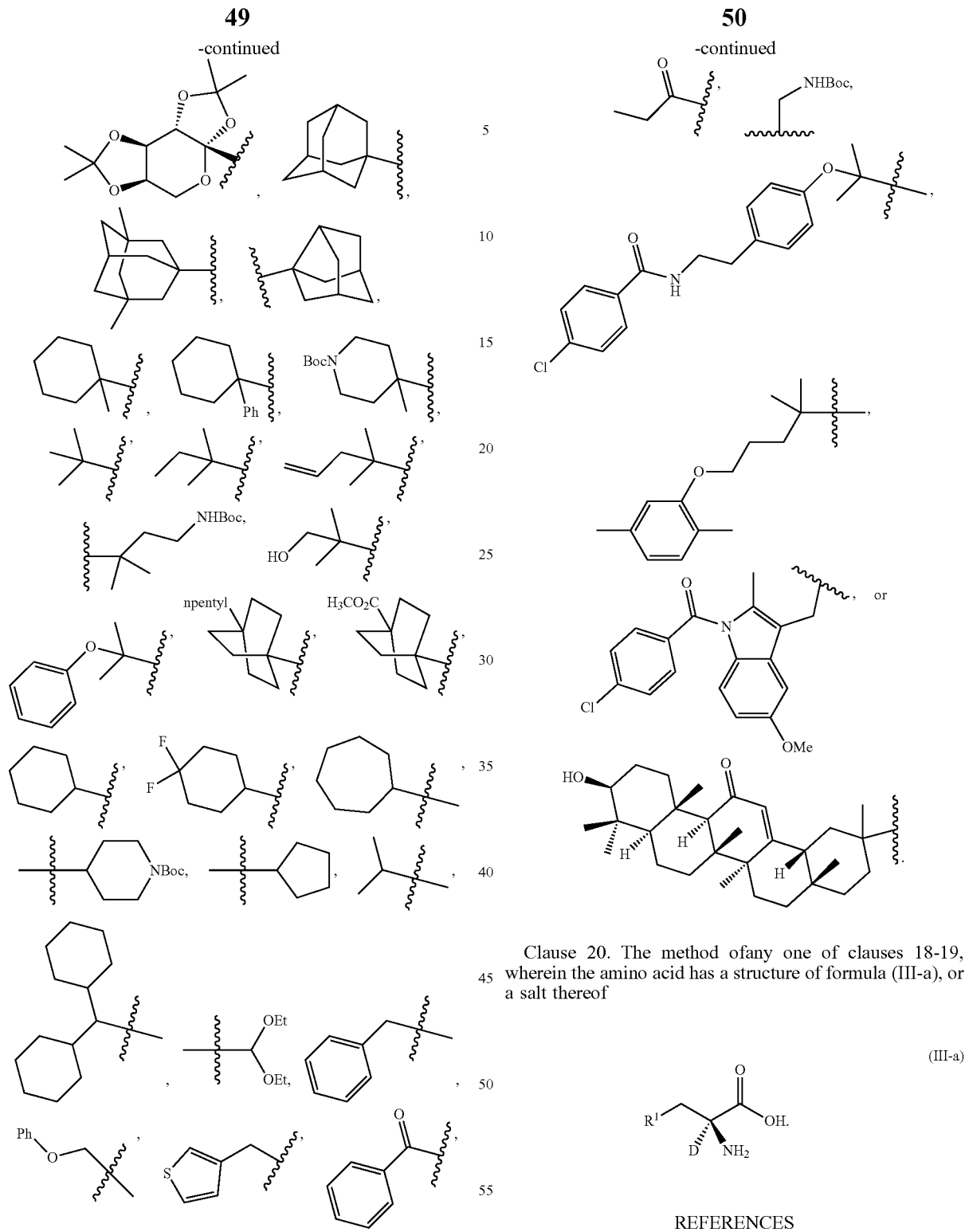

Clause 20. The method of any one of clauses 18-19, wherein the amino acid has a structure of formula (III-a), or a salt thereof

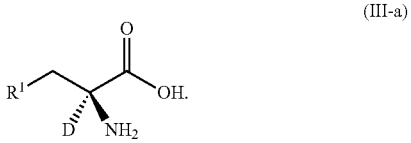

(III-a)

REFERENCES

01  Atzrodt, J.; Derdau, V.; Kerr, W. J.; Reid, M. C-H Functionalisation for Hydrogen Isotope Exchange. Angew. Chem., Int. Ed. 2018, 57, 3022.
02  Atzrodt, J.; Derdau, V.; Kerr, W. J.; Reid, M. Deuterium- and Tritium-Labelled Compounds: Applications in the Life Sciences. Angew. Chem. Int. Ed. 2018, 57, 1758.
03  Axon, J. R.; Beckwith, A. L. J. Diastereoselective radical addition to methyleneoxazolidinones: an enantioselective route to α-amino acids. J. Chem. Soc. Chem. Commun. 1995, 549.

| | |
|---|---|
| 04 | Aycock, R. A.; Pratt, C. J.; Jui, N. T. Aminoalkyl Radicals as Powerful Intermediates for the Synthesis of Unnatural Amino Acids and Peptides. ACS Catal. 2018, 8, 9115-9119. |
| 05 | Aycock, R. A.; Vogt, D. B.; Jui, N. T. A practical and scalable system for heteroaryl amino acid synthesis. Chem. Sci. 2017, 8, 7998-8003. |
| 06 | Baldwin, J. E.; Adlington, R. M.; Marquess, D. G.; Pitt, A. R.; Porter, M. J.; Russell, A. T. Evidence for an insertion-homolysis mechanism for carbon-sulphur bond formation in penicillin biosynthesis; 1. Synthesis of tripeptide probes. Tetrahedron, 1996, 52, 2515. |
| 07 | Bhatia, S.; Sphlinger, G.; Boukhumseen, N.; Boll, Q.; Li, Z.; Jackson, J. E. Stereoretentive H/D Exchange via an Electroactivated Heterogeneous Catalyst at $sp^3$C-H Sites Bearing Amines orAlcohols. Eur. J. Org. Chem. 2016, 4230. |
| 08 | Chatterjee, B.; Krishnakumar, V.; Gunanathan, C. Selective α-Deuteration of Amines and Amino Acids Using $D_2O$. Org. Lett. 2016, 18, 5892. |
| 09 | Chen, J.-R.; Hu, X.-Q.; Lu, L.- Q.; Xiao, W.-J. Visible light photoredox-controlled reactions of N-radicals and radical ions. Chem. Soc. Rev. 2016, 45, 2044. |
| 10 | Church, N. J.; Young, D. W. Synthesis of the suicide substrate D-propargylglycine stereospecifically labelled with deuterium and investigation of its oxidation by D-amino acid oxidase. J. Chem. Soc. Perkin Trans. 1. 1998, 52, 1475. |
| 11 | Cowell, S. M.; Lee, Y. S.; Cain, J. P.; Hruby, V. J. Exploring Ramachandran and chi space: conformationally constrained amino acids and peptides in the design of bioactive polypeptide ligands. Curr. Med. Chem. 2004, 11, 2785. |
| 12 | deGruyter, J. N.; Malins, L. R.; Baran, P. S. Residue-Specific Peptide Modification: A Chemist's Guide. Biochemistry 2017, 56, 3863. |
| 13 | Easton, C. J. Free-Radical Reactions in the Synthesis of α-Amino Acids and Derivatives. Chem. Rev. 1997, 97, 53. |
| 14 | Elemes, Y.; Ragnarsson, U. Synthesis of enantiopure α-deuteriated Boc-L-amino acids. J. Chem. Soc. Perkin Trans. 1. 1996. 537. |
| 15 | Faleev, N. G.; Ruvinov, S. B.; Saporovskaya, M. B.; Belikov, V. M.; Zakomyrdina, L. N.; Sakharova, I. S.; Torchinsky, Y. M. Preparation of α-deuterated L-amino acids using E. coli B/It7-A cells containing tryptophanase. Tetrahedron Lett. 1990, 31, 7051. |
| 16 | Furuta, T.; Takahashi, H.; Kasuya, Y. Evidence for a carbanion intermediate in the elimination of ammonia from L-histidine catalyzed by histidine ammonia-lyase. J. Am Chem. Soc. 1990, 112, 3633. |
| 17 | Gant, T. G. Using Deuterium in Drug Discovery: Leaving the Label in the Drug. J. Med. Chem. 2014, 57, 3595. |
| 18 | Gardner, K. H.; Kay, L. E. Production and Incorporation of $^{15}N$, $^{13}C$, $^{2}H$ ($^{1}H$-δ1 Methyl) Isoleucine into Proteins for Multidimensional NMR Studies. J. Am. Chem. Soc. 1997, 119, 7599. |
| 19 | Geng, H.; Chen, X.; Gui, J.; Zhang, Y.; Shen, Z.; Qian, P.; Chen, J.; Zhang, S.; Wang, W. Practical synthesis of C1 deuterated aldehydes enabled by NHC catalysis. Nature Catal. 2019, 2, 1071. |
| 20 | Halab, L.; Gosselin, F.; Lubell, W. D. Design, synthesis, and conformational analysis of azacycloalkane amino acids as conformationally constrained probes for mimicry of peptide secondary structures. Peptide Sci. 2000, 55, 101. |
| 21 | Hale, L. V. A.; Szymczak, N. K. Stereoretentive Deuteration of α-Chiral Amines with $D_2O$. J. Am. Chem. Soc. 2016, 138, 13489. |
| 22 | Hopkinson, M. N.; Sahoo, B.; Li, J.- L.; Glorius, F. Dual Catalysis Sees the Light: Combining Photoredox with Organo-, Acid, and Transition-Metal Catalysis. Chem. Eur. J. 2014, 20, 3874. |
| 23 | Huang, H.; Jia, K.; Chen, Y. Radical Decarboxylative Functionalizations Enabled by Dual Photoredox Catalysis. ACS Catal. 2016, 6, 4983. |
| 24 | Huang, H.; Yu, C.-G.; Zhang, Y.-T.; Zhang, Y.-Q.; Mariano, P. S.; Wang, W. Chemo- and Regioselective Organo-Photoredox Catalyzed Hydroformylation of Styrenes via a Radical Pathway. J. Am. Chem. Soc. 2017, 139, 9799-9802. |
| 25 | Jacques, V.; Czarnik, A. W.; Judge, T. M.; Van der Ploeg, L. H.; DeWitt, S. H. Differentiation of antiinflammatory and antitumorigenic properties of stabilized enantiomers of thalidomide analogs. Proc. Natl. Acad. Sci. U.S.A. 2015, 112, E1471. |
| 26 | Jamison, C. R.; Overman, L. E. Fragment Coupling with Tertiary Radicals Generated by Visible-Light Photocatalysis. Acc. Chem. Res. 2016, 49, 1578. |
| 27 | Jere, F. T.; Miller, D. J.; Jackson, J. E. Stereoretentive C-H Bond Activation in the Aqueous Phase Catalytic Hydrogenation of Amino Acids to Amino Alcohols. Org. Lett. 2003, 5, 527. |
| 28 | Ji, P.; Zhang, Y.; Wei, Y.; Huang, H.; Hu, W.; Mariano, P. S.; Wang, W. Visible-Light-Mediated, Chemo- and Stereoselective Radical Process for the Synthesis of C-Glycoamino Acids. Org. Lett. 2019, 21, 3086. |
| 29 | Jin, Y.; Fu, H. Visible-Light Photoredox Decarboxylative Couplings. Asian J. Org. Chem. 2017, 6, 368. |
| 30 | Koike, T.; Akita, M. Trifluoromethylation by Visible-Light-Driven Photoredox Catalysis. Top. Catal. 2014, 57, 967. |
| 31 | Koniarczyk, J.; Hesk, D.; Overgard, A.; Davies, I. W.; McNally, A. A General Strategy for Site-Selective Incorporation of Deuterium and Tritium into Pyridines, Diazines, and Pharmaceuticals. J. Am. Chem. Soc. 2018, 140, 1990. |

| | |
|---|---|
| 32 | Lastra, E.; Hegedus, L. S. Synthesis of compounds containing two adjacent carbon-13 labels by photolytic reactions of chromium carbene complexes. J. Am. Chem. Soc. 1993, 115, 87. |
| 33 | Lian, L.-Y. Middleton, D. A. Labelling approaches for protein structural studies by solution-state and solid-state NMR. Prog. Nucl. Msgn. Reson. Spectrosc. 2001, 39, 171. |
| 34 | Liang, X.; Duttwyler, S. Efficient Brønsted-Acid-Catalyzed Deuteration of Arenes and Their Transformation to Functionalized Deuterated Products. Asian J. Org. Chem. 2017, 6, 1063. |
| 35 | Liu, Q.; Wu, L.-Z. Recent advances in visible-light-driven organic reactions. Natl. Sci. Rev. 2017, 4, 359. |
| 36 | Loh, Y. Y.; Nagao, K. A.; Hoover, J.; Hesk, D.; Rivera, N. R.; Colletti, S. L.; Davies, I. W.; MacMillan, D. W. C. Photoredox-catalyzed deuteration and tritiation of pharmaceutical compounds. Science 2017, 358, 1182. |
| 37 | Lygo, B.; Humphreys, L. D. Enantioselective synthesis of α-carbon deuterium-labelled L-α-amino acids. Tetrahedron Lett. 2002, 43, 6677. |
| 38 | Maegawa, T.; Akashi, A.; Esaki, H.; Aoki, F.; Sajiki, H.; Hirota, K. Palladium-Catalyzed Base-Selective H-D Exchange Reaction of Nucleosides in Deuterium Oxide. Synlett. 2005, 5, 845. |
| 39 | Maltais, F.; Jung, Y. C.; Chen, M.; Tanoury, J.; Perni, R. B.; Mani, N.; Laitinen, L.; Huang, H.; Liao, S.; Gao, H.; Tsao, H.; Block,; Ma, E. C.; Shawgo, R. S.; Town, C.; Brummel, C. L.; Howe, D.; Pazhanisamy, S.; Raybuck, S.; Namchuk, M.; Bennani, Y. L. In Vitro and In Vivo Isotope Effects with Hepatitis C Protease Inhibitors: Enhanced Plasma Exposure of Deuterated Telaprevir versus Telaprevir in Rats. J. Med. Chem. 2009, 52, 7993. |
| 40 | Meggers, E. Asymmetric catalysis activated by visible light. Chem. Commun. 2015, 51,3290. |
| 41 | Michelotti, A.; Roche, M. 40 Years of Hydrogen-Deuterium Exchange Adjacent to Heteroatoms: A Survey. Synthesis. 2019, 51, 1319. |
| 42 | Michelotti, A.; Rodrigues, F.; Roche, M. Development and Scale-Up of Stereoretentive α-Deuteration of Amines. Org. Process Res. Dev. 2017, 21, 1741. |
| 43 | Milne, J. J.; Malthouse, J. P. G. Enzymatic synthesis of α-deuterated amino acids. Biochem. Soc. Trans. 1996, 24, 133S. |
| 44 | Moozeh, K.; So, S. M.; Chin, J. Catalytic Stereoinversion of L-Alanine to Deuterated D-Alanine. Angew. Chem., Int. Ed. 2015, 54, 9381. |
| 45 | Nagatomo, M.; Kamimura, D.; Matsui, Y.; Masuda, K.; Inoue, M. Et$_3$B-mediated two- and three-component coupling reactions via radical decarbonylation of α-alkoxyacyl tellurides: single-step construction of densely oxygenated carboskeletons. Chem. Sci. 2015, 6, 2765. |
| 46 | Narayanam, J. M. R.; Stephenson, C. R. J. Visible light photoredox catalysis: applications in organic synthesis. Chem. Soc. Rev. 2011, 40, 102. |
| 47 | Oh, J.-S.; Kim, K.; Song, C. E. Enantioselective synthesis of α-deuterium labelled chiral α-amino acids via dynamic kinetic resolution of racemic azlactones. Org. Biomol. Chem. 2011, 9, 7983. |
| 48 | Pirali, T.; Serafini, M.; Cargnin, S.; Genazzani, A. A. Applications of Deuterium in Medicinal Chemistry. J. Med. Chem. 2019, 62, 5276. |
| 49 | Prier, C. K.; Rankic, D. A.; MacMillan, D. W. C. Visible Light Photoredox Catalysis with Transition Metal Complexes: Applications in Organic Synthesis. Chem. Rev. 2013, 113, 5322. |
| 50 | Puleo, T. R.; Strong, A. J.; Bandar, J. S. Catalytic α-Selective Deuteration of Styrene Derivatives. J. Am. Chem. Soc. 2019, 141, 1467. |
| 51 | Raap, J.; Nieuwenhuis, S.; Creeners, A.; Hexspoor, S.; Kragl, U.; Lugtenburg, J. Synthesis of Isotopically Labelled L-Phenylalanine and L-Tyrosine. Eur. J. Org. Chem. 1999, 10, 2609. |
| 52 | Romero, N. A.; Nicewicz, D. A. Organic Photoredox Catalysis. Chem. Rev. 2016, 116, 10075. |
| 53 | Rose, J. E.; Leeson, P. D.; Gani, D. J Mechanisms and stereochemistry of the activation of (2S)- and (2R)-serine O-sulfate as suicide inhibitors for *Escherichia coli* glutamic acid decarboxylase. J. Chem. Soc. Chem. Commun. 1992, 1784. |
| 54 | Rose, J. E.; Leeson, P. D.; Gani, D. Stereospecific synthesis of α-deuteriated α-amino acids: regiospecific deuteriation of chiral 3-isopropyl-2,5-dimethoxy-3,6-dihydropyrazines. J. Chem. Soc. Perkin Trans. 1995, 157. |
| 55 | Sack, I.; Balazs, Y. S.; Rahimipour, S.; Vega, S. Solid-State NMR Determination of Peptide Torsion Angles: Applications of $^2$H-Dephased REDOR. J. Am. Chem. Soc. 2000, 122, 12263. |
| 56 | Sattler, A. Hydrogen/Deuterium (H/D) Exchange Catalysis in Alkanes. ACS Catal. 2018, 8, 2296. |
| 57 | Shen, Z.; Zhang, S.; Geng, H.; Wang, J.; Zhang, X.; Zhou, A.; Yao, C.; Chen, X.; Wang, W. Trideuteromethylation Enabled by a Sulfoxonium Metathesis Reaction. Org. Lett. 2019, 21, 448. |
| 58 | Sibi, M. P.; Asano, Y.; Sausker, J. B. Enantioselective Hydrogen Atom Transfer Reactions: Synthesis of N-Acyl-alpha-Amino Acid Esters This work was supported by the National Institutes of Health (NIH-GM-54656). Angew. Chem., Int. Ed. 2001, 40, 1293. |

59 Sim, J.; Campbell, M. W.; Molander, G. A. Synthesis of α-Fluoro-α-amino Acid Derivatives via Photoredox-Catalyzed Carbofluorination. ACS. Catal. 2019, 9, 1558.
60 Simmons, E. M.; Hartwig, J. F. On the interpretation of deuterium kinetic isotope effects in C-H bond functionalizations by transition-metal complexes. Angew. Chem., Int. Ed. 2012, 51, 3066.
61 Skubi, K. L.; Blum, T. R.; Yoon, T. P. Dual Catalysis Strategies in Photochemical Synthesis. Chem. Rev. 2016, 116, 10035.
62 Stevenson, D. E.; Akhtar, M.; Gani, D. Structural and stereochemical studies of methiomine decarboxylase from dryopteris felix-mas. Tetrahedron Lett. 1986, 27, 5661.
63 Taglang, C.; Korenchan, D. E.; Morze, C.; Yu, J.; Najac, C.; Wang, S.; Blecha, J. E.; Subramaniam, S.; Bok, R.; VanBrocklin, H. F.; Vigneron, D. B.; Ronen, S. M.; Sriram, R.; Kurhanewicz, J. D.; Wilson, M.; Flavell, R. R. Late-stage deuteration of 13C-enriched substrates for Tl prolongation in hyperpolarized $^{13}$C MRI. Chem. Commun. 2018, 54, 5233.
64 Taglang, C.; Martinez-Prieto, L. M.; Rosal, I.; Maron, L.; Poteau, R.; Philippot, K.; Chaudret, B.; Perato, S.; Lone, A. S.; Puente, C.; Dugabe, C.; Rousseau, B.; Pieters, G. Enantiospecific C-H Activation Using Ruthenium Nanocatalysts. Angew. Chem., Int. Ed. 2015, 54, 10474.
65 Takeda, R.; Abe, H.; Shibata, N.; Moriwaki, H.; Izawa, K.; Soloshonok, V. A. Asymmetric synthesis of α-deuterated α-amino acids. Org. Biomol. Chem. 2017, 15, 6978.
66 Taylor, P. J. M.; Bull, S. D. An improved synthesis of deuterated Schöllkopf's bis-lactim ether and its use for the asymmetric synthesis of (R)-[α-$^2$H]-phenylalanine methyl esters. Tetrahedron: Asymmetry. 2006, 17, 1170.
67 Tellis, J. C.; Kelly, C. B.; Primer, D. N.; Jouffroy, M.; Patel, N. R.; Molander, G. A. Single-Electron Transmetalation via Photoredox/Nickel Dual Catalysis: Unlocking a New Paradigm for sp$^3$-sp$^2$ Cross-Coupling. Acc. Chem. Res. 2016, 49, 1429.
68 Valero, M.; Weck, R.; Gssregen, S.; Atzrodt, J.; Derdau, V. Highly Selective Directed Iridium-Catalyzed Hydrogen Isotope Exchange Reactions of Aliphatic Amides. Angew. Chem., Int. Ed. 2018, 57, 8159.
69 Wang, C.- S.; Dixneuf, P. H.; Soulé, J.- F. Photoredox Catalysis for Building C-C Bonds from C(sp$^2$)-H Bonds. Chem. Rev. 2018, 118, 7532.
70 Wang, X.; Zhu, M.- H.; Schuman, D. P.; Zhong, D.; Wang, W.- Y.; Wu, L.- Y.; Liu, W.; Stoltz, B. M.; Liu, W.- B. General and Practical Potassium Methoxide/Disilane-Mediated Dehalogenative Deuteration of (Hetero)Arylhalides. J. Am. Chem. Soc. 2018, 140, 10970.
71 Wong, C. H.; Whitesides, G. M. Enzyme-catalyzed organic synthesis: regeneration of deuterated nicotinamide cofactors for use in large-scale enzymatic synthesis of deuterated substances. J. Am. Chem. Soc. 1983, 105, 5012.
72 Xuan, J.; Zhang, Z.- G.; Xiao, W.- J. Visible-Light-Induced Decarboxylative Functionalization of Carboxylic Acids and Their Derivatives. Angew. Chem., Int. Ed. 2015, 54, 15632.
73 Yamamoto, T.; Tokunaga, E.; Nakamura, S.; Shibata, N.; Toru, T. Synthesis and configurational stability of (S)- and (R)-deuteriothalidomides. Chem. Pharm. Bull. 2010, 58, 110.
74 Yan, M.; Lo, J. C.; Edwards, J. T.; Baran, P. S. Radicals: Reactive Intermediates with Translational Potential. J. Am. Chem. Soc. 2016, 138, 12692.
75 Yang, J. in Deuterium: Discovery and Applications in Organic Chemistry, Elsevier, Amsterdam, 2016, pp. 1.
76 Yu, R. P.; Hesk, D.; Rivera, N.; Pelczer, I.; Chirik, P. J. Iron-catalysed tritiation of pharmaceuticals. Nature 2016, 529, 195.
77 Zhou, R.; Li, J.; Cheo, H. W.; Chua, R.; Zhan, G.; Hou, Z.; Wu, J. Visible-light-mediated deuteration of silanes with deuterium oxide. Chem. Sci. 2019, 10, 7340.

What is claimed is:

1. A method for preparing a deuterated compound of formula (I), or a salt thereof,

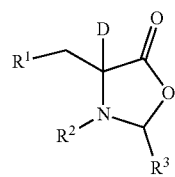

wherein $R^1$ is alkyl, —C(O)alkyl, alkenyl, —C(O)alkyenyl, cycloalkyl, —C(O)cycloalkyl, cycloalkenyl, —C(O)cycloalkenyl, aryl, —C(O)aryl, heteroaryl, —C(O)heteroaryl, heterocyclyl, or —C(O)heterocyclyl, wherein $R^1$ is optionally substituted with one or more $R^a$;

$R^2$ is H or an amino protecting group;

$R^3$ is —$CR^bR^cR^d$;

$R^a$ at each occurrence is independently halogen, —CN, —OH, nitro, a protected hydroxyl, a protected amino, or —X—$R^X$, wherein X is bond, O, NH, C(O), OC(O), or C(O)NH; and $R^X$ is alkyl, alkenyl, alkynyl, alkoxy, cycloalkyl, aryl, heteroaryl, or heterocyclyl, wherein the $R^X$ is optionally substituted;

$R^b$, $R^c$, and $R^d$ are independently H, alkyl, or $R^b$ and $R^c$ together with the carbon they are attached to form a ring;

the method comprising:

(i) mixing $R^1$—COOD with a compound of formula (II), a base, and a photocatalyst in an essentially $H_2O$ free solvent comprising $D_2O$ and an organic solvent to form a mixture; and

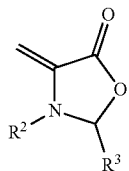
(II)

(ii) exposing the mixture of (i) to light, thereby producing the deuterated compound of formula (I), or a salt thereof.

2. The method of claim 1, wherein $R^2$ is carbobenzyloxy (Cbz), butyloxycarbonyl (Boc), 9-fluorenylmethyloxycarbonyl (Fmoc), 2,2,2-trichloroethyloxycarbonyl (Troc), or allyloxycarbonyl (Alloc).

3. The method of claim 1, wherein $R^b$, $R^c$, and $R^d$ are each independently $C_{1-4}$alkyl.

4. The method of claim 1, wherein formula (II) is formula (II-a)

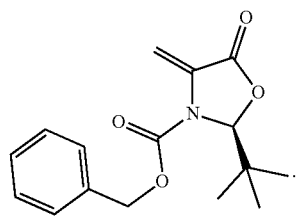
(II-a)

5. The method of claim 1, wherein the photocatalyst is

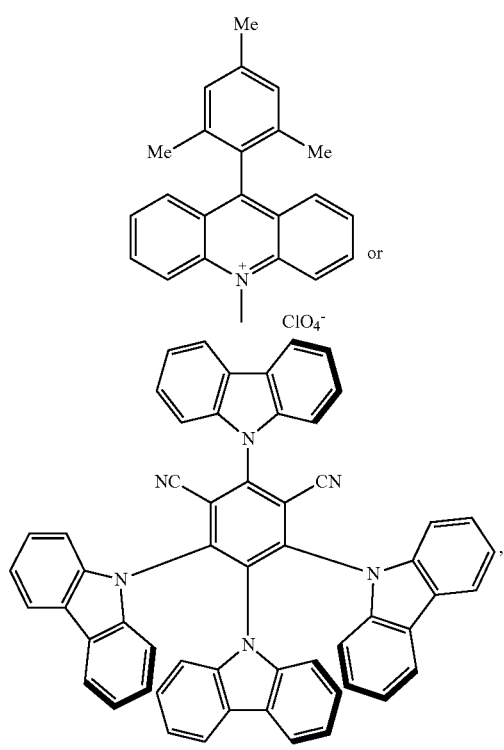

or a salt thereof.

6. The method of claim 1, wherein the essentially $H_2O$ free solvent is a combination of $D_2O$ and an anhydrous organic solvent.

7. The method of claim 1, wherein the organic solvent is acetonitrile, dimethylformamide, dichloroethane, or a combination thereof.

8. The method of claim 1, wherein the base is 1,8-diazabicyclo[5.4.0]undec-7-ene, $Cs_2CO_3$, or a combination thereof.

9. The method of claim 1, wherein $R^1$ is

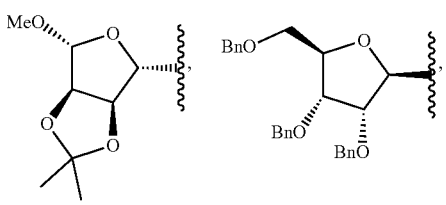

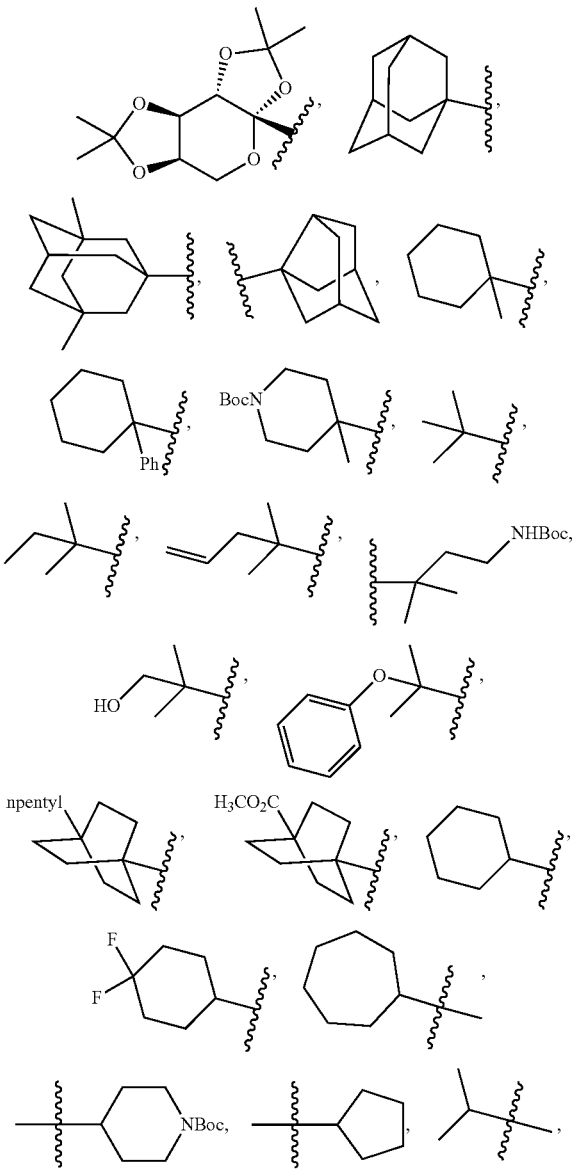

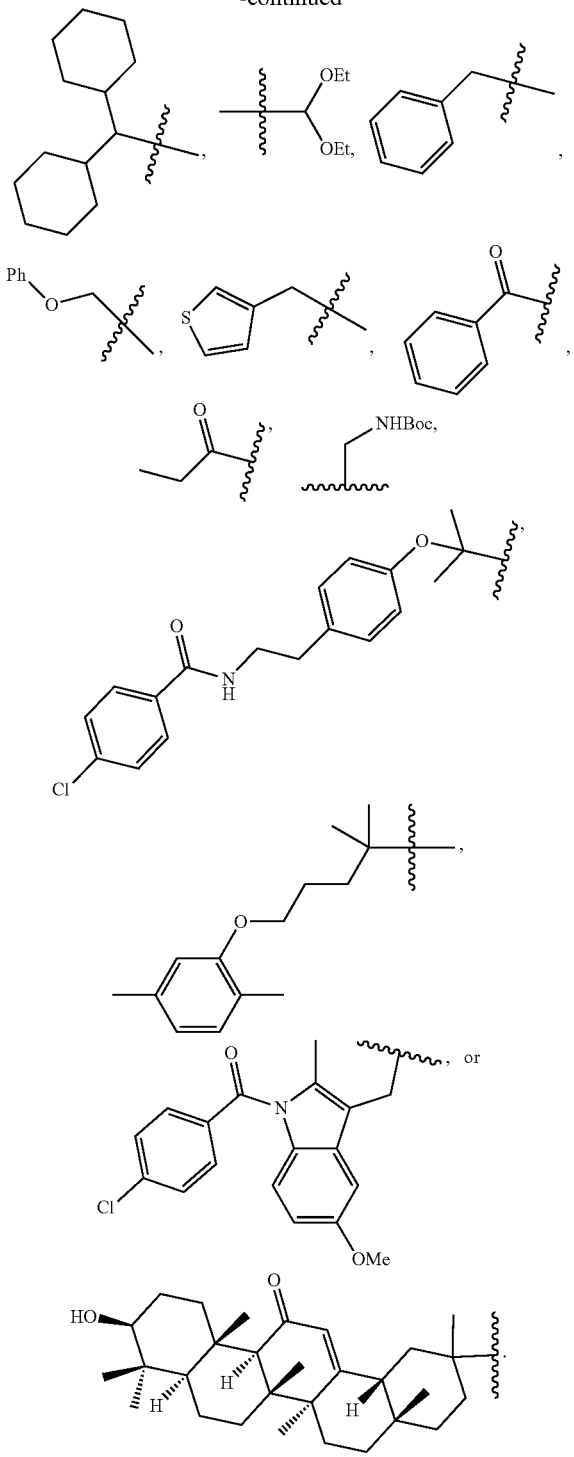

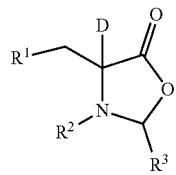

wherein
R¹ is alkyl, —C(O)alkyl, alkenyl, —C(O)alkyenyl, cycloalkyl, —C(O)cycloalkyl, cycloalkenyl, —C(O)cycloalkenyl, aryl, —C(O)aryl, heteroaryl, —C(O)heteroaryl, heterocyclyl, or —C(O)heterocyclyl, wherein R¹ is optionally substituted with one or more $R^a$;

R² is H or an amino protecting group;

R³ is —$CR^bR^cR^d$;

$R^a$ at each occurrence is independently halogen, —CN, —OH, nitro, a protected hydroxyl, a protected amino, or —X—$R^X$, wherein X is bond, O, NH, C(O), OC(O), or C(O)NH; and $R^X$ is alkyl, alkenyl, alkynyl, alkoxy, cycloalkyl, aryl, heteroaryl, or heterocyclyl, wherein the $R^X$ is optionally substituted;

$R^b$, $R^c$, and $R^d$ are independently H, alkyl, or $R^d$ is H or alkyl and $R^b$ and $R^c$ together with the carbon they are attached to form a ring.

14. The compound of claim 13, or a salt thereof, wherein R² is carbobenzyloxy (Cbz), butyloxycarbonyl (Boc), 9-fluorenylmethyloxycarbonyl (Fmoc), 2,2,2-trichloroethyloxycarbonyl (Troc), or allyloxycarbonyl (Alloc).

15. The compound of claim 13, or a salt thereof, wherein $R^b$, $R^c$, and $R^d$ are each independently $C_{1-4}$alkyl.

16. The compound of claim 13, having a structure of formula (I-a), or a salt thereof

17. The compound of claim 13, selected from the group consisting of

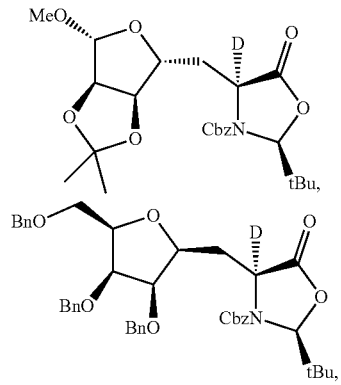

10. The method of claim 1, wherein in the level of deuterium incorporation of the deuterated compound of formula (I), or a salt thereof, is at least 90%.

11. The method of claim 10, wherein in the level of deuterium incorporation of the deuterated compound of formula (I), or a salt thereof, is at least 95%.

12. The method of claim 1, further comprising isolating the deuterated compound of formula (I), or a salt thereof.

13. A deuterated compound of formula (I), or a salt thereof,

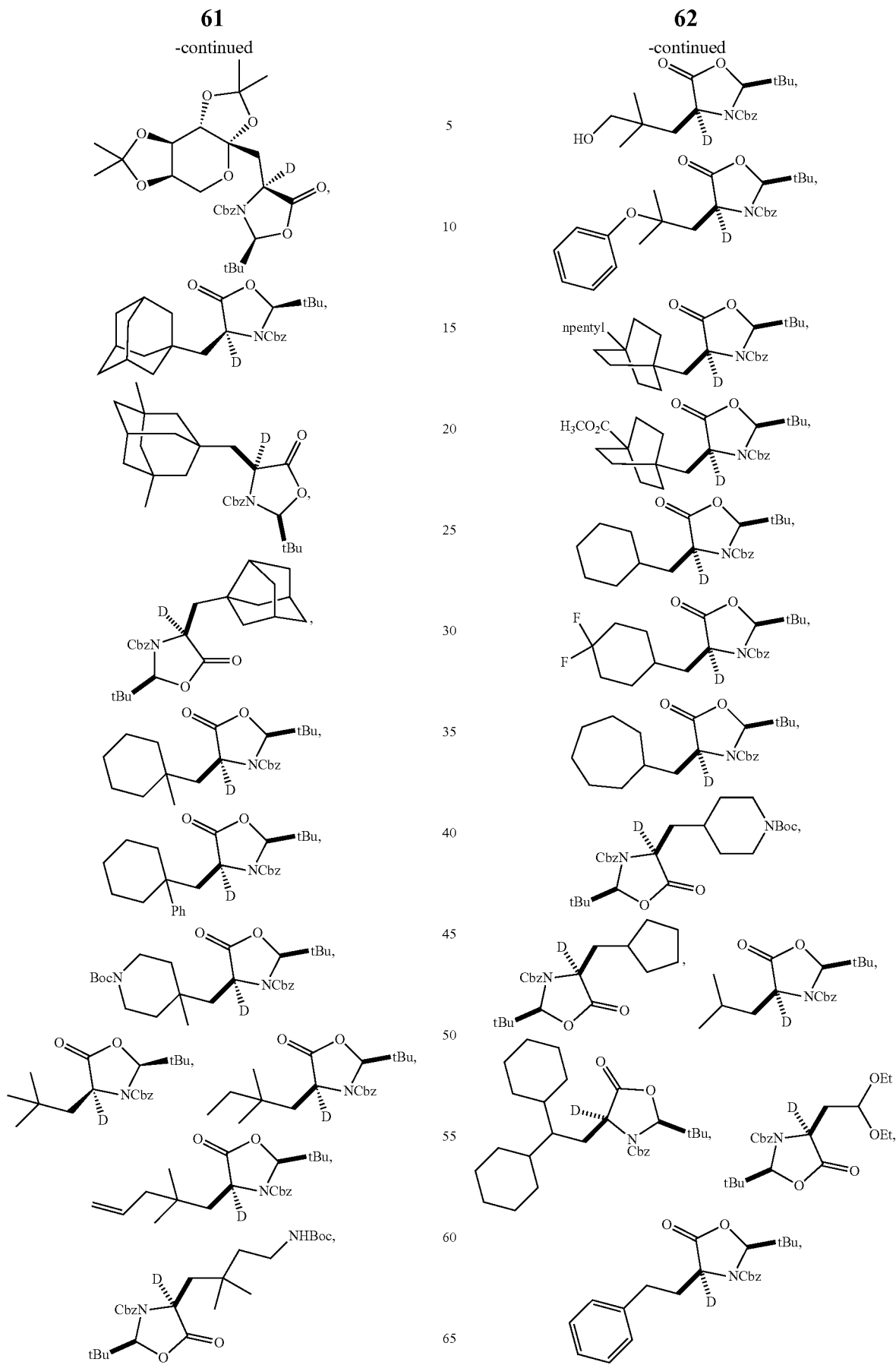

-continued

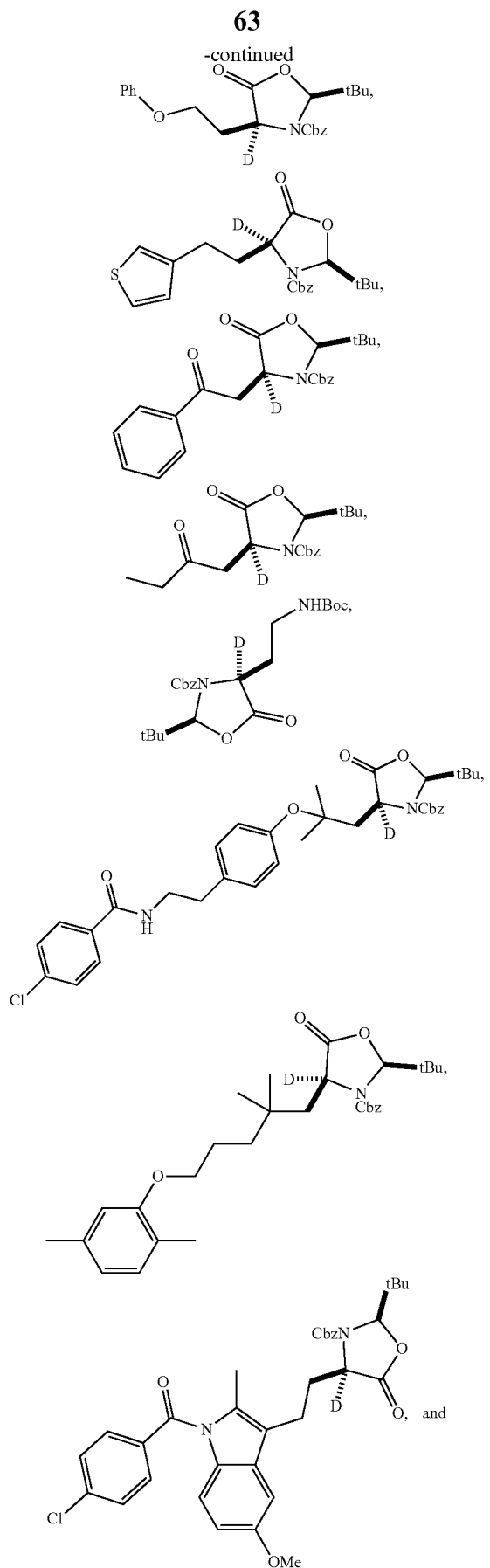

-continued

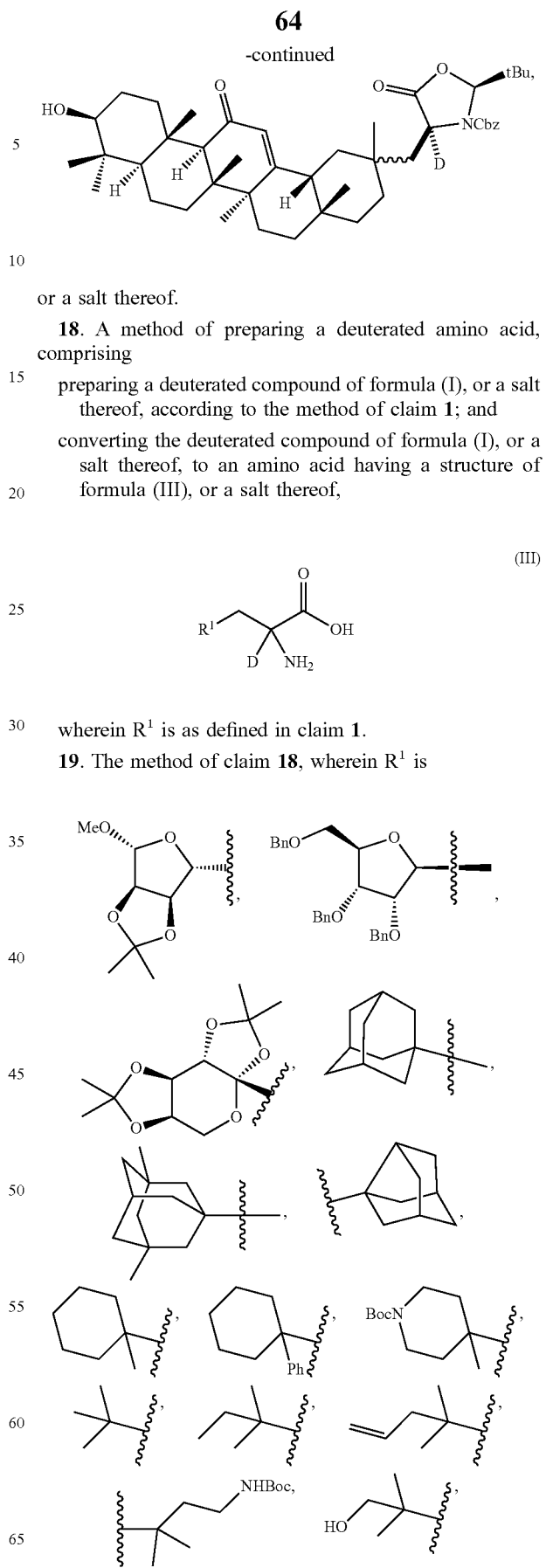

or a salt thereof.

18. A method of preparing a deuterated amino acid, comprising preparing a deuterated compound of formula (I), or a salt thereof, according to the method of claim 1; and converting the deuterated compound of formula (I), or a salt thereof, to an amino acid having a structure of formula (III), or a salt thereof, wherein $R^1$ is as defined in claim 1.

19. The method of claim 18, wherein $R^1$ is

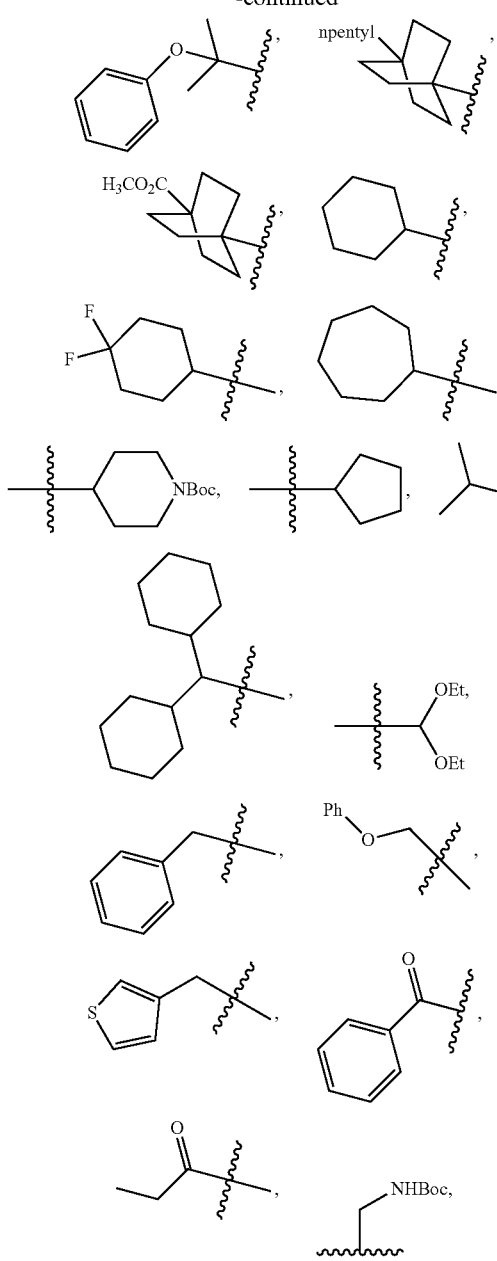
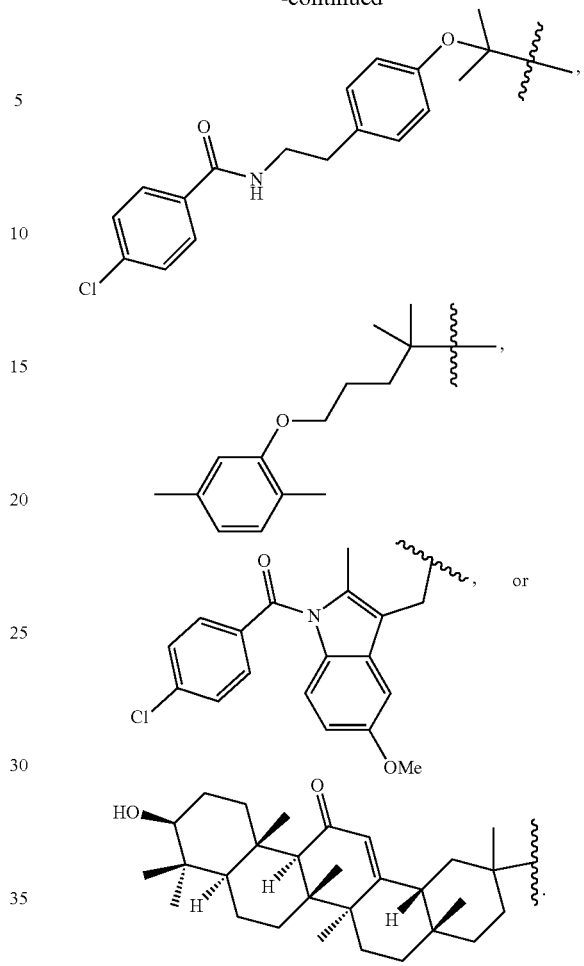
20. The method of claim 18, wherein the amino acid has a structure of formula (III-a), or a salt thereof
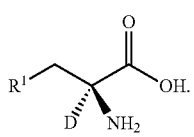
(III-a)
* * * * *